(12) United States Patent
Schnall-Levin et al.

(10) Patent No.: US 12,163,191 B2
(45) Date of Patent: Dec. 10, 2024

(54) ANALYSIS OF NUCLEIC ACID SEQUENCES

(71) Applicant: 10X GENOMICS, INC., Pleasanton, CA (US)

(72) Inventors: Michael Schnall-Levin, San Francisco, CA (US); Mirna Jarosz, Palo Alto, CA (US); Christopher Hindson, Livermore, CA (US); Kevin Ness, Pleasanton, CA (US); Serge Saxonov, Oakland, CA (US); Benjamin Hindson, Pleasanton, CA (US); Xinying Zheng, Mountain View, CA (US); Patrick Marks, San Francisco, CA (US); John Stuelpnagel, Pleasanton, CA (US)

(73) Assignee: 10X GENOMICS, INC., Pleasanton, CA (US)

( * ) Notice: Subject to any disclaimer, the term of this patent is extended or adjusted under 35 U.S.C. 154(b) by 1102 days.

(21) Appl. No.: 16/898,984

(22) Filed: Jun. 11, 2020

(65) Prior Publication Data
US 2021/0123103 A1 Apr. 29, 2021

Related U.S. Application Data

(63) Continuation of application No. 14/752,589, filed on Jun. 26, 2015, now abandoned.

(60) Provisional application No. 62/072,214, filed on Oct. 29, 2014, provisional application No. 62/017,808, filed on Jun. 26, 2014.

(51) Int. Cl.
| | |
|---|---|
| *C12Q 1/6883* | (2018.01) |
| *C12Q 1/6827* | (2018.01) |
| *G16B 30/00* | (2019.01) |
| *G16B 30/10* | (2019.01) |
| *G16B 30/20* | (2019.01) |

(52) U.S. Cl.
CPC ......... *C12Q 1/6883* (2013.01); *C12Q 1/6827* (2013.01); *G16B 30/00* (2019.02); *G16B 30/10* (2019.02); *G16B 30/20* (2019.02); *C12Q 2535/122* (2013.01); *C12Q 2600/156* (2013.01)

(58) Field of Classification Search
None
See application file for complete search history.

(56) References Cited

U.S. PATENT DOCUMENTS

| | | |
|---|---|---|
| 2,797,149 A | 6/1957 | Skeggs |
| 3,047,367 A | 7/1962 | Kessler |
| 3,479,141 A | 11/1969 | William et al. |
| 4,124,638 A | 11/1978 | Hansen |
| 4,253,846 A | 3/1981 | Smythe et al. |
| 4,377,057 A | 3/1983 | Pincha |
| 4,582,802 A | 4/1986 | Zimmerman et al. |
| 5,137,829 A | 8/1992 | Nag et al. |
| 5,149,625 A | 9/1992 | Church et al. |
| 5,185,099 A | 2/1993 | Delpuech et al. |
| 5,202,231 A | 4/1993 | Drmanac et al. |
| 5,270,183 A | 12/1993 | Corbett et al. |
| 5,413,924 A | 5/1995 | Kosak et al. |
| 5,418,149 A | 5/1995 | Gelfand et al. |
| 5,436,130 A | 7/1995 | Mathies et al. |
| 5,478,893 A | 12/1995 | Ghosh et al. |
| 5,489,523 A | 2/1996 | Mathur |
| 5,512,131 A | 4/1996 | Kumar et al. |
| 5,558,071 A | 9/1996 | Ward et al. |
| 5,585,069 A | 12/1996 | Zanzucchi et al. |
| 5,587,128 A | 12/1996 | Wilding et al. |
| 5,605,793 A | 2/1997 | Stemmer et al. |
| 5,618,711 A | 4/1997 | Gelfand et al. |
| 5,695,940 A | 12/1997 | Drmanac et al. |
| 5,700,642 A | 12/1997 | Monforte et al. |
| 5,705,628 A | 1/1998 | Hawkins |
| 5,708,153 A | 1/1998 | Dower et al. |
| 5,736,330 A | 4/1998 | Fulton |
| 5,739,036 A | 4/1998 | Parris |
| 5,744,311 A | 4/1998 | Fraiser et al. |
| 5,756,334 A | 5/1998 | Perler et al. |
| 5,830,663 A | 11/1998 | Embleton et al. |
| 5,834,197 A | 11/1998 | Parton |
| 5,842,787 A | 12/1998 | Kopf-Sill et al. |
| 5,846,719 A | 12/1998 | Brenner et al. |
| 5,846,727 A | 12/1998 | Soper et al. |
| 5,851,769 A | 12/1998 | Gray et al. |
| 5,856,174 A | 1/1999 | Lipshutz et al. |

(Continued)

FOREIGN PATENT DOCUMENTS

| | | |
|---|---|---|
| CN | 102292455 A | 12/2011 |
| CN | 103202812 A | 7/2013 |

(Continued)

OTHER PUBLICATIONS

Marie et al. "Integrated View of Genome Structure and Sequence of a Single DNA Molecule in a nanofluidic Device" PNAS, 110 (13) 4893-4898, published Mar. 11, 2013 (Year: 2013).*

(Continued)

*Primary Examiner* — Nancy J Leith
*Assistant Examiner* — Jessica D Parisi
(74) *Attorney, Agent, or Firm* — Wilson Sonsini Goodrich & Rosati

(57) ABSTRACT

The present disclosure relates to methods, compositions and systems for haplotype phasing and copy number variation assays. Included within this disclosure are methods and systems for combining the barcode comprising beads with samples in multiple separate partitions, as well as methods of processing, sequencing and analyzing barcoded samples.

10 Claims, 23 Drawing Sheets

(56) References Cited

U.S. PATENT DOCUMENTS

| | | |
|---|---|---|
| 5,872,010 A | 2/1999 | Karger et al. |
| 5,897,783 A | 4/1999 | Howe et al. |
| 5,900,481 A | 5/1999 | Lough et al. |
| 5,942,609 A | 8/1999 | Hunkapiller et al. |
| 5,958,703 A | 9/1999 | Dower et al. |
| 5,965,443 A | 10/1999 | Reznikoff et al. |
| 5,994,056 A | 11/1999 | Higuchi |
| 5,997,636 A | 12/1999 | Gamarnik et al. |
| 6,033,880 A | 3/2000 | Haff et al. |
| 6,046,003 A | 4/2000 | Mandecki |
| 6,051,377 A | 4/2000 | Mandecki |
| 6,057,107 A | 5/2000 | Fulton |
| 6,057,149 A | 5/2000 | Burns et al. |
| 6,103,537 A | 8/2000 | Ullman et al. |
| 6,110,678 A | 8/2000 | Weisburg et al. |
| 6,123,798 A | 9/2000 | Gandhi et al. |
| 6,133,436 A | 10/2000 | Koester et al. |
| 6,143,496 A | 11/2000 | Brown et al. |
| 6,159,717 A | 12/2000 | Savakis et al. |
| 6,171,850 B1 | 1/2001 | Nagle et al. |
| 6,172,218 B1 | 1/2001 | Brenner |
| 6,176,962 B1 | 1/2001 | Soane et al. |
| 6,207,384 B1 | 3/2001 | Mekalanos et al. |
| 6,258,571 B1 | 7/2001 | Chumakov et al. |
| 6,265,552 B1 | 7/2001 | Schatz |
| 6,291,243 B1 | 9/2001 | Fogarty et al. |
| 6,294,385 B1 | 9/2001 | Goryshin et al. |
| 6,296,020 B1 | 10/2001 | McNeely et al. |
| 6,297,006 B1 | 10/2001 | Drmanac et al. |
| 6,297,017 B1 | 10/2001 | Schmidt et al. |
| 6,303,343 B1 | 10/2001 | Kopf-Sill |
| 6,306,590 B1 | 10/2001 | Mehta et al. |
| 6,327,410 B1 | 12/2001 | Walt et al. |
| 6,355,198 B1 | 3/2002 | Kim et al. |
| 6,361,950 B1 | 3/2002 | Mandecki |
| 6,372,813 B1 | 4/2002 | Johnson et al. |
| 6,379,929 B1 | 4/2002 | Burns et al. |
| 6,406,848 B1 | 6/2002 | Bridgham et al. |
| 6,409,832 B2 | 6/2002 | Weigl et al. |
| 6,432,290 B1 | 8/2002 | Harrison et al. |
| 6,432,360 B1 | 8/2002 | Church |
| 6,485,944 B1 | 11/2002 | Church et al. |
| 6,492,118 B1 | 12/2002 | Abrams et al. |
| 6,511,803 B1 | 1/2003 | Church et al. |
| 6,524,456 B1 | 2/2003 | Ramsey et al. |
| 6,569,631 B1 | 5/2003 | Pantoliano et al. |
| 6,579,851 B2 | 6/2003 | Goeke et al. |
| 6,586,176 B1 | 7/2003 | Trnovsky et al. |
| 6,593,113 B1 | 7/2003 | Tenkanen et al. |
| 6,613,752 B2 | 9/2003 | Kay et al. |
| 6,632,606 B1 | 10/2003 | Ullman et al. |
| 6,632,655 B1 | 10/2003 | Mehta et al. |
| 6,670,133 B2 | 12/2003 | Knapp et al. |
| 6,723,513 B2 | 4/2004 | Lexow |
| 6,767,731 B2 | 7/2004 | Hannah |
| 6,800,298 B1 | 10/2004 | Burdick et al. |
| 6,806,052 B2 | 10/2004 | Bridgham et al. |
| 6,806,058 B2 | 10/2004 | Jesperson et al. |
| 6,859,570 B2 | 2/2005 | Walt et al. |
| 6,880,576 B2 | 4/2005 | Karp et al. |
| 6,884,788 B2 | 4/2005 | Bulpitt et al. |
| 6,913,935 B1 | 7/2005 | Thomas |
| 6,915,679 B2 | 7/2005 | Chien et al. |
| 6,929,859 B2 | 8/2005 | Chandler et al. |
| 6,969,488 B2 | 11/2005 | Bridgham et al. |
| 6,974,669 B2 | 12/2005 | Mirkin et al. |
| 7,041,481 B2 | 5/2006 | Anderson et al. |
| 7,115,400 B1 | 10/2006 | Adessi et al. |
| 7,129,091 B2 | 10/2006 | Ismagilov et al. |
| 7,138,267 B1 | 11/2006 | Jendrisak et al. |
| 7,211,654 B2 | 5/2007 | Gao et al. |
| 7,262,056 B2 | 8/2007 | Wooddell et al. |
| 7,268,167 B2 | 9/2007 | Higuchi et al. |
| 7,282,370 B2 | 10/2007 | Bridgham et al. |
| 7,294,503 B2 | 11/2007 | Quake et al. |
| 7,297,485 B2 | 11/2007 | Bornarth et al. |
| 7,316,903 B2 | 1/2008 | Yanagihara et al. |
| 7,323,305 B2 | 1/2008 | Leamon et al. |
| 7,329,493 B2 | 2/2008 | Chou et al. |
| 7,425,431 B2 | 9/2008 | Church et al. |
| 7,536,928 B2 | 5/2009 | Kazuno |
| 7,544,473 B2 | 6/2009 | Brenner |
| 7,604,938 B2 | 10/2009 | Takahashi et al. |
| 7,608,434 B2 | 10/2009 | Reznikoff et al. |
| 7,608,451 B2 | 10/2009 | Cooper et al. |
| 7,622,076 B2 | 11/2009 | Davies et al. |
| 7,622,280 B2 | 11/2009 | Holliger et al. |
| 7,638,276 B2 | 12/2009 | Griffiths et al. |
| 7,645,596 B2 | 1/2010 | Williams et al. |
| 7,666,664 B2 | 2/2010 | Sarofim et al. |
| 7,700,325 B2 | 4/2010 | Cantor et al. |
| 7,708,949 B2 | 5/2010 | Stone et al. |
| 7,709,197 B2 | 5/2010 | Drmanac |
| 7,745,178 B2 | 6/2010 | Dong |
| 7,745,218 B2 | 6/2010 | Kim et al. |
| 7,772,287 B2 | 8/2010 | Higuchi et al. |
| 7,776,927 B2 | 8/2010 | Chu et al. |
| RE41,780 E | 9/2010 | Anderson et al. |
| 7,799,553 B2 | 9/2010 | Mathies et al. |
| 7,842,457 B2 | 11/2010 | Berka et al. |
| 7,901,891 B2 | 3/2011 | Drmanac |
| 7,910,354 B2 | 3/2011 | Drmanac et al. |
| 7,927,797 B2 | 4/2011 | Nobile et al. |
| 7,943,671 B2 | 5/2011 | Herminghaus et al. |
| 7,947,477 B2 | 5/2011 | Schroeder et al. |
| 7,960,104 B2 | 6/2011 | Drmanac et al. |
| 7,968,287 B2 | 6/2011 | Griffiths et al. |
| 7,972,778 B2 | 7/2011 | Brown et al. |
| 8,003,312 B2 | 8/2011 | Krutzik et al. |
| 8,008,018 B2 | 8/2011 | Quake et al. |
| 8,053,192 B2 | 11/2011 | Bignell et al. |
| 8,067,159 B2 | 11/2011 | Brown et al. |
| 8,101,346 B2 | 1/2012 | Takahama |
| 8,124,404 B2 | 2/2012 | Alphey et al. |
| 8,133,719 B2 | 3/2012 | Drmanac et al. |
| 8,137,563 B2 | 3/2012 | Ma et al. |
| 8,168,385 B2 | 5/2012 | Brenner |
| 8,252,539 B2 | 8/2012 | Quake et al. |
| 8,268,564 B2 | 9/2012 | Roth et al. |
| 8,273,573 B2 | 9/2012 | Ismagilov et al. |
| 8,278,071 B2 | 10/2012 | Brown et al. |
| 8,298,767 B2 | 10/2012 | Brenner et al. |
| 8,304,193 B2 | 11/2012 | Ismagilov et al. |
| 8,318,433 B2 | 11/2012 | Brenner |
| 8,318,460 B2 | 11/2012 | Cantor et al. |
| 8,329,407 B2 | 12/2012 | Ismagilov et al. |
| 8,337,778 B2 | 12/2012 | Stone et al. |
| 8,361,299 B2 | 1/2013 | Sabin et al. |
| 8,420,386 B2 | 4/2013 | Ivics et al. |
| 8,461,129 B2 | 6/2013 | Bolduc et al. |
| 8,563,274 B2 | 10/2013 | Brenner et al. |
| 8,592,150 B2 | 11/2013 | Drmanac et al. |
| 8,598,328 B2 | 12/2013 | Koga et al. |
| 8,603,749 B2 | 12/2013 | Gillevet |
| 8,658,430 B2 | 2/2014 | Miller et al. |
| 8,679,756 B1 | 3/2014 | Brenner et al. |
| 8,748,094 B2 | 6/2014 | Weitz et al. |
| 8,748,102 B2 | 6/2014 | Berka et al. |
| 8,765,380 B2 | 7/2014 | Berka et al. |
| 8,822,148 B2 | 9/2014 | Ismagilov et al. |
| 8,829,171 B2 | 9/2014 | Steemers et al. |
| 8,835,358 B2 | 9/2014 | Fodor et al. |
| 8,871,444 B2 | 10/2014 | Griffiths et al. |
| 8,889,083 B2 | 11/2014 | Ismagilov et al. |
| 8,927,218 B2 | 1/2015 | Forsyth |
| 8,975,302 B2 | 3/2015 | Light et al. |
| 8,986,628 B2 | 3/2015 | Stone et al. |
| 9,005,935 B2 | 4/2015 | Belyaev |
| 9,012,370 B2 | 4/2015 | Hong |
| 9,012,390 B2 | 4/2015 | Holtze et al. |
| 9,017,948 B2 | 4/2015 | Agresti et al. |
| 9,029,083 B2 | 5/2015 | Griffiths et al. |
| 9,029,085 B2 | 5/2015 | Agresti et al. |
| 9,040,256 B2 | 5/2015 | Grunenwald et al. |

(56) References Cited

U.S. PATENT DOCUMENTS

| | | |
|---|---|---|
| 9,068,210 B2 | 6/2015 | Agresti et al. |
| 9,074,251 B2 | 7/2015 | Steemers et al. |
| 9,080,211 B2 | 7/2015 | Grunenwald et al. |
| 9,085,798 B2 | 7/2015 | Chee |
| 9,089,844 B2 | 7/2015 | Hiddessen et al. |
| 9,102,980 B2 | 8/2015 | Brenner et al. |
| 9,126,160 B2 | 9/2015 | Ness et al. |
| 9,133,009 B2 | 9/2015 | Baroud et al. |
| 9,150,916 B2 | 10/2015 | Christen et al. |
| 9,156,010 B2 | 10/2015 | Colston et al. |
| 9,175,295 B2 | 11/2015 | Kaminaka et al. |
| 9,194,861 B2 | 11/2015 | Hindson et al. |
| 9,216,392 B2 | 12/2015 | Hindson et al. |
| 9,238,206 B2 | 1/2016 | Rotem et al. |
| 9,238,671 B2 | 1/2016 | Goryshin et al. |
| 9,249,460 B2 | 2/2016 | Pushkarev et al. |
| 9,266,104 B2 | 2/2016 | Link |
| 9,273,349 B2 | 3/2016 | Nguyen et al. |
| 9,290,808 B2 | 3/2016 | Fodor et al. |
| 9,328,382 B2 | 5/2016 | Drmanac et al. |
| 9,347,059 B2 | 5/2016 | Saxonov |
| 9,371,598 B2 | 6/2016 | Chee |
| 9,388,465 B2 | 7/2016 | Hindson et al. |
| 9,410,201 B2 | 8/2016 | Hindson et al. |
| 9,417,190 B2 | 8/2016 | Hindson et al. |
| 9,436,088 B2 | 9/2016 | Seul et al. |
| 9,486,757 B2 | 11/2016 | Romanowsky et al. |
| 9,498,761 B2 | 11/2016 | Holtze et al. |
| 9,500,664 B2 | 11/2016 | Ness et al. |
| 9,567,631 B2 | 2/2017 | Hindson et al. |
| 9,574,226 B2 | 2/2017 | Gormley et al. |
| 9,593,365 B2 | 3/2017 | Frisen et al. |
| 9,623,384 B2 | 4/2017 | Hindson et al. |
| 9,637,799 B2 | 5/2017 | Fan et al. |
| 9,644,204 B2 | 5/2017 | Hindson et al. |
| 9,689,024 B2 | 6/2017 | Hindson et al. |
| 9,694,361 B2 | 7/2017 | Bharadwaj et al. |
| 9,695,468 B2 | 7/2017 | Hindson et al. |
| 9,701,998 B2 | 7/2017 | Hindson et al. |
| 9,764,322 B2 | 9/2017 | Hiddessen et al. |
| 9,824,068 B2 | 11/2017 | Wong |
| 9,856,530 B2 | 1/2018 | Hindson et al. |
| 9,868,979 B2 | 1/2018 | Chee et al. |
| 9,879,313 B2 | 1/2018 | Chee et al. |
| 9,946,577 B1 | 4/2018 | Stafford et al. |
| 9,951,386 B2 | 4/2018 | Hindson et al. |
| 9,957,558 B2 | 5/2018 | Leamon et al. |
| 9,975,122 B2 | 5/2018 | Masquelier et al. |
| 10,011,872 B1 | 7/2018 | Belgrader et al. |
| 10,017,759 B2 | 7/2018 | Kaper et al. |
| 10,030,261 B2 | 7/2018 | Frisen et al. |
| 10,030,267 B2 | 7/2018 | Hindson et al. |
| 10,041,116 B2 | 8/2018 | Hindson et al. |
| 10,053,723 B2 | 8/2018 | Hindson et al. |
| 10,059,989 B2 | 8/2018 | Giresi et al. |
| 10,071,377 B2 | 9/2018 | Bharadwaj et al. |
| 10,119,167 B2 | 11/2018 | Srinivasan et al. |
| 10,137,449 B2 | 11/2018 | Bharadwaj et al. |
| 10,144,950 B2 | 12/2018 | Nolan |
| 10,150,117 B2 | 12/2018 | Bharadwaj et al. |
| 10,150,963 B2 | 12/2018 | Hindson et al. |
| 10,150,964 B2 | 12/2018 | Hindson et al. |
| 10,150,995 B1 | 12/2018 | Giresi et al. |
| 10,161,007 B2 | 12/2018 | Abate et al. |
| 10,174,310 B2 | 1/2019 | Nolan |
| 10,208,343 B2 | 2/2019 | Hindson et al. |
| 10,221,436 B2 | 3/2019 | Hardenbol et al. |
| 10,221,442 B2 | 3/2019 | Hindson et al. |
| 10,227,648 B2 | 3/2019 | Hindson et al. |
| 10,253,364 B2 | 4/2019 | Hindson et al. |
| 10,273,541 B2 | 4/2019 | Hindson et al. |
| 10,323,279 B2 | 6/2019 | Hindson et al. |
| 10,337,061 B2 | 7/2019 | Hindson et al. |
| 10,344,329 B2 | 7/2019 | Hindson et al. |
| 10,347,365 B2 | 7/2019 | Wong et al. |
| 10,357,771 B2 | 7/2019 | Bharadwaj et al. |
| 10,395,758 B2 | 8/2019 | Schnall-Levin |
| 10,400,280 B2 | 9/2019 | Hindson et al. |
| 10,428,326 B2 | 10/2019 | Belhocine et al. |
| 10,450,607 B2 | 10/2019 | Hindson et al. |
| 10,457,986 B2 | 10/2019 | Hindson et al. |
| 10,480,028 B2 | 11/2019 | Hindson et al. |
| 10,533,221 B2 | 1/2020 | Hindson et al. |
| 10,544,413 B2 | 1/2020 | Bharadwaj et al. |
| 10,549,279 B2 | 2/2020 | Bharadwaj et al. |
| 10,590,244 B2 | 3/2020 | Delaney et al. |
| 10,697,008 B2 | 6/2020 | Blauwkamp et al. |
| 10,745,742 B2 | 8/2020 | Bent et al. |
| 10,752,949 B2 | 8/2020 | Hindson et al. |
| 10,774,374 B2 | 9/2020 | Frisen et al. |
| 10,815,525 B2 | 10/2020 | Lucero et al. |
| 10,829,815 B2 | 11/2020 | Bharadwaj et al. |
| 10,837,047 B2 | 11/2020 | Delaney et al. |
| 10,874,997 B2 | 12/2020 | Weitz et al. |
| 10,876,147 B2 | 12/2020 | Meer et al. |
| 10,995,333 B2 | 5/2021 | Pfeiffer |
| 11,459,607 B1 | 10/2022 | Terry et al. |
| 11,467,153 B2 | 10/2022 | Belhocine et al. |
| 11,655,499 B1 | 5/2023 | Pfeiffer |
| 2001/0020588 A1 | 9/2001 | Adourian et al. |
| 2001/0036669 A1 | 11/2001 | Jedrzejewski et al. |
| 2001/0041357 A1 | 11/2001 | Fouillet et al. |
| 2001/0044109 A1 | 11/2001 | Mandecki |
| 2001/0048900 A1 | 12/2001 | Bardell et al. |
| 2001/0053519 A1 | 12/2001 | Fodor et al. |
| 2002/0001856 A1 | 1/2002 | Chow et al. |
| 2002/0005354 A1 | 1/2002 | Spence et al. |
| 2002/0034737 A1 | 3/2002 | Drmanac |
| 2002/0043463 A1 | 4/2002 | Shenderov |
| 2002/0051971 A1 | 5/2002 | Stuelpnagel et al. |
| 2002/0051992 A1 | 5/2002 | Bridgham et al. |
| 2002/0058332 A1 | 5/2002 | Quake et al. |
| 2002/0065609 A1 | 5/2002 | Ashby |
| 2002/0068278 A1 | 6/2002 | Giese et al. |
| 2002/0089100 A1 | 7/2002 | Kawasaki |
| 2002/0092767 A1 | 7/2002 | Bjornson et al. |
| 2002/0113009 A1 | 8/2002 | O'Connor et al. |
| 2002/0119455 A1 | 8/2002 | Chan |
| 2002/0119536 A1 | 8/2002 | Stern |
| 2002/0119544 A1 | 8/2002 | Yan et al. |
| 2002/0127736 A1 | 9/2002 | Chou et al. |
| 2002/0131147 A1 | 9/2002 | Paolini et al. |
| 2002/0160518 A1 | 10/2002 | Hayenga et al. |
| 2002/0164820 A1 | 11/2002 | Brown |
| 2002/0166582 A1 | 11/2002 | O'Connor et al. |
| 2002/0172965 A1 | 11/2002 | Kamb et al. |
| 2002/0175079 A1 | 11/2002 | Christel et al. |
| 2002/0179849 A1 | 12/2002 | Maher et al. |
| 2003/0005967 A1 | 1/2003 | Karp |
| 2003/0007898 A1 | 1/2003 | Bohm et al. |
| 2003/0008285 A1 | 1/2003 | Fischer |
| 2003/0008323 A1 | 1/2003 | Ravkin et al. |
| 2003/0022231 A1 | 1/2003 | Wangh et al. |
| 2003/0027214 A1 | 2/2003 | Kamb |
| 2003/0027221 A1 | 2/2003 | Scott et al. |
| 2003/0028981 A1 | 2/2003 | Chandler et al. |
| 2003/0032141 A1 | 2/2003 | Nguyen et al. |
| 2003/0036206 A1 | 2/2003 | Chien et al. |
| 2003/0039978 A1 | 2/2003 | Hannah |
| 2003/0044777 A1 | 3/2003 | Beattie |
| 2003/0044836 A1 | 3/2003 | Levine et al. |
| 2003/0075446 A1 | 4/2003 | Culbertson et al. |
| 2003/0082587 A1 | 5/2003 | Seul et al. |
| 2003/0089605 A1 | 5/2003 | Timperman |
| 2003/0104466 A1 | 6/2003 | Knapp et al. |
| 2003/0108897 A1 | 6/2003 | Drmanac |
| 2003/0124509 A1 | 7/2003 | Kenis et al. |
| 2003/0149307 A1 | 8/2003 | Hai et al. |
| 2003/0170698 A1 | 9/2003 | Gascoyne et al. |
| 2003/0182068 A1 | 9/2003 | Battersby et al. |
| 2003/0207260 A1 | 11/2003 | Trnovsky et al. |
| 2003/0215862 A1 | 11/2003 | Parce et al. |
| 2004/0063138 A1 | 4/2004 | McGinnis et al. |
| 2004/0081962 A1 | 4/2004 | Chen et al. |

(56) References Cited

U.S. PATENT DOCUMENTS

| | | |
|---|---|---|
| 2004/0101680 A1 | 5/2004 | Barber, Jr. |
| 2004/0101880 A1 | 5/2004 | Rozwadowski et al. |
| 2004/0132122 A1 | 7/2004 | Banerjee et al. |
| 2004/0224331 A1 | 11/2004 | Cantor et al. |
| 2004/0258701 A1 | 12/2004 | Dominowski et al. |
| 2005/0019839 A1 | 1/2005 | Jespersen et al. |
| 2005/0037397 A1 | 2/2005 | Mirkin et al. |
| 2005/0042625 A1 | 2/2005 | Schmidt et al. |
| 2005/0079510 A1 | 4/2005 | Berka et al. |
| 2005/0130188 A1 | 6/2005 | Walt et al. |
| 2005/0172476 A1 | 8/2005 | Stone et al. |
| 2005/0181379 A1 | 8/2005 | Su et al. |
| 2005/0202429 A1 | 9/2005 | Trau et al. |
| 2005/0202489 A1 | 9/2005 | Cho et al. |
| 2005/0221339 A1 | 10/2005 | Griffiths et al. |
| 2005/0244850 A1 | 11/2005 | Huang et al. |
| 2005/0250147 A1 | 11/2005 | Macevicz |
| 2005/0266582 A1 | 12/2005 | Modlin et al. |
| 2005/0272159 A1 | 12/2005 | Ismagilov et al. |
| 2005/0287572 A1 | 12/2005 | Mathies et al. |
| 2006/0002890 A1 | 1/2006 | Hersel et al. |
| 2006/0008799 A1 | 1/2006 | Cai et al. |
| 2006/0020371 A1 | 1/2006 | Ham et al. |
| 2006/0040382 A1 | 2/2006 | Heffron et al. |
| 2006/0073487 A1 | 4/2006 | Oliver et al. |
| 2006/0078888 A1 | 4/2006 | Griffiths et al. |
| 2006/0153924 A1 | 7/2006 | Griffiths et al. |
| 2006/0163385 A1 | 7/2006 | Link et al. |
| 2006/0177832 A1 | 8/2006 | Brenner |
| 2006/0177833 A1 | 8/2006 | Brenner |
| 2006/0199193 A1 | 9/2006 | Koo et al. |
| 2006/0240506 A1 | 10/2006 | Kushmaro et al. |
| 2006/0257893 A1 | 11/2006 | Takahashi et al. |
| 2006/0263888 A1 | 11/2006 | Fritz et al. |
| 2006/0275782 A1 | 12/2006 | Gunderson et al. |
| 2006/0286570 A1 | 12/2006 | Rowlen et al. |
| 2006/0292583 A1 | 12/2006 | Schneider et al. |
| 2007/0003442 A1 | 1/2007 | Link et al. |
| 2007/0009954 A1 | 1/2007 | Wang et al. |
| 2007/0020617 A1 | 1/2007 | Trnovsky et al. |
| 2007/0020640 A1 | 1/2007 | McCloskey et al. |
| 2007/0026401 A1 | 2/2007 | Hofmann et al. |
| 2007/0031829 A1 | 2/2007 | Yasuno et al. |
| 2007/0042400 A1 | 2/2007 | Choi et al. |
| 2007/0042419 A1 | 2/2007 | Barany et al. |
| 2007/0054119 A1 | 3/2007 | Garstecki et al. |
| 2007/0072208 A1 | 3/2007 | Drmanac |
| 2007/0077572 A1 | 4/2007 | Tawfik et al. |
| 2007/0092914 A1 | 4/2007 | Griffiths et al. |
| 2007/0099208 A1 | 5/2007 | Drmanac et al. |
| 2007/0111241 A1 | 5/2007 | Cereb et al. |
| 2007/0134277 A1 | 6/2007 | Chen et al. |
| 2007/0154903 A1 | 7/2007 | Marla et al. |
| 2007/0160503 A1 | 7/2007 | Sethu et al. |
| 2007/0172873 A1 | 7/2007 | Brenner et al. |
| 2007/0190543 A1 | 8/2007 | Livak |
| 2007/0195127 A1 | 8/2007 | Ahn et al. |
| 2007/0196397 A1 | 8/2007 | Torii et al. |
| 2007/0207060 A1 | 9/2007 | Zou et al. |
| 2007/0228588 A1 | 10/2007 | Noritomi et al. |
| 2007/0231823 A1 | 10/2007 | McKernan et al. |
| 2007/0238113 A1 | 10/2007 | Kanda et al. |
| 2007/0259357 A1 | 11/2007 | Brenner |
| 2007/0264320 A1 | 11/2007 | Lee et al. |
| 2008/0003142 A1 | 1/2008 | Link et al. |
| 2008/0004436 A1 | 1/2008 | Tawfik et al. |
| 2008/0014589 A1 | 1/2008 | Link et al. |
| 2008/0056948 A1 | 3/2008 | Dale et al. |
| 2008/0124726 A1 | 5/2008 | Monforte |
| 2008/0138878 A1 | 6/2008 | Kubu et al. |
| 2008/0166720 A1 | 7/2008 | Hsieh et al. |
| 2008/0213766 A1 | 9/2008 | Brown et al. |
| 2008/0228268 A1 | 9/2008 | Shannon et al. |
| 2008/0241820 A1 | 10/2008 | Krutzik et al. |
| 2008/0242560 A1 | 10/2008 | Gunderson et al. |
| 2008/0268431 A1 | 10/2008 | Choy et al. |
| 2008/0268450 A1 | 10/2008 | Nam et al. |
| 2009/0005252 A1 | 1/2009 | Drmanac et al. |
| 2009/0011943 A1 | 1/2009 | Drmanac et al. |
| 2009/0012187 A1 | 1/2009 | Chu et al. |
| 2009/0025277 A1 | 1/2009 | Takanashi |
| 2009/0035770 A1 | 2/2009 | Mathies et al. |
| 2009/0047713 A1 | 2/2009 | Handique |
| 2009/0048124 A1 | 2/2009 | Leamon et al. |
| 2009/0053169 A1 | 2/2009 | Castillo et al. |
| 2009/0062129 A1 | 3/2009 | McKernan et al. |
| 2009/0068170 A1 | 3/2009 | Weitz et al. |
| 2009/0098555 A1 | 4/2009 | Roth et al. |
| 2009/0099041 A1 | 4/2009 | Church et al. |
| 2009/0105959 A1 | 4/2009 | Braverman et al. |
| 2009/0118488 A1 | 5/2009 | Drmanac et al. |
| 2009/0131543 A1 | 5/2009 | Weitz et al. |
| 2009/0134027 A1 | 5/2009 | Jary |
| 2009/0137404 A1 | 5/2009 | Drmanac et al. |
| 2009/0137414 A1 | 5/2009 | Drmanac et al. |
| 2009/0143244 A1 | 6/2009 | Bridgham et al. |
| 2009/0148961 A1 | 6/2009 | Luchini et al. |
| 2009/0155563 A1 | 6/2009 | Petsev et al. |
| 2009/0155780 A1 | 6/2009 | Xiao et al. |
| 2009/0155781 A1 | 6/2009 | Drmanac et al. |
| 2009/0197248 A1 | 8/2009 | Griffiths et al. |
| 2009/0197772 A1 | 8/2009 | Griffiths et al. |
| 2009/0202984 A1 | 8/2009 | Cantor |
| 2009/0203531 A1 | 8/2009 | Kurn |
| 2009/0235990 A1 | 9/2009 | Beer |
| 2009/0264299 A1 | 10/2009 | Drmanac et al. |
| 2009/0269248 A1 | 10/2009 | Falb et al. |
| 2009/0286687 A1 | 11/2009 | Dressman et al. |
| 2009/0325260 A1 | 12/2009 | Otto et al. |
| 2010/0021973 A1 | 1/2010 | Makarov et al. |
| 2010/0021984 A1 | 1/2010 | Edd et al. |
| 2010/0022414 A1 | 1/2010 | Link et al. |
| 2010/0035254 A1 | 2/2010 | Williams |
| 2010/0062494 A1 | 3/2010 | Church et al. |
| 2010/0069263 A1 | 3/2010 | Shendure et al. |
| 2010/0086914 A1 | 4/2010 | Bentley et al. |
| 2010/0105112 A1 | 4/2010 | Holtze et al. |
| 2010/0105866 A1 | 4/2010 | Fraden et al. |
| 2010/0113296 A1 | 5/2010 | Myerson |
| 2010/0120098 A1 | 5/2010 | Grunenwald et al. |
| 2010/0130369 A1 | 5/2010 | Shenderov et al. |
| 2010/0136544 A1 | 6/2010 | Agresti et al. |
| 2010/0137163 A1 | 6/2010 | Link et al. |
| 2010/0173394 A1 | 7/2010 | Colston, Jr. et al. |
| 2010/0184928 A1 | 7/2010 | Kumacheva |
| 2010/0187705 A1 | 7/2010 | Lee et al. |
| 2010/0210479 A1 | 8/2010 | Griffiths et al. |
| 2010/0216153 A1 | 8/2010 | Lapidus et al. |
| 2010/0248237 A1 | 9/2010 | Froehlich et al. |
| 2010/0248991 A1 | 9/2010 | Roesler et al. |
| 2010/0304982 A1 | 12/2010 | Hinz et al. |
| 2011/0000560 A1 | 1/2011 | Miller et al. |
| 2011/0008775 A1 | 1/2011 | Gao et al. |
| 2011/0028412 A1 | 2/2011 | Cappello et al. |
| 2011/0033548 A1 | 2/2011 | Lai et al. |
| 2011/0033854 A1 | 2/2011 | Drmanac et al. |
| 2011/0053798 A1 | 3/2011 | Hindson et al. |
| 2011/0059556 A1 | 3/2011 | Strey et al. |
| 2011/0071053 A1 | 3/2011 | Drmanac et al. |
| 2011/0086780 A1 | 4/2011 | Colston, Jr. et al. |
| 2011/0092376 A1 | 4/2011 | Colston, Jr. et al. |
| 2011/0092392 A1 | 4/2011 | Colston, Jr. et al. |
| 2011/0160078 A1 | 6/2011 | Fodor et al. |
| 2011/0166034 A1 | 7/2011 | Kwong et al. |
| 2011/0195496 A1 | 8/2011 | Muraguchi et al. |
| 2011/0201526 A1 | 8/2011 | Berka et al. |
| 2011/0212090 A1 | 9/2011 | Pedersen et al. |
| 2011/0217736 A1 | 9/2011 | Hindson |
| 2011/0218123 A1 | 9/2011 | Weitz et al. |
| 2011/0257889 A1 | 10/2011 | Klammer et al. |
| 2011/0263457 A1 | 10/2011 | Krutzik et al. |
| 2011/0267457 A1 | 11/2011 | Weitz et al. |
| 2011/0281736 A1 | 11/2011 | Drmanac et al. |
| 2011/0281738 A1 | 11/2011 | Drmanac et al. |

(56) References Cited

U.S. PATENT DOCUMENTS

| | | |
|---|---|---|
| 2011/0287435 A1 | 11/2011 | Grunenwald et al. |
| 2011/0305761 A1 | 12/2011 | Shum et al. |
| 2011/0306141 A1 | 12/2011 | Bronchetti et al. |
| 2011/0319281 A1 | 12/2011 | Drmanac |
| 2012/0000777 A1 | 1/2012 | Garrell et al. |
| 2012/0003657 A1 | 1/2012 | Myllykangas et al. |
| 2012/0010091 A1 | 1/2012 | Linnarson |
| 2012/0010098 A1 | 1/2012 | Griffiths et al. |
| 2012/0010107 A1 | 1/2012 | Griffiths et al. |
| 2012/0014977 A1 | 1/2012 | Furihata et al. |
| 2012/0015382 A1 | 1/2012 | Weitz et al. |
| 2012/0015822 A1 | 1/2012 | Weitz et al. |
| 2012/0041727 A1 | 2/2012 | Mishra et al. |
| 2012/0071331 A1 | 3/2012 | Casbon et al. |
| 2012/0121481 A1 | 5/2012 | Romanowsky et al. |
| 2012/0132288 A1 | 5/2012 | Weitz et al. |
| 2012/0135893 A1 | 5/2012 | Drmanac et al. |
| 2012/0165219 A1 | 6/2012 | Van Der Zaag et al. |
| 2012/0172259 A1 | 7/2012 | Rigatti et al. |
| 2012/0184449 A1 | 7/2012 | Hixson et al. |
| 2012/0190032 A1 | 7/2012 | Ness et al. |
| 2012/0190037 A1 | 7/2012 | Durin et al. |
| 2012/0196288 A1 | 8/2012 | Beer |
| 2012/0208705 A1 | 8/2012 | Steemers et al. |
| 2012/0208724 A1 | 8/2012 | Steemers et al. |
| 2012/0211084 A1 | 8/2012 | Weitz et al. |
| 2012/0219947 A1 | 8/2012 | Yurkovetsky et al. |
| 2012/0220494 A1 | 8/2012 | Samuels et al. |
| 2012/0220497 A1 | 8/2012 | Jacobson et al. |
| 2012/0222748 A1 | 9/2012 | Weitz et al. |
| 2012/0230338 A1 | 9/2012 | Ganeshalingam et al. |
| 2012/0231972 A1 | 9/2012 | Golyshin et al. |
| 2012/0252012 A1 | 10/2012 | Armougom et al. |
| 2012/0253689 A1 | 10/2012 | Rogan |
| 2012/0289428 A1 | 11/2012 | Duffy et al. |
| 2012/0297493 A1 | 11/2012 | Cooper et al. |
| 2012/0309002 A1 | 12/2012 | Link |
| 2012/0316074 A1 | 12/2012 | Saxonov |
| 2013/0017978 A1 | 1/2013 | Kavanagh et al. |
| 2013/0018970 A1 | 1/2013 | Woundy et al. |
| 2013/0022682 A1 | 1/2013 | Lee et al. |
| 2013/0028812 A1 | 1/2013 | Prieto et al. |
| 2013/0041004 A1 | 2/2013 | Drager et al. |
| 2013/0046030 A1 | 2/2013 | Rotem et al. |
| 2013/0059310 A1 | 3/2013 | Brenner et al. |
| 2013/0078638 A1 | 3/2013 | Berka et al. |
| 2013/0079231 A1 | 3/2013 | Pushkarev et al. |
| 2013/0079251 A1 | 3/2013 | Boles |
| 2013/0084243 A1 | 4/2013 | Goetsch et al. |
| 2013/0096073 A1 | 4/2013 | Sidelman |
| 2013/0109575 A1 | 5/2013 | Kleinschmidt et al. |
| 2013/0109576 A1 | 5/2013 | Shuber et al. |
| 2013/0121893 A1 | 5/2013 | Delamarche et al. |
| 2013/0130919 A1 | 5/2013 | Chen et al. |
| 2013/0157870 A1 | 6/2013 | Pushkarev et al. |
| 2013/0157899 A1 | 6/2013 | Adler, Jr. et al. |
| 2013/0171679 A1 | 7/2013 | Lee et al. |
| 2013/0178368 A1 | 7/2013 | Griffiths et al. |
| 2013/0189700 A1 | 7/2013 | So et al. |
| 2013/0203605 A1 | 8/2013 | Shendure et al. |
| 2013/0203675 A1 | 8/2013 | Desimone et al. |
| 2013/0210639 A1 | 8/2013 | Link et al. |
| 2013/0210991 A1 | 8/2013 | Fonnum et al. |
| 2013/0211055 A1 | 8/2013 | Raines et al. |
| 2013/0225418 A1 | 8/2013 | Watson |
| 2013/0225623 A1 | 8/2013 | Buxbaum et al. |
| 2013/0268206 A1 | 10/2013 | Porreca et al. |
| 2013/0273640 A1 | 10/2013 | Krishnan et al. |
| 2013/0274117 A1 | 10/2013 | Church et al. |
| 2013/0296173 A1 | 11/2013 | Callow et al. |
| 2013/0311106 A1 | 11/2013 | White et al. |
| 2013/0343317 A1 | 12/2013 | Etemad et al. |
| 2013/0344508 A1 | 12/2013 | Schwartz et al. |
| 2014/0030350 A1 | 1/2014 | Ashrafi et al. |
| 2014/0037514 A1 | 2/2014 | Stone et al. |
| 2014/0038178 A1 | 2/2014 | Otto et al. |
| 2014/0057799 A1 | 2/2014 | Johnson et al. |
| 2014/0065234 A1 | 3/2014 | Shum et al. |
| 2014/0080717 A1 | 3/2014 | Li et al. |
| 2014/0093916 A1 | 4/2014 | Belyaev |
| 2014/0120529 A1 | 5/2014 | Andersen et al. |
| 2014/0155274 A1 | 6/2014 | Xie et al. |
| 2014/0155295 A1 | 6/2014 | Hindson et al. |
| 2014/0194323 A1 | 7/2014 | Gillevet et al. |
| 2014/0199730 A1 | 7/2014 | Agresti et al. |
| 2014/0199731 A1 | 7/2014 | Agresti et al. |
| 2014/0200166 A1 | 7/2014 | Van Rooyen et al. |
| 2014/0206073 A1 | 7/2014 | Park et al. |
| 2014/0206554 A1 | 7/2014 | Hindson et al. |
| 2014/0214334 A1 | 7/2014 | Plattner et al. |
| 2014/0221239 A1 | 8/2014 | Carman et al. |
| 2014/0227684 A1 | 8/2014 | Hindson et al. |
| 2014/0227706 A1 | 8/2014 | Kato et al. |
| 2014/0228255 A1 | 8/2014 | Hindson et al. |
| 2014/0235506 A1 | 8/2014 | Hindson et al. |
| 2014/0242664 A1 | 8/2014 | Zhang et al. |
| 2014/0272996 A1 | 9/2014 | Bemis |
| 2014/0274740 A1 | 9/2014 | Srinivasan et al. |
| 2014/0287963 A1 | 9/2014 | Hindson et al. |
| 2014/0302503 A1 | 10/2014 | Lowe et al. |
| 2014/0315725 A1 | 10/2014 | Faham et al. |
| 2014/0315755 A1 | 10/2014 | Chen et al. |
| 2014/0323316 A1 | 10/2014 | Drmanac et al. |
| 2014/0338753 A1 | 11/2014 | Sperling et al. |
| 2014/0357500 A1 | 12/2014 | Vigneault et al. |
| 2014/0357530 A1 | 12/2014 | Zhang et al. |
| 2014/0378322 A1 | 12/2014 | Hindson et al. |
| 2014/0378345 A1 | 12/2014 | Hindson et al. |
| 2014/0378349 A1 | 12/2014 | Hindson et al. |
| 2014/0378350 A1 | 12/2014 | Hindson et al. |
| 2015/0005188 A1 | 1/2015 | Levner et al. |
| 2015/0005199 A1 | 1/2015 | Hindson et al. |
| 2015/0005200 A1 | 1/2015 | Hindson et al. |
| 2015/0011430 A1 | 1/2015 | Saxonov |
| 2015/0011432 A1 | 1/2015 | Saxonov et al. |
| 2015/0031037 A1 | 1/2015 | Li et al. |
| 2015/0057163 A1 | 2/2015 | Rotem et al. |
| 2015/0066385 A1 | 3/2015 | Schnall-Levin et al. |
| 2015/0072899 A1 | 3/2015 | Ward et al. |
| 2015/0111256 A1 | 4/2015 | Church et al. |
| 2015/0111788 A1 | 4/2015 | Fernandez et al. |
| 2015/0119280 A1 | 4/2015 | Srinivas et al. |
| 2015/0133344 A1 | 5/2015 | Shendure et al. |
| 2015/0211056 A1 | 7/2015 | Um et al. |
| 2015/0218633 A1 | 8/2015 | Hindson et al. |
| 2015/0220532 A1 | 8/2015 | Wong |
| 2015/0224466 A1 | 8/2015 | Hindson et al. |
| 2015/0225777 A1 | 8/2015 | Hindson et al. |
| 2015/0225778 A1 | 8/2015 | Hindson et al. |
| 2015/0247182 A1 | 9/2015 | Faham et al. |
| 2015/0258543 A1 | 9/2015 | Baroud et al. |
| 2015/0259736 A1 | 9/2015 | Steemers et al. |
| 2015/0267191 A1 | 9/2015 | Steelman et al. |
| 2015/0267246 A1 | 9/2015 | Baroud et al. |
| 2015/0291942 A1 | 10/2015 | Gloeckner et al. |
| 2015/0292988 A1 | 10/2015 | Bharadwaj et al. |
| 2015/0298091 A1 | 10/2015 | Weitz et al. |
| 2015/0299772 A1 | 10/2015 | Zhang |
| 2015/0299784 A1 | 10/2015 | Fan et al. |
| 2015/0329617 A1 | 11/2015 | Winther et al. |
| 2015/0329852 A1 | 11/2015 | Nolan |
| 2015/0329891 A1 | 11/2015 | Tan et al. |
| 2015/0337298 A1 | 11/2015 | Xi et al. |
| 2015/0353999 A1 | 12/2015 | Agresti et al. |
| 2015/0361418 A1 | 12/2015 | Reed |
| 2015/0368638 A1 | 12/2015 | Steemers et al. |
| 2015/0368694 A1 | 12/2015 | Pan et al. |
| 2015/0376605 A1 | 12/2015 | Jarosz et al. |
| 2015/0376608 A1 | 12/2015 | Kaper et al. |
| 2015/0376609 A1 | 12/2015 | Hindson et al. |
| 2015/0376700 A1 | 12/2015 | Schnall-Levin et al. |
| 2015/0379196 A1 | 12/2015 | Schnall-Levin et al. |
| 2016/0008778 A1 | 1/2016 | Weitz et al. |
| 2016/0024558 A1 | 1/2016 | Hardenbol et al. |

(56) References Cited

U.S. PATENT DOCUMENTS

| | | |
|---|---|---|
| 2016/0024572 A1 | 1/2016 | Shishkin et al. |
| 2016/0025726 A1 | 1/2016 | Altin et al. |
| 2016/0032282 A1 | 2/2016 | Vigneault et al. |
| 2016/0053253 A1 | 2/2016 | Salathia et al. |
| 2016/0059204 A1 | 3/2016 | Hindson et al. |
| 2016/0060621 A1 | 3/2016 | Agresti et al. |
| 2016/0060691 A1 | 3/2016 | Giresi et al. |
| 2016/0115474 A1 | 4/2016 | Jelinek et al. |
| 2016/0122753 A1 | 5/2016 | Mikkelsen et al. |
| 2016/0122817 A1 | 5/2016 | Jarosz et al. |
| 2016/0145683 A1 | 5/2016 | Fan et al. |
| 2016/0153005 A1 | 6/2016 | Zhang et al. |
| 2016/0160235 A1 | 6/2016 | Solodushko et al. |
| 2016/0177359 A1 | 6/2016 | Ukanis et al. |
| 2016/0177375 A1 | 6/2016 | Abate et al. |
| 2016/0194699 A1 | 7/2016 | Borodina et al. |
| 2016/0201125 A1 | 7/2016 | Samuels et al. |
| 2016/0203196 A1 | 7/2016 | Schnall-Levin et al. |
| 2016/0208323 A1 | 7/2016 | Bernstein et al. |
| 2016/0231324 A1 | 8/2016 | Zhao et al. |
| 2016/0232291 A1 | 8/2016 | Kyriazopoulou-Panagiotopoulou et al. |
| 2016/0244742 A1 | 8/2016 | Linnarsson et al. |
| 2016/0244809 A1 | 8/2016 | Belgrader et al. |
| 2016/0244825 A1 | 8/2016 | Vigneault et al. |
| 2016/0251697 A1 | 9/2016 | Nolan |
| 2016/0257984 A1 | 9/2016 | Hardenbol et al. |
| 2016/0281160 A1 | 9/2016 | Jarosz et al. |
| 2016/0289769 A1 | 10/2016 | Schwartz et al. |
| 2016/0304860 A1 | 10/2016 | Hindson et al. |
| 2016/0314242 A1 | 10/2016 | Schnall-Levin et al. |
| 2016/0326583 A1 | 11/2016 | Johnson et al. |
| 2016/0348093 A1 | 12/2016 | Price et al. |
| 2016/0350478 A1 | 12/2016 | Chin et al. |
| 2016/0376663 A1 | 12/2016 | Brown |
| 2017/0009274 A1 | 1/2017 | Abate et al. |
| 2017/0016041 A1 | 1/2017 | Greenfield et al. |
| 2017/0114390 A1 | 4/2017 | Hindson et al. |
| 2017/0128937 A1 | 5/2017 | Hung et al. |
| 2017/0144161 A1 | 5/2017 | Hindson et al. |
| 2017/0145476 A1 | 5/2017 | Ryvkin et al. |
| 2017/0159109 A1 | 6/2017 | Zheng et al. |
| 2017/0183701 A1 | 6/2017 | Agresti et al. |
| 2017/0211127 A1 | 7/2017 | Mikkelsen et al. |
| 2017/0235876 A1 | 8/2017 | Jaffe et al. |
| 2017/0247757 A1 | 8/2017 | Hindson et al. |
| 2017/0260584 A1 | 9/2017 | Zheng et al. |
| 2017/0268056 A1 | 9/2017 | Vigneault et al. |
| 2017/0321252 A1 | 11/2017 | Hindson et al. |
| 2017/0335385 A1 | 11/2017 | Hindson et al. |
| 2017/0342404 A1 | 11/2017 | Hindson et al. |
| 2017/0343545 A1 | 11/2017 | Hadrup et al. |
| 2017/0348691 A1 | 12/2017 | Bharadwaj et al. |
| 2017/0356027 A1 | 12/2017 | Hindson et al. |
| 2017/0362587 A1 | 12/2017 | Hindson et al. |
| 2018/0008984 A1 | 1/2018 | Bharadwaj et al. |
| 2018/0015472 A1 | 1/2018 | Bharadwaj et al. |
| 2018/0015473 A1 | 1/2018 | Bharadwaj et al. |
| 2018/0016634 A1 | 1/2018 | Hindson et al. |
| 2018/0030512 A1 | 2/2018 | Hindson et al. |
| 2018/0030515 A1 | 2/2018 | Regev et al. |
| 2018/0051321 A1 | 2/2018 | Hindson et al. |
| 2018/0057868 A1 | 3/2018 | Walder et al. |
| 2018/0073073 A1 | 3/2018 | Fu et al. |
| 2018/0080021 A1 | 3/2018 | Reuter et al. |
| 2018/0080075 A1 | 3/2018 | Brenner et al. |
| 2018/0087050 A1 | 3/2018 | Zheng et al. |
| 2018/0088112 A1 | 3/2018 | Fan et al. |
| 2018/0094298 A1 | 4/2018 | Hindson et al. |
| 2018/0094312 A1 | 4/2018 | Hindson et al. |
| 2018/0094313 A1 | 4/2018 | Hindson |
| 2018/0094314 A1 | 4/2018 | Hindson et al. |
| 2018/0094315 A1 | 4/2018 | Hindson et al. |
| 2018/0105808 A1 | 4/2018 | Mikkelsen et al. |
| 2018/0112253 A1 | 4/2018 | Hindson et al. |
| 2018/0112266 A1 | 4/2018 | Hindson et al. |
| 2018/0179580 A1 | 6/2018 | Hindson et al. |
| 2018/0179591 A1 | 6/2018 | Belgrader et al. |
| 2018/0180601 A1 | 6/2018 | Pedersen et al. |
| 2018/0195060 A1 | 7/2018 | Wang et al. |
| 2018/0195112 A1 | 7/2018 | Lebofsky et al. |
| 2018/0196781 A1 | 7/2018 | Wong |
| 2018/0216162 A1 | 8/2018 | Belhocine et al. |
| 2018/0237951 A1 | 8/2018 | Bock et al. |
| 2018/0258466 A1 | 9/2018 | Hindson et al. |
| 2018/0258482 A1 | 9/2018 | Hindson et al. |
| 2018/0265928 A1 | 9/2018 | Schnall-Levin et al. |
| 2018/0267036 A1 | 9/2018 | Fan et al. |
| 2018/0273933 A1 | 9/2018 | Gunderson et al. |
| 2018/0274027 A1 | 9/2018 | Hindson et al. |
| 2018/0282804 A1 | 10/2018 | Hindson et al. |
| 2018/0305685 A1 | 10/2018 | Li et al. |
| 2018/0312822 A1 | 11/2018 | Lee et al. |
| 2018/0312873 A1 | 11/2018 | Zheng |
| 2018/0327838 A1 | 11/2018 | Giresi et al. |
| 2018/0327839 A1 | 11/2018 | Hindson et al. |
| 2018/0340169 A1 | 11/2018 | Belhocine et al. |
| 2018/0340170 A1 | 11/2018 | Belhocine et al. |
| 2018/0340171 A1 | 11/2018 | Belhocine et al. |
| 2018/0340172 A1 | 11/2018 | Belhocine et al. |
| 2018/0340939 A1 | 11/2018 | Gaublomme et al. |
| 2018/0346970 A1 | 12/2018 | Chang et al. |
| 2018/0346979 A1 | 12/2018 | Hindson et al. |
| 2018/0363029 A1 | 12/2018 | Hindson et al. |
| 2018/0371540 A1 | 12/2018 | Hindson et al. |
| 2018/0371545 A1 | 12/2018 | Wong et al. |
| 2019/0002967 A1 | 1/2019 | Chen et al. |
| 2019/0024166 A1 | 1/2019 | Hindson et al. |
| 2019/0032129 A1 | 1/2019 | Hindson et al. |
| 2019/0032130 A1 | 1/2019 | Giresi et al. |
| 2019/0040382 A1 | 2/2019 | Steemers et al. |
| 2019/0040464 A1 | 2/2019 | Giresi et al. |
| 2019/0060890 A1 | 2/2019 | Bharadwaj et al. |
| 2019/0060905 A1 | 2/2019 | Bharadwaj et al. |
| 2019/0064173 A1 | 2/2019 | Bharadwaj et al. |
| 2019/0071656 A1 | 3/2019 | Chang et al. |
| 2019/0078150 A1 | 3/2019 | Chen et al. |
| 2019/0085391 A1 | 3/2019 | Hindson et al. |
| 2019/0127731 A1 | 5/2019 | McDermott |
| 2019/0134633 A1 | 5/2019 | Bharadwaj et al. |
| 2019/0136316 A1 | 5/2019 | Hindson et al. |
| 2019/0136317 A1 | 5/2019 | Hindson et al. |
| 2019/0136319 A1 | 5/2019 | Hindson et al. |
| 2019/0153436 A1 | 5/2019 | Belhocine et al. |
| 2019/0153532 A1 | 5/2019 | Bharadwaj et al. |
| 2019/0169700 A1 | 6/2019 | Abate et al. |
| 2019/0176152 A1 | 6/2019 | Bharadwaj et al. |
| 2019/0177789 A1 | 6/2019 | Hindson et al. |
| 2019/0177800 A1 | 6/2019 | Boutet et al. |
| 2019/0203262 A1 | 7/2019 | Hindson et al. |
| 2019/0241965 A1 | 8/2019 | Abate et al. |
| 2019/0276817 A1 | 9/2019 | Hindson et al. |
| 2019/0292593 A1 | 9/2019 | Hindson et al. |
| 2019/0323088 A1 | 10/2019 | Boutet et al. |
| 2019/0330701 A1 | 10/2019 | Abate et al. |
| 2019/0345636 A1 | 11/2019 | McDermott et al. |
| 2019/0352717 A1 | 11/2019 | Schnall-Levin |
| 2019/0367997 A1 | 12/2019 | Bent et al. |
| 2019/0376058 A1 | 12/2019 | Belhocine |
| 2019/0376118 A1 | 12/2019 | Belhocine et al. |
| 2019/0382836 A1 | 12/2019 | Hindson et al. |
| 2020/0005902 A1 | 1/2020 | Mellen et al. |
| 2020/0020417 A1 | 1/2020 | Schnall-Levin et al. |
| 2020/0024596 A1 | 1/2020 | Belhocine et al. |
| 2020/0032335 A1 | 1/2020 | Martinez |
| 2020/0033237 A1 | 1/2020 | Hindson et al. |
| 2020/0033366 A1 | 1/2020 | Alvarado Martinez |
| 2020/0056223 A1 | 2/2020 | Bell |
| 2020/0105373 A1 | 4/2020 | Zheng |
| 2020/0165603 A1 | 5/2020 | Belhocine et al. |
| 2020/0190551 A1 | 6/2020 | Hardenbol et al. |
| 2020/0232027 A1 | 7/2020 | Hindson et al. |
| 2020/0255894 A1 | 8/2020 | Hindson et al. |
| 2020/0263232 A1 | 8/2020 | Bell et al. |

(56) References Cited

U.S. PATENT DOCUMENTS

| | | |
|---|---|---|
| 2020/0291454 A1 | 9/2020 | Belhocine et al. |
| 2020/0291472 A1 | 9/2020 | Hindson et al. |
| 2020/0399631 A1 | 12/2020 | Jarosz et al. |
| 2020/0407775 A1 | 12/2020 | Bharadwaj et al. |
| 2021/0190770 A1 | 6/2021 | Delaney et al. |
| 2021/0270703 A1 | 9/2021 | Abousoud |
| 2022/0162671 A1 | 5/2022 | Pfeiffer et al. |
| 2022/0403375 A1 | 12/2022 | Martinez |
| 2023/0167496 A1 | 6/2023 | Bava |
| 2024/0002914 A1 | 1/2024 | Pfeiffer |

FOREIGN PATENT DOCUMENTS

| | | |
|---|---|---|
| EP | 0249007 A2 | 12/1987 |
| EP | 0271281 A2 | 6/1988 |
| EP | 0637996 B1 | 7/1997 |
| EP | 1019496 B1 | 9/2004 |
| EP | 1672064 A1 | 6/2006 |
| EP | 1482036 B1 | 10/2007 |
| EP | 1841879 A2 | 10/2007 |
| EP | 1944368 A1 | 7/2008 |
| EP | 1594980 B1 | 11/2009 |
| EP | 1967592 B1 | 4/2010 |
| EP | 2258846 A2 | 12/2010 |
| EP | 2145955 B1 | 2/2012 |
| EP | 1905828 B1 | 8/2012 |
| EP | 2136786 B1 | 10/2012 |
| EP | 1908832 B1 | 12/2012 |
| EP | 2540389 A1 | 1/2013 |
| EP | 2635679 A1 | 9/2013 |
| EP | 2752664 A1 | 7/2014 |
| EP | 2635679 B1 | 4/2017 |
| EP | 3013957 B1 | 9/2018 |
| GB | 2097692 A | 11/1982 |
| GB | 2097692 B | 5/1985 |
| GB | 2485850 A | 5/2012 |
| JP | S5949832 A | 3/1984 |
| JP | S60227826 A | 11/1985 |
| JP | 2006507921 A | 3/2006 |
| JP | 2006289250 A | 10/2006 |
| JP | 2007015990 A | 1/2007 |
| JP | 2007268350 A | 10/2007 |
| JP | 2009513948 A | 4/2009 |
| JP | 2009208074 A | 9/2009 |
| JP | 2012131798 A | 7/2012 |
| JP | 2012522517 A | 9/2012 |
| JP | 2014506788 A | 3/2014 |
| RU | 2321638 C2 | 4/2008 |
| WO | WO-84/02000 | 5/1984 |
| WO | WO-9301498 A1 | 1/1993 |
| WO | WO-9418218 A1 | 8/1994 |
| WO | WO-9419101 A1 | 9/1994 |
| WO | WO-9423699 A1 | 10/1994 |
| WO | WO-95/30782 | 11/1995 |
| WO | WO-9629629 A2 | 9/1996 |
| WO | WO-9641011 A1 | 12/1996 |
| WO | WO-9802237 A1 | 1/1998 |
| WO | WO-9852691 A1 | 11/1998 |
| WO | WO-9909217 A1 | 2/1999 |
| WO | WO-9942597 A1 | 8/1999 |
| WO | WO-99/52708 | 10/1999 |
| WO | WO-0008212 A1 | 2/2000 |
| WO | WO-2000008212 A1 | 2/2000 |
| WO | WO-0023181 A1 | 4/2000 |
| WO | WO-0026412 A1 | 5/2000 |
| WO | WO-0034527 A2 | 6/2000 |
| WO | WO-0043766 A1 | 7/2000 |
| WO | WO-0070095 A2 | 11/2000 |
| WO | WO-0102850 A1 | 1/2001 |
| WO | WO-2001002850 A1 | 1/2001 |
| WO | WO-0114589 A2 | 3/2001 |
| WO | WO-0190418 A1 | 11/2001 |
| WO | WO-2001089787 A2 | 11/2001 |
| WO | WO-0127610 A3 | 3/2002 |
| WO | WO-0231203 A2 | 4/2002 |
| WO | WO-02086148 A1 | 10/2002 |
| WO | WO-0218949 A3 | 1/2003 |
| WO | WO-03062462 A2 | 7/2003 |
| WO | WO-2004002627 A2 | 1/2004 |
| WO | WO-2004010106 A2 | 1/2004 |
| WO | WO-2004061083 A2 | 7/2004 |
| WO | WO-2004065617 A2 | 8/2004 |
| WO | WO-2004069849 A2 | 8/2004 |
| WO | WO-2004091763 A2 | 10/2004 |
| WO | WO-2004102204 A1 | 11/2004 |
| WO | WO-2004103565 A2 | 12/2004 |
| WO | WO-2004105734 A1 | 12/2004 |
| WO | WO-2005002730 A1 | 1/2005 |
| WO | WO-2005021151 A1 | 3/2005 |
| WO | WO-2005023331 A2 | 3/2005 |
| WO | WO-2005040406 A1 | 5/2005 |
| WO | WO-2005049787 A9 | 6/2005 |
| WO | WO-2005082098 A2 | 9/2005 |
| WO | WO-2006030993 A1 | 3/2006 |
| WO | WO-2006040551 A2 | 4/2006 |
| WO | WO-2006071770 A2 | 7/2006 |
| WO | WO-2006078841 A1 | 7/2006 |
| WO | WO-2006086210 A2 | 8/2006 |
| WO | WO-2006096571 A2 | 9/2006 |
| WO | WO-2007001448 A2 | 1/2007 |
| WO | WO-2007002490 A2 | 1/2007 |
| WO | WO-2007012638 A1 | 2/2007 |
| WO | WO-2007018601 A1 | 2/2007 |
| WO | WO-2007024840 A2 | 3/2007 |
| WO | WO-2007081385 A2 | 7/2007 |
| WO | WO-2007081387 A1 | 7/2007 |
| WO | WO-2007084192 A2 | 7/2007 |
| WO | WO-2007089541 A2 | 8/2007 |
| WO | WO-2007093819 A2 | 8/2007 |
| WO | WO-2007111937 A1 | 10/2007 |
| WO | WO-2007114794 A1 | 10/2007 |
| WO | WO-2007121489 A2 | 10/2007 |
| WO | WO-2007133710 A2 | 11/2007 |
| WO | WO-2007138178 A2 | 12/2007 |
| WO | WO-2007139766 A2 | 12/2007 |
| WO | WO-2007140015 A2 | 12/2007 |
| WO | WO-2007147079 A2 | 12/2007 |
| WO | WO-2007149432 A2 | 12/2007 |
| WO | WO-2008021123 A1 | 2/2008 |
| WO | WO-2008091792 A2 | 7/2008 |
| WO | WO-2008102057 A1 | 8/2008 |
| WO | WO-2008109176 A2 | 9/2008 |
| WO | WO-2008121342 A2 | 10/2008 |
| WO | WO-2008061193 A2 | 11/2008 |
| WO | WO-2008134153 A1 | 11/2008 |
| WO | WO-2008150432 A1 | 12/2008 |
| WO | WO-2009005680 A1 | 1/2009 |
| WO | WO-2009011808 A1 | 1/2009 |
| WO | WO-2009015296 A1 | 1/2009 |
| WO | WO-2009023821 A1 | 2/2009 |
| WO | WO-2009048532 A2 | 4/2009 |
| WO | WO-2009061372 A2 | 5/2009 |
| WO | WO-2009085215 A1 | 7/2009 |
| WO | WO-2009147386 A1 | 12/2009 |
| WO | WO-2009152928 A2 | 12/2009 |
| WO | WO-2010004018 A2 | 1/2010 |
| WO | WO-2010009735 A2 | 1/2010 |
| WO | WO-2010033200 A2 | 3/2010 |
| WO | WO-2010048605 A1 | 4/2010 |
| WO | WO-2010104604 A1 | 9/2010 |
| WO | WO-2010115154 A1 | 10/2010 |
| WO | WO-2010117620 A2 | 10/2010 |
| WO | WO-2010127304 A2 | 11/2010 |
| WO | WO-2010148039 A2 | 12/2010 |
| WO | WO-2010151776 A2 | 12/2010 |
| WO | WO-2011028539 A1 | 3/2011 |
| WO | WO-2011047870 A1 | 4/2011 |
| WO | WO-2011056546 A1 | 5/2011 |
| WO | WO-2011066476 A1 | 6/2011 |
| WO | WO-2011074960 A1 | 6/2011 |
| WO | WO-2011106314 A2 | 9/2011 |
| WO | WO-2011140510 A2 | 11/2011 |
| WO | WO-2011140627 A1 | 11/2011 |
| WO | WO-2011156529 A2 | 12/2011 |

(56) References Cited

FOREIGN PATENT DOCUMENTS

| | | |
|---|---|---|
| WO | WO-2012012037 A1 | 1/2012 |
| WO | WO-2012047889 A2 | 4/2012 |
| WO | WO-2012048340 A2 | 4/2012 |
| WO | WO-2012048341 A1 | 4/2012 |
| WO | WO-2012055929 A1 | 5/2012 |
| WO | WO-2012061832 A1 | 5/2012 |
| WO | WO-2012083225 A2 | 6/2012 |
| WO | WO-2012087736 A1 | 6/2012 |
| WO | WO-2012100216 A2 | 7/2012 |
| WO | WO-2012106546 A2 | 8/2012 |
| WO | WO-2012112804 A1 | 8/2012 |
| WO | WO-2012112970 A2 | 8/2012 |
| WO | WO-2012116331 A2 | 8/2012 |
| WO | WO-2012136734 A1 | 10/2012 |
| WO | WO-2012142531 A2 | 10/2012 |
| WO | WO-2012142611 A2 | 10/2012 |
| WO | WO-2012148497 A2 | 11/2012 |
| WO | WO-2012149042 A2 | 11/2012 |
| WO | WO-2012150317 A1 | 11/2012 |
| WO | WO-2012166425 A2 | 12/2012 |
| WO | WO-2012167142 A2 | 12/2012 |
| WO | WO-2013019751 A1 | 2/2013 |
| WO | WO-2013035114 A1 | 3/2013 |
| WO | WO-2013036929 A1 | 3/2013 |
| WO | WO-2013055955 A1 | 4/2013 |
| WO | WO-2013096643 A1 | 6/2013 |
| WO | WO-2013122996 A1 | 8/2013 |
| WO | WO-2013123125 A1 | 8/2013 |
| WO | WO-2013126741 A1 | 8/2013 |
| WO | WO-2013134261 A1 | 9/2013 |
| WO | WO-2013150083 A1 | 10/2013 |
| WO | WO-2013177220 A1 | 11/2013 |
| WO | WO-2013188872 A1 | 12/2013 |
| WO | WO-2014018460 A1 | 1/2014 |
| WO | WO-2014028378 A2 | 2/2014 |
| WO | WO-2014028537 A1 | 2/2014 |
| WO | WO-2014053854 A1 | 4/2014 |
| WO | WO-2014071361 A1 | 5/2014 |
| WO | WO-2014072703 A1 | 5/2014 |
| WO | WO-2014074611 A1 | 5/2014 |
| WO | WO-2014093676 A1 | 6/2014 |
| WO | WO-2014108810 A2 | 7/2014 |
| WO | WO-2014140309 A1 | 9/2014 |
| WO | WO-2014144495 A1 | 9/2014 |
| WO | WO-2014145047 A1 | 9/2014 |
| WO | WO-2014150931 A1 | 9/2014 |
| WO | WO-2014165559 A2 | 10/2014 |
| WO | WO-2014182835 A1 | 11/2014 |
| WO | WO-2014189957 A2 | 11/2014 |
| WO | WO-2014200767 A1 | 12/2014 |
| WO | WO-2014210353 A2 | 12/2014 |
| WO | WO-2015015199 A2 | 2/2015 |
| WO | WO-2015031691 A1 | 3/2015 |
| WO | WO-2015044428 A1 | 4/2015 |
| WO | WO-2015157567 A1 | 10/2015 |
| WO | WO-2015164212 A1 | 10/2015 |
| WO | WO-2015185067 A1 | 12/2015 |
| WO | WO-2015188839 A2 | 12/2015 |
| WO | WO-2015200869 A1 | 12/2015 |
| WO | WO-2015200891 A1 | 12/2015 |
| WO | WO-2015200893 A2 | 12/2015 |
| WO | WO-2016040476 A1 | 3/2016 |
| WO | WO-2016033251 A3 | 4/2016 |
| WO | WO-2016061517 A2 | 4/2016 |
| WO | WO-2016100976 A2 | 6/2016 |
| WO | WO-2016126871 A2 | 8/2016 |
| WO | WO-2016130578 A1 | 8/2016 |
| WO | WO-2016138496 A1 | 9/2016 |
| WO | WO-2016149661 A1 | 9/2016 |
| WO | WO-2016168584 A1 | 10/2016 |
| WO | WO-2016170126 A1 | 10/2016 |
| WO | WO-2016187256 A2 | 11/2016 |
| WO | WO-2016187717 A1 | 12/2016 |
| WO | WO-2016191618 A1 | 12/2016 |
| WO | WO-2016207647 A1 | 12/2016 |
| WO | WO-2016207653 A1 | 12/2016 |
| WO | WO-2016207661 A1 | 12/2016 |
| WO | WO-2017015075 A1 | 1/2017 |
| WO | WO-2017025594 A1 | 2/2017 |
| WO | WO-2017034970 A1 | 3/2017 |
| WO | WO-2017053905 A1 | 3/2017 |
| WO | WO-2017066231 A1 | 4/2017 |
| WO | WO-2017075265 A1 | 5/2017 |
| WO | WO-2017075294 A1 | 5/2017 |
| WO | WO-2017079593 A1 | 5/2017 |
| WO | WO-2017096158 A1 | 6/2017 |
| WO | WO-2017117358 A1 | 7/2017 |
| WO | WO-2017151828 A1 | 9/2017 |
| WO | WO-2017156336 A1 | 9/2017 |
| WO | WO-2017180949 A1 | 10/2017 |
| WO | WO-2017184707 A1 | 10/2017 |
| WO | WO-2017197343 A2 | 11/2017 |
| WO | WO-2018031631 A1 | 2/2018 |
| WO | WO-2018039338 A1 | 3/2018 |
| WO | WO-2018039969 A1 | 3/2018 |
| WO | WO-2018045186 A1 | 3/2018 |
| WO | WO-2018058073 A2 | 3/2018 |
| WO | WO-2018091676 A1 | 5/2018 |
| WO | WO-2018103025 A1 | 6/2018 |
| WO | WO-2018119301 A1 | 6/2018 |
| WO | WO-2018119447 A2 | 6/2018 |
| WO | WO-2018125982 A1 | 7/2018 |
| WO | WO-2018129368 A2 | 7/2018 |
| WO | WO-2018132635 A1 | 7/2018 |
| WO | WO-2018172726 A1 | 9/2018 |
| WO | WO-2018174827 A1 | 9/2018 |
| WO | WO-2018191701 A1 | 10/2018 |
| WO | WO-2018213643 A1 | 11/2018 |
| WO | WO-2018226546 A1 | 12/2018 |
| WO | WO-2018236615 A1 | 12/2018 |
| WO | WO-2018237209 A1 | 12/2018 |
| WO | WO-2019028166 A1 | 2/2019 |
| WO | WO-2019040637 A1 | 2/2019 |
| WO | WO-2019083852 A1 | 5/2019 |
| WO | WO-2019084043 A1 | 5/2019 |
| WO | WO-2019084165 A1 | 5/2019 |
| WO | WO-2019084328 A1 | 5/2019 |
| WO | WO-2019099751 A1 | 5/2019 |
| WO | WO-2019108851 A1 | 6/2019 |
| WO | WO-2019113235 A1 | 6/2019 |
| WO | WO-2019118355 A1 | 6/2019 |
| WO | WO-2019126789 A1 | 6/2019 |
| WO | WO-2019148042 A1 | 8/2019 |
| WO | WO-2019152108 A1 | 8/2019 |
| WO | WO-2019157529 A1 | 8/2019 |
| WO | WO-2019165318 A1 | 8/2019 |
| WO | WO-2019169028 A1 | 9/2019 |
| WO | WO-2019169347 A1 | 9/2019 |
| WO | WO-2019191321 A1 | 10/2019 |
| WO | WO-2019217758 A1 | 11/2019 |
| WO | WO-2020028882 A1 | 2/2020 |
| WO | WO-2020041148 A1 | 2/2020 |
| WO | WO-2020142779 A1 | 7/2020 |
| WO | WO-2020167862 A1 | 8/2020 |
| WO | WO-2020167866 A1 | 8/2020 |
| WO | WO-2020168013 A1 | 8/2020 |
| WO | WO-2020198532 A1 | 10/2020 |
| WO | WO-2021046475 A1 | 3/2021 |
| WO | WO-2021133845 A1 | 7/2021 |
| WO | WO-2021207610 A1 | 10/2021 |
| WO | WO-2021212042 A1 | 10/2021 |
| WO | WO-2021/222302 A1 | 11/2021 |
| WO | WO-2021222301 A1 | 11/2021 |
| WO | WO-2022103712 A1 | 5/2022 |
| WO | WO-2022182682 A1 | 9/2022 |
| WO | WO-2022182785 A1 | 9/2022 |
| WO | WO-2022271908 A1 | 12/2022 |
| WO | WO-2023076528 A2 | 5/2023 |

OTHER PUBLICATIONS

Co-pending U.S. Appl. No. 17/318,364, inventors Bava; Felice Alessio et al., filed on May 12, 2021.

(56) References Cited

OTHER PUBLICATIONS

Co-pending U.S. Appl. No. 17/512,241, inventors Hill; Andrew John et al., filed on Oct. 27, 2021.
Co-pending U.S. Appl. No. 17/517,408, inventors Salmanzadeh; Alireza et al., filed on Nov. 2, 2021.
Co-pending U.S. Appl. No. 17/518,213, inventor Lund; Paul Eugene, filed on Nov. 3, 2021.
Co-pending U.S. Appl. No. 17/522,741, inventors Zheng; Xinying et al., filed on Nov. 9, 2021.
Co-pending U.S. Appl. No. 17/545,862, inventor Katherine; Pfeiffer, filed on Dec. 8, 2021.
Co-pending U.S. Appl. No. 17/573,350, inventor Corey; M. Nemec, filed on Jan. 11, 2022.
Co-pending U.S. Appl. No. 17/580,947, inventor Gibbons; Michael, filed on Jan. 21, 2022.
Co-pending U.S. Appl. No. 18/046,843, inventor Toh; Mckenzi, filed on Oct. 14, 2022.
Co-pending U.S. Appl. No. 18/152,650, inventor Shastry; Shankar, filed on Jan. 10, 2023.
10X Genomics. 10x Genomics Chromium™ Single Cell 3' Solution Utilized for Perturb-seq Approach. Press Release. Dec. 19, 2016. Retrieved from https://www.10xgenomics.com/news/10x-genomics-chromium-single-cell-3-solution-utilized-perturb-seq-approach/.
Abate, et al. Beating Poisson encapsulation statistics using close-packed ordering. Lab Chip. Sep. 21, 2009;9(18):2628-31. doi: 10.1039/b909386a. Epub Jul. 28, 2009.
Abate, et al. High-throughput injection with microfluidics using picoinjectors. Proc Natl Acad Sci U S A. Nov. 9, 2010;107(45):19163-6. doi: 10.1073/pNas.1006888107. Epub Oct. 20, 2010.
Abate et al., Valve-based flow focusing for drop formation. Appl Phys Lett. 2009;94. 3 pages.
Adamson, et al. A Multiplexed Single-Cell CRISPR Screening Platform Enables Systematic Dissection of the Unfolded Protein Response. Cell. Dec. 15, 2016;167(7):1867-1882.e21. doi: 10.1016/j.cell.2016.11.048.
Adamson et al., "Production of arrays of chemically distinct nanolitre plugs via repeated splitting in microfluidic devices", Lab Chip 6(9): 1178-1186 (Sep. 2006).
Adey, et al. Rapid, low-input, low-bias construction of shotgun fragment libraries by high-density in vitro transposition. Genome Biology 11:R119 (2010).
Adey, et al., "Ultra-low-input, tagmentation-based whole-genome bisulfite sequencing", Genome Research, 2012, 22 ;6): 1139-1143.
Advisory Action mailed Mar. 21, 2014 for U.S. Appl. No. 13/119,470.
Advisory Action mailed May 16, 2014 for U.S. Appl. No. 13/503,588.
Advisory Action mailed Nov. 20, 2013 for U.S. Appl. No. 13/139,326.
Agasti, et al. Photocleavable DNA barcode-antibody conjugates allow sensitive and multiplexed protein analysis in single cells. J Amer Chem Soc ePub, Nov. 2, 2012, vol. 134, No. 45, pp. 18499-18502.
Agresti, et al. Selection of ribozymes that catalyse multiple-turnover Diels-Alder cycloadditions by using in vitro compartmentalization. Proc Natl Acad Sci U S A. Nov. 8, 2005;102(45):16170-5. Epub Oct. 31, 2005.
AH006633.3 (*Homo sapiens* clone P1 and PAC max interactor 1 (MXI1) gene, complete cds, NCBI Reference Sequence, priority to Jun. 10, 2016, 5 pages) (Year:2016).
Ahern, "Biochemical, Reagents Kits Offer Scientists Good Return on Investment" The Scientist (1995) 9(15):1-7.
Ahern, H. The Scientist, vol. 20, pp. 20 and 22. July (Year: 1995).
Ailenberg, et al. (2000) Controlled Hot Start and Improved Specificity in Carrying Out PCR Utilizing Touch-Up and Loop Incorporated Primers (TULIPS). BioTechniques, 29:1018-1024. (Year: 2000).
Aitman, et al. Copy number polymorphism in Fcgr3 predisposes to glomerulonephritis in rats and humans. Nature. Feb. 16, 2006;439(7078):851-5.
Akselband, "Enrichment of slow-growing marine microorganisms from mixed cultures using gel microdrop (GMD) growth assay and fluorescence-activated cell sorting", J. Exp. Marine Bioi., 329: 196-205 (2006).
Akselband, "Rapid mycobacteria drug susceptibility testing using gel microdrop (GMD) growth assay and flow cytometry", J. Microbiol. Methods, 62:181-197 (2005).
Altemos et al., "Genomic Characterization of Large Heterochromatic Gaps in the Human Genome Assembly," PLOS Computational Biology, May 15, 2014, vol. 10, Issue 5, 14 pages.
Amini, S. et al. "Haplotype-resolved whole-genome sequencing by contiguity-preserving transposition and combinatorial indexing" Nature Genetics (2014) 46:1343-1349 doi:10.1038/ng.3119.
Anna et al.: Formation of dispersions using "flow focusing" in microchannels: Applied Physics Letters, vol. 82, No. 3, pp. 364-366 (2003).
Anonymous, "Oligo(dT)25 cellulose beads" NEB (2012) Retrieved from the Internet:https://www.neb.com/~/media/Catalog/All-Products/286CA51268E24DE1B06F1CB288698B54/Datacards%20or%Manuals/S1408Datasheet-Lot0011205.pdf.
Anonymous, "Oligotex Handbook" Qiagen (2012) XP055314680, Retrieved from the Internet: URL:http://www.qiagen.com/de/resources/download.apsx?id=f9fald98-d54d-47e7-a20b-8b0cb8975009&lang=en.
Anonymous: "TCEP=HCI" Thermo Scientific, Dec. 31, 2013 (Dec. 31, 2013), XP055508461, Retrieved from the Internet: URL:https://assets.thermofisher.com/TFS-Assets/LSG/manuals/MAN0011306_TCEP_HCI_UG.pdf.
Anonymous: "Three Ways to Get Intimate with Epigenetic Marks". Oct. 24, 2012. Retrieved from Internet: https://epigenie.com/three-ways-to-get-intimate-with-epigenetic-marks/.
Anonymous: "Viscosity-Basic concepts" (2004) XP055314117, Retrieved from the Internet: URL:http://lhtc.epfl.ch/webdav/site/lhtc/shared/import/migration/2 VISCOSITY.pdf.
Ason et al. DNA sequence bias during Tn5 transposition. Journal of molecular biology 335.5 (2004): 1213-1225.
Attia, et al. Micro-injection moulding of polymer microfluidic devices. Microfluidics and nanofluidics. 2009; 7(1):1-28.
Australian Office Action issued Dec. 17, 2013 for Application No. AU 2010315580.
Balikova, et al. Autosomal-dominant microtia linked to five tandem copies of a copy-number-variable region at chromosome 4p16. Am J Hum Genet. Jan. 2008;82(1):181-7. doi: 10.1016/j.ajhg.2007.08.001.
Banchelli, et al. Phospholipid membranes decorated by cholesterol-based oligonucleotides as soft hybrid nanostructures. J Phys Chem B. Sep. 4, 2008;112(35):10942-52. doi: 10.1021/jp802415t. Epub Aug. 9, 2008.
Bansal et al. "An MCMC algorithm for haplotype assembly from whole-genome sequence data," (2008) Genome Res 18:1336-1346.
Bansal et al. "HapCUT: an efficient and accurate algorithm for the haplotype assembly problem," Bioinformatics (2008) 24:i153-i159.
Baret, et al. Fluorescence-activated droplet sorting (FADS): efficient microfluidic cell sorting based on enzymatic activity. Lab Chip. Jul. 7, 2009;9(13):1850-8. doi: 10.1039/b902504a. Epub Apr. 23, 2009.
BD. BD Rhapsody ™ Single-Cell Analysis System: Analyze hundreds of genes across tens of thousands of single cells in parallel. BD, Becton, Dickinson and Company. BDGM1012 Rev. 1. 2017. 8 pages.
Bedtools: General Usage, http://bedtools.readthedocs.io/en/latest/content/generalusage.html; Retrieved from the Internet Jul. 8, 2016.
Bentley, et al. 2008. Supplementary Information. pp. 1-55 Nature. Nov. 6, 2008; 456(7218):53-9.
Bentley et al. "Accurate whole human genome sequencing using reversible terminator chemistry," (2008) Nature 456:53-59.
Bentolila, et al. Single-step multicolor fluorescence in situ hybridization using semiconductor quantum dot-DNA conjugates. Cell Biochem Biophys. 2006;45(1):59-70.
Bentzen, et al. Large-scale detection of antigen-specific T cells using peptide-MHC-I multimers labeled with DNA barcodes. Nat Biotechnol. Oct. 2016;34(10):1037-1045. doi: 10.1038/nbt.3662. Epub Aug. 29, 2016.
Berkum, et al. Hi-C: a method to study the three-dimensional architecture of genomes. J Vis Exp. May 6, 2010;(39). pii: 1869. doi: 10.3791/1869.

(56) References Cited

OTHER PUBLICATIONS

Biles et al., Low-fidelity Pyrococcus furiosis DNA polymerase mutants useful in error-prone PCR. Nucl. Acids Res. 32(22):e176 2004.

Bjornsson et al., Intra-individual change over time in DNA methylation with familial clustering, JAMA, Jun. 25, 2008, vol. 299 No. 24, pp. 2877-2883.

Bodi, K. et al. "Comparison of Commercially Available Target Enrichment Methods for Next-Generation Sequencing" J Biomolecular Techniques (2013) 24:73-86.

Boone, et al. Plastic advances microfluidic devices. The devices debuted in silicon and glass, but plastic fabrication may make them hugely successful in biotechnology application. Analytical Chemistry. Feb. 2002; 78A-86A.

Boulanger, et al, "Massively parallel haplotyping on microscopic beads for the high-throughput phase analysis of single molecules", PLoS One, vol. 7:1-10, 2012.

Boyle, et al. "High-resolution genome-wide in vivo footprinting of diverse transcription factors in human cells", Genome Res. Mar. 2011;21(3):456-64.

Braeckmans et al., Scanning the Code. Modern Drug Discovery. 2003:28-32.

Bransky, et al. A microfluidic droplet generator based on a piezoelectric actuator. Lab Chip. Feb. 21, 2009;9(4):516-20. doi: 10.1039/b814810d. Epub Nov. 20, 2008.

Bray, "The JavaScript Object Notation (JSON) Data Interchange Format," Mar. 2014, retrieved from the Internet Feb. 15, 2015; https://tools.ietf.org/html/rfc7159.

Brenner, et al. In vitro cloning of complex mixtures of DNA on microbeads: physical separation of differentially expressed cDNAs. Proc Natl Acad Sci U S A. Feb. 15, 2000;97(4):1665-70.

Briggs, et al. "Tumor-infiltrating immune repertoires captures by single-cell barcoding in emulsion" with Supplementary material. bioRxiv 134841; doi: https://doi.org/10.1101/134841. Posted May 5, 2017.

Brouzes, et al. Droplet microfluidic technology for single-cell high-throughput screening. Proc Natl Acad Sci U S A. Aug. 25, 2009;106(34):14195-200. doi: 10.1073/pnas.0903542106. Epub Jul. 15, 2009.

Brown, K., Targeted Sequencing Using Droplet-Based Microfluidics, RainDance Technologies, 2009, 1-18.

Browning, et al. Haplotype phasing: existing methods and new developments. Nat Rev Genet. Sep. 16, 2011;12(10):703-14. doi: 10.1038/nrg3054. Review.

Browning, S.R. et al. "Haplotype Phasing: Existing Methods and New Developments" NaRevGenet (Sep. 16, 2011) 12(10):703-714.

Buchman GW, et al. Selective RNA amplification: a novel method using dUMP-containing primers and uracil DNA glycosylase. PCR Methods Appl. Aug. 1993; 3(1):28-31.

Buenrostro, et al. ATAC-seq: A Method for Assaying Chromatin Accessibility Genome-Wide. Curr Protoc Mol Biol. Jan. 5, 2015;109: 21.29.1-21.29.9. doi:10.1002/0471142727.mb2129s109.

Buenrostro, et al. Single-cell chromatin accessibility reveals principles of regulatory variation. Nature. Jul. 23, 2015;523(7561):486-90. doi: 10.1038/nature14590. Epub Jun. 17, 2015.

Buenrostro, et al., "Tranposition of native chromatin for fast and sensitive epigenomic profiling of open chromatin, DNA-binding proteins and nucleosome position", Nature Methods, 2013, 10(12): 1213-1218.

Buenrostro, et al. "Transposition of native chromatin for fast and sensitive epigenomic profiling of open chromatin, DNA-binding proteins and nucleosome position." Nat Methods. Dec. 2013;10(12):1213-8. doi: 10.1038/nmeth.2688. Epub Oct. 6, 2013.

Burns, et al. An Integrated Nanoliter DNA Analysis Device. Science. Oct. 16, 1998;282(5388):484-7.

Burns, et al. Microfabricated structures for integrated DNA analysis. Proc Natl Acad Sci U S A. May 28, 1996; 93(11): 5556-5561.

Burns, et al. The intensification of rapid reactions in multiphase systems using slug flow in capillaries. Lab Chip. Sep. 2001;1(1):10-15. Epub Aug. 9, 2001.

Bystrykh, et al. Generalized DNA barcode design based on Hamming codes. PLoS One. 2012;7(5):e36852. doi: 10.1371/journal.pone.0036852. Epub May 17, 2012.

Cappuzzo, et al. Increased HER2 gene copy number is associated with response to gefitinib therapy in epidermal growth factor receptor-positive non-small-cell lung cancer patients. J Clin Oncol. Aug. 1, 2005;23(22):5007-18.

Carroll, "The selection of high-producing cell lines using flow cytometry and cell sorting", Exp. Op. Bioi. Therp., 4:11 1821-1829 (2004).

Caruccio, et al. Nextera Technology for NGS DNA Library Preparation: Simultaneous Fragmentation and Tagging by In Vitro Transposition, Nextera Technology, 2009, 16-3. (Year: 2009).

Caruccio N., Preparation of Next-Generation Sequencing Libraries Using Nextera Technology: Simultaneous DNA Fragmentation and Adaptor Tagging by In Vitro Transposition. Ch. 17 Methods in Microbiology 733:241-55 (2011).

Casbon, et al, "Reflex: intramolecular barcoding of long-range PCR products for sequencing multiple pooled DNAs", Nucleic Acids Res., pp. 1-6, 2013.

Cejas, P. et al. "Chromatin immunoprecipitation from fixed clinical tissues reveals tumor-specific enhancer profiles" Nature Med (2016) 22(6):685-691.

Chang et al. Droplet-based microfluidic platform for heterogeneous enzymatic assays, 2013, Lab Chip, 13, 1817-1822 (Year: 2013).

Chaudhary "A rapid method of cloning functional variable-region antibody genes in *Escherichia coli* as single-chain immunotoxins" Proc. Natl. Acad. Sci USA 87: 1066-1070 (Feb. 1990).

Chechetkin et al., Sequencing by hybridization with the generic 6-mer oligonucleotide microarray: an advanced scheme for data processing. J Biomol Struct Dyn. Aug. 2000;18(1):83-101.

Chen et al. BreakDancer: an algorithm for high-resolution mapping of genomic structural variation. Nature Methods (2009) 6(9):677-681.

Chen, et al. Chemical transfection of cells in picoliter aqueous droplets in fluorocarbon oil. Anal Chem. Nov. 15, 2011;83(22):8816-20. doi: 10.1021/ac2022794. Epub Oct. 17, 2011.

Chinese Office Action and search report mailed May 23, 2013 for Application No. CN 200880127116.4.

Choi et al. "Identification of novel isoforms of the EML4-ALK transforming gene in non–small cell lung cancer," Cancer Res (2008) 68:4971-4976.

Choi, et al. Identification of novel isoforms of the EML4-ALK transforming gene in non-small cell lung cancer. Cancer Res. Jul. 1, 2008;68(13):4971-6. doi: 10.1158/0008-5472.CAN-07-6158.

Chokkalingam, et al. Probing cellular heterogeneity in cytokine-secreting immune cells using droplet-based microfluidics. Lab Chip. Dec. 21, 2013;13(24):4740-4. doi: 10.1039/c3lc50945a.

Chou, et al. Disposable Microdevices for DNA Analysis and Cell Sorting. Proc. Solid-State Sensor and Actuator Workshop, Hilton Head, SC. Jun. 8-11, 1998; 11-14.

Christian, et al. Targeting DNA double-strand breaks with TAL effector nucleases. Genetics.186 (2010): 757-761.

Christiansen et al. "The Covalent Eukaryotic Topoisomerase I-DNA Intermediate Catalyzes pH-dependent Hydrolysis and Alcoholysis" J Biol Chem (Apr. 14, 1994) 269(15):11367-11373.

Chu, et al. Controllable monodisperse multiple emulsions. Angew Chem Int Ed Engl. 2007;46(47):8970-4.

Chung, et al. Structural and molecular interrogation of intact biological systems. Nature. May 16, 2013;497(7449):332-7. doi: 10.1038/nature12107. Epub Apr. 10, 2013.

Clark, et al. Single-cell epigenomics: powerful new methods for understanding gene regulation and cell identity. Genome Biol. Apr. 18, 2016;17:72. doi: 10.1186/s13059-016-0944-x.

Clausell-Tormos et al., "Droplet-based microfluidic platforms for the encapsulation and screening of mammalian cells and multicellular organisms", Chem. Biol. 15:427-437 (2008).

Cleary et al. "Joint variant and de novo mutation identification on pedigrees from highthroughput sequencing data,"J Comput Biol (2014) 21:405-419.

Cong et al. Multiplex genome engineering using CRISPR/Cas systems. Science 339(6121):819-23 (2013).

(56) References Cited

OTHER PUBLICATIONS

Cook, et al. Copy-number variations associated with neuropsychiatric conditions. Nature. Oct. 1, 20086;455(7215):919-23. doi: 10.1038/nature07458.
Co-pending U.S. Appl. No. 15/200,928, inventors Hindson; Benjamin et al., filed on Jul. 1, 2016.
Co-pending U.S. Appl. No. 15/242,256, inventor Jaffe; David, filed on Aug. 19, 2016.
Co-pending U.S. Appl. No. 15/355,542, inventors Schnall-Levin; Michael et al., filed on Nov. 18, 2016.
Co-pending U.S. Appl. No. 15/392,557, inventors Hindson; Benjamin et al., filed on Dec. 28, 2016.
Co-pending U.S. Appl. No. 15/430,298, inventors Zheng; Xinying et al., filed on Feb. 10, 2017.
Co-pending U.S. Appl. No. 15/440,772, inventors Hindson; Benjamin J et al., filed on Feb. 23, 2017.
Co-pending U.S. Appl. No. 15/449,741, inventors Hindson; Benjamin et al., filed on Mar. 3, 2017.
Co-pending U.S. Appl. No. 15/470,814, inventors Hindson; Benjamin et al., filed on Mar. 27, 2017.
Co-pending U.S. Appl. No. 15/588,519, inventors Hindson; Benjamin et al., filed on May 5, 2017.
Co-pending U.S. Appl. No. 15/596,754, inventors Bharadwaj; Rajiv et al., filed on May 16, 2017.
Co-pending U.S. Appl. No. 15/598,898, inventor Hindson; Benjamin, filed on May 18, 2017.
Co-pending U.S. Appl. No. 15/687,357, inventors Hindson; Benjamin et al., filed on Aug. 25, 2017.
Co-pending U.S. Appl. No. 15/693,374, inventors Hindson; Benjamin et al., filed on Aug. 31, 2017.
Co-pending U.S. Appl. No. 15/720,085, inventor Belgrader; Phillip, filed on Sep. 29, 2017.
Co-pending U.S. Appl. No. 15/730,119, inventor Wong; Alexander Y., filed on Oct. 11, 2017.
Co-pending U.S. Appl. No. 15/842,550, inventors Belhocine; Kamila et al., filed on Dec. 14, 2017.
Co-pending U.S. Appl. No. 15/842,687, inventors Belhocine; Kamila et al., filed on Dec. 14, 2017.
Co-pending U.S. Appl. No. 15/842,713, inventors Belhocine; Kamila et al., filed on Dec. 14, 2017.
Co-pending U.S. Appl. No. 15/847,659, inventors Hindson; Benjamin et al., filed on Dec. 19, 2017.
Co-pending U.S. Appl. No. 15/848,714, inventors Belhocine; Kamila et al., filed on Dec. 20, 2017.
Co-pending U.S. Appl. No. 15/850,241, inventor Hindson; Benjamin, filed on Dec. 21, 2017.
Co-pending U.S. Appl. No. 15/872,499, inventor Hindson; Benjamin, filed on Jan. 16, 2018.
Co-pending U.S. Appl. No. 15/875,899, inventor Belgrader; Phillip, filed on Jan. 19, 2018.
Co-pending U.S. Appl. No. 15/887,711, inventors Hindson; Benjamin et al., filed on Feb. 2, 2018.
Co-pending U.S. Appl. No. 15/887,947, inventors Belhocine; Kamila et al., filed on Feb. 2, 2018.
Co-pending U.S. Appl. No. 15/933,299, inventors Belgrader; Phillip et al., filed on Mar. 22, 2018.
Co-pending U.S. Appl. No. 16/000,803, inventor Hindson; Benjamin, filed on Jun. 5, 2018.
Co-pending U.S. Appl. No. 16/033,065, inventors Giresi; Paul et al., filed on Jul. 11, 2018.
Co-pending U.S. Appl. No. 16/043,874, inventors Giresi; Paul et al., filed on Jul. 24, 2018.
Co-pending U.S. Appl. No. 16/045,474, inventors Hindson; Benjamin, filed on Jul. 25, 2018.
Co-pending U.S. Appl. No. 16/052,431, inventor Hindson; Benjamin, filed on Aug. 1, 2018.
Co-pending U.S. Appl. No. 16/052,486, inventors Hindson; Benjamin et al., filed on Aug. 1, 2018.
Co-pending U.S. Appl. No. 16/056,231, inventor Hindson; Benjamin, filed on Aug. 6, 2018.
Co-pending U.S. Appl. No. 16/138,448, inventor Hindson; Benjamin, filed on Sep. 21, 2018.
Co-pending U.S. Appl. No. 16/144,832, inventor Hindson; Benjamin, filed on Sep. 27, 2018.
Co-pending U.S. Appl. No. 16/160,576, inventors Giresi; Paul et al., filed on Oct. 15, 2018.
Co-pending U.S. Appl. No. 16/160,719, inventors Giresi; Paul et al., filed on Oct. 15, 2018.
Co-pending U.S. Appl. No. 16/165,389, inventors Hindson; Benjamin et al., filed on Oct. 19, 2018.
Co-pending U.S. Appl. No. 16/196,684, inventor McDermott; Geoffrey, filed on Nov. 20, 2018.
Co-pending U.S. Appl. No. 16/206, 168, inventor Belhocine; Kamila, filed on Nov. 30, 2018.
Co-pending U.S. Appl. No. 16/212,441, inventor Hindson; Benjamin, filed on Dec. 6, 2018.
Co-pending U.S. Appl. No. 16/228,261, inventor Bharadwaj; Rajiv, filed on Dec. 20, 2018.
Co-pending U.S. Appl. No. 16/228,362, inventor Hardenbol; Paul, filed on Dec. 20, 2018.
Co-pending U.S. Appl. No. 16/230,936, inventor Bent; Zachary, filed on Dec. 21, 2018.
Co-pending U.S. Appl. No. 16/231,142, inventor Hindson; Benjamin, filed on Dec. 21, 2018.
Co-pending U.S. Appl. No. 16/231, 185, inventor Hindson; Benjamin, filed on Dec. 21, 2018.
Co-pending U.S. Appl. No. 16/249,688, inventor Hindson; Benjamin, filed on Jan. 16, 2019.
Co-pending U.S. Appl. No. 16/294,769, inventor Hindson; Benjamin, filed on Mar. 6, 2019.
Co-pending U.S. Appl. No. 16/419,555, inventor Belhocine; Kamila, filed on May 22, 2019.
Co-pending U.S. Appl. No. 16/419,820, inventor Bharadwaj; Rajiv, filed on May 22, 2019.
Co-pending U.S. Appl. No. 16/435,362, inventors Hindson; Christopher et al., filed on Jun. 7, 2019.
Coufal, et al. L1 retrotransposition in human neural progenitor cells. Nature. Aug. 27, 2009;460(7259):1127-31. doi: 10.1038/nature08248. Epub Aug. 5, 2009.
Curcio. Improved Techniques for High-Throughput Molecular Diagnostics. PhD Thesis. 2002.
Cusanovich, et al. Supplementary materials for Multiplex single-cell profiling of chromatin accessibility by combinatorial cellular indexing. Science. May 22, 2015;348(6237):910-4. doi: 10.1126/science.aab1601. Epub May 7, 2015.
Cusanovich, et al. Multiplex single-cell profiling of chromatin accessibility by combinatorial cellular indexing. Science, May 22, 2015;348(6237):910-14.
Damean, et al. Simultaneous measurement of reactions in microdroplets filled by concentration gradients. Lab Chip. Jun. 21, 2009;9(12):1707-13. doi: 10.1039/b821021g. Epub Mar. 19, 2009.
Dangla, et al. Droplet microfluidics driven by gradients of confinement. Proc Natl Acad Sci U S A. Jan. 15, 2013; 110(3): 853-858. Published online Jan. 2, 2013. doi: 10.1073/pnas.1209186110.
De Bruin et al., UBS Investment Research. Q-Series®: DNA Sequencing. UBS Securities LLC. Jul. 12, 2007. 15 pages.
Definition of "corresponding", Merriam-Webster Online, downloaded from http://www.merriam-webster.com/dictionary/corresponding (Year: 2019).
Dekker, et al. Capturing chromosome conformation. Science. Feb. 15, 2002;295(5558):1306-11.
Delehanty, et al. Peptides for specific intracellular delivery and targeting of nanoparticles: implications for developing nanoparticle-mediated drug delivery. Ther Deliv. Sep. 2010;1(3):411-33.
Demirci, et al. Single cell epitaxy by acoustic picolitre droplets. Lab Chip. Sep. 2007;7(9):1139-45. Epub Jul. 10, 2007.
Depristo et al. A framework for variation discovery and genotyping using next-generation DNA sequencing data. Nature Genet 43:491-498 (2011).
Dey, et al. Integrated Genome and Transcriptome Sequencing from the Same Cell. Nature biotechnology 33.3 (2015): 285-289. PMC. Web. Dec. 18, 2017.

(56) References Cited

OTHER PUBLICATIONS

Dhingra, et al. A complete solution for high throughput single cell targeted multiomic DNA and RNA sequencing for cancer research. Poster. AACR 2019.

Dixit, et al. Perturb-Seq: Dissecting Molecular Circuits with Scalable Single-Cell RNA Profiling of Pooled Genetic Screens. Cell. Dec. 15, 2016;167(7):1853-1866.e17. doi: 10.1016/j.cell.2016.11.038.

Doerr, "The smallest bioreactor", Nature Methods, 2:5 326 (2005).

Doshi, et al. Red blood cell-mimicking synthetic biomaterial particles. Proceedings of the National Academy of Sciences 106.51 (2009): 21495-21499.

Dowding, et al. Oil core/polymer shell microcapsules by internal phase separation from emulsion droplets. II: controlling the release profile of active molecules. Langmuir. Jun. 7, 2005;21(12):5278-84.

Draper, et al. Compartmentalization of electrophoretically separated analytes in a multiphase microfluidic platform. Anal Chem. Jul. 3, 2012;84(13):5801-8. doi: 10.1021/ac301141x. Epub Jun. 13, 2012.

Dressler, et al. Droplet-based microfluidics enabling impact on drug discovery. J Biomol Screen. Apr. 2014;19(4):483-96. doi: 10.1177/1087057113510401. Epub Nov. 15, 2013.

Dressman et al. Supplementary Information pp. 1-2 of article published 2003, PNAS 100(15:8817-22).

Dressman et al. Transforming single DNA molecules into fluorescent magnetic particles for detection and enumeration of genetic variations. Proc. Natl. Acad. Sci. 2003. 100(15):8817-8822.

Drmanac et al., Sequencing by hybridization (SBH): advantages, achievements, and opportunities. Adv Biochem Eng Biotechnol. 2002;77 :75-101.

Droplet Based Sequencing (slides) dated (Mar. 12, 2008).

Eastburn, et al. Ultrahigh-throughput mammalian single-cell reverse-transcriptase polymerase chain reaction in microfluidic droplets. Anal Chem. Aug. 20, 2013;85(16):8016-21. doi: 10.1021/ac402057q. Epub Aug. 8, 2013.

Eid, et al. Real-time DNA sequencing from single polymerase molecules. Science. Jan. 2, 2009;323(5910):133-8. doi: 10.1126/science.1162986. Epub Nov. 20, 2008.

Ekblom, R. et al. "A field guide to whole-genome sequencing, assembly and annotation" Evolutionary Apps (Jun. 24, 2014) 7(9):1026-1042.

Epicenter, EZ-Tn5 Transposase, Epicenter, 2012, 1-5. (Year: 2012).

Epicentre., "EZ-Tn5TM Custom Transposome Construction Kits", http://www.epicentre.com, pp. 1-17, 2012.

Esser-Kahn, et al. Triggered release from polymer capsules. Macromolecules. 2011; 44:5539-5553.

European office action dated Dec. 15, 2010 for EP Application No., 08865992.5.

European search report and opinion dated Feb. 2, 2016 for EP Application No. 13829413.

European search report and opinion dated Jul. 25, 2016 for EP Application No. 13862194.1.

European search report and opinion dated Jul. 25, 2016 for EP Application No. 14748569.2.

European search report and opinion dated Jul. 25, 2016 for EP Application No. 14817610.

European search report and opinion dated Jul. 26, 2016 for EP Application No. 14749595.6.

Fabi, et al. Correlation of efficacy between EGFR gene copy number and lapatinib/capecitabine therapy in HER2-positive metastatic breast cancer. J. Clin. Oncol. 2010; 28:15S. 2010 ASCO Meeting abstract Jun. 14, 2010:1059.

Fan, et al. Noninvasive diagnosis of fetal aneuploidy by shotgun sequencing DNA from maternal blood. Proc Natl Acad Sci U S A. Oct. 21, 2008;105(42):16266-71. Epub Oct. 6, 2008.

Fan, et al. Whole-genome molecular haplotyping of single cells. Nature Biotechnology, vol. 29, No. 1. Jan. 1, 2011. pp. 51-59.

Fang, et al. Fluoride-cleavable biotinylation phosphoramidite for 5'-end-labeling and affinity purification of synthetic oligonucleotides. Nucleic Acids Res. Jan. 15, 2003;31(2):708-15.

Fanielli, M. et al. "Pathology tissue-chromatin immunoprecipitation, coupled with high-throughput sequencing, allows the epigenetic profiling of patient samples" PNAS (2010) 107(50):21535-21540.

Final Office Action mailed Aug. 6, 2013 for U.S. Appl. No. 13/139,326.

Fisher, et al. A scalable, fully automated process for construction of sequence-ready human exome targeted capture libraries. Genome Biol. 2011;12(1):R1. doi: 10.1186/GB-2011-12-1-r1. Epub Jan. 4, 2011.

Fox, et al. Accuracy of Next Generation Sequencing Platforms. Next Gener Seq Appl. 2014;1. pii: 1000106.

Frampton, G.M. et al. "Development and validation of a clinical cancer genomic profiling test based on massively parallel DNA sequencing" Nature Biotechnology (2013) 31(11):1023-1031. doi:10.1038/nbr.2696.

Fredrickson, et al. Macro-to-micro interfaces for microfluidic devices. Lab Chip. Dec. 2004;4(6):526-33. Epub Nov. 10, 2004.

Freiberg, et al. Polymer microspheres for controlled drug release. Int J Pharm. Sep. 10, 2004;282(1-2):1-18.

Fu, "A micro fabricated fluorescence-activated cell sorter", Nature Biotech., 17:1109-1111 (1997).

Fu, et al. A Microfabricated Fluorescence-Activated Cell Sorter. Nature Biotechnology. 1999;17:1109-1111.

Fulton, et al. Advanced multiplexed analysis with the FlowMetrix system. Clin Chem. Sep. 1997;43(9):1749-56.

Gangadharan et al., DNA transposon Hermes insert into DNA in nucleosome-free regions in vivo, Proc nat Ad Sci, Dec. 21, 2010, vol. 107, No. 51, pp. 21966-21972.

Gao et al., Toehold of dsDNA Exchange Affects the Hydrogel Swelling Kinetic of a Polymer-dsDNA Hybrid Hydrogel, Royal Soc. Chem. 7:1741-1746 (Dec. 20, 2010).

Garstecki, et al. Formation of monodisperse bubbles in a microfluidic flow-focusing device. Applied Physics Letters. 2004; 85(13):2649-2651. DOI: 10.1063/1.1796526.

Gartner, et al. The Microfluidic Toolbox—examples for fluidic interfaces and standardization concepts. Proc. SPIE 4982, Microfluidics, BioMEMS, and Medical Microsystems, (Jan. 17, 2003); doi: 10.1117/12.479566.

Gericke, et al. Functional cellulose beads: preparation, characterization, and applications. Chemical reviews 113.7 (2013): 4812-4836.

Ghadessy, et al. Directed evolution of polymerase function by compartmentalized self-replication. Proc Natl Acad Sci USA. 2001;98:4552-4557.

Gonzalez, et al. The influence of CCL3L1 gene-containing segmental duplications on HIV-1/AIDS susceptibility. Science. Mar. 4, 2005;307(5714):1434-40. Epub Jan. 6, 2005.

Gordon et al. "Consed: A Graphical Tool for Sequence Finishing," Genome Research (1998) 8:198-202.

Granieri, Lucia. Droplet-based microfluidics and engineering of tissue plasminogen activator for biomedical applications. Ph.D. Thesis, Nov. 13, 2009 (131 pages).

Grasland-Mongrain, et al. Droplet coalescence in microfluidic devices. Jan.-Jul. 2003. 31 pages. http://www.eleves.ens.fr/home/grasland/rapports/stage4.pdf.

Green et al. Insertion site preference of Mu, Tn5, and Tn7 transposons. Mobile DNA 3.1 (2012): 3.

Greenleaf, et al. Assaying the epigenome in limited Nos. of cells. Methods. Jan. 15, 2015;72:51-6. doi: 10.1016/j.ymeth.2014.10.010. Epub Oct. 22, 2014.

Guo, et al. Droplet microfluidics for high-throughput biological assays. Lab Chip. Jun. 21, 2012;12(12):2146-55. doi: 10.1039/c2lc21147e. Epub Feb. 9, 2012.

Gyarmati, et al. Reversible disulphide formation in polymer networks: a versatile functional group from synthesis to applications. European Polymer Journal. 2013; 49:1268-1286.

Hamilton, A.J. "microRNA in erythrocytes" Biochem. Soc. Trans. (2010) 38, 229-231.

Han, SW et al. "Targeted Sequencing of Cancer-Related Genes in Colorectal Cancer Using Next-Generation Sequencing" PLOS One (2013) 8(5):e64271.

(56) References Cited

OTHER PUBLICATIONS

Han, et al. CRISPR-Cas9 delivery to hard-to-transfect cells via membrane deformation. Science Advances (2015) 1(7): E1500454 (8 pages).
Haring, et al. Chromatin immunoprecipitation: optimization, quantitative analysis and data normalization. Plant Methods. 2007; 3: 11.
Hashimshony, et al. CEL-Seq: Single-Cell RNA-Seq by Multiplexed Linear Amplification. Cell Rep. Sep. 27, 2012;2(3):666-73. doi: 10.1016/j.celrep.2012.08.003. Epub Aug. 30, 2012.
He, "Selective Encapsulation of Single Cells and Subcellular Organelles into Picoliter- and Femtoliter-Volume Droplets" Anal. Chem 77: 1539-1544 (2005).
He, J. et al. "Genotyping-by-sequencing (GBS), an ultimate marker-assisted selections (MAS) tool to accelerate plant breeding" Frontiers in Plant Sci (Sep. 30, 2014) 5:1-8.
Hebenstreit. Methods, Challenges and Potentials of Single Cell RNA-seq. Biology (Basel). Nov. 16, 2012;1(3):658-67. doi: 10.3390/biology1030658.
Hiatt, et al. Parallel, tag-directed assembly of locally derived short sequence reads. Nat Methods. Feb. 2010;7(2):119-22. Epub Jan. 17, 2010.
Hirsch et al. (2002) "Easily reversible desthiobiotin binding to streptavidin, avidin, and other biotin-binding proteins: uses for protein labeling, detection, and isolation." Analytical of Biochemistry 308(2):343-357.
Hjerten, et al. General methods to render macroporous stationary phases nonporous and deformable, exemplified with agarose and silica beads and their use in high-performance ion-exchange and hydrophobic-interaction chromatography of proteins. Chromatographia 31.1-2 (1991): 85-94.
Holmberg, et al. The biotin-streptavidin interaction can be reversibly broken using water at elevated temperatures. Feb. 2, 2005. Electrophoresis, 26:501-510.
Holtze, et al. Biocompatible surfactants for water-in-fluorocarbon emulsions. Lab Chip. Oct. 2008;8(10):1632-9. doi: 10.1039/b806706f. Epub Sep. 2, 2008.
Hosokawa, et al. Massively parallel whole genome amplification for single-cell sequencing using droplet microfluidics. Scientific Reports 7, Article No. 5199 (2017).
Hosono S, et al. Unbiased whole-genome amplification directly from clinical samples. Genome Res. May 2003; 13(5):954-64. Epub Apr. 14, 2003.
"How many species of bacteria are there" (wisegeek.com; accessed Jan. 21, 2014).
Hu et al., Shape Controllable Microgel Particles Prepared by Microfluidic Combining External Crosslinking, Biomicrofluidics 6:26502 (May 18, 2012).
Huang et al. EagleView: A genome assembly viewer for next-generation sequencing technologies, Genome Research (2008) 18:1538-1543.
Huebner, "Quantitative detection of protein expression in single cells using droplet microfluidics", Chem. Commun. 1218-1220 (2007).
Hug, et al. Measurement of the number of molecules of a single mRNA species in a complex mRNA preparation. J Theor Biol. Apr. 21, 2003;221(4):615-24.
Illumina, Inc. An Introduction to Next-Generation Sequencing Technology. Feb. 28, 2012.
Illumina Nextera Enrichment Sample Preparation Guide. Feb. 2013.
Illumina TruSeq Custom Enrichment Kit Data Sheet. (c) 2014.
Imburgio, et al., "Studies of promoter recognition and start site selection by T7 RNA polymerase using a comprehensive collection of promoter variants", Biochemistry., 39:10419-30, 2000.
International Preliminary Report on Patentability for International Application No. PCT/US2009/006649 mailed Jun. 30, 2011.
International Preliminary Report on Patentability for PCT Application PCT/US09/005184 mailed Mar. 31, 2011.
International Preliminary Report on Patentability for PCT /US2008/003185 mailed Sep. 17, 2009.
International Preliminary Report on Patentability for PCT/US2008/013912 mailed Jul. 1, 2010.
International Preliminary Report on Patentability from PCT Application PCT/US2010/054050 mailed May 10, 2012.
International search report and written opinion dated Jan. 31, 2011 for PCT/US2010/054050.
International search report and written opinion dated May 14, 2014 for PCT/US2014/015427.
International search report and written opinion dated May 14, 2015 for PCT/US2014/044398.
International search report and written opinion dated May 16, 2014 for PCT/US2013/074764.
International search report and written opinion dated Aug. 16, 2010 for PCT/US2009/005184.
International search report and written opinion dated Aug. 19, 2015 for PCT/US2015/025197.
International search report and written opinion dated Aug. 20, 2014 for PCT/US2014/015424.
International search report and written opinion dated Oct. 21, 2009 for PCT/US2009/003389.
International search report and written opinion dated Nov. 25, 2015 for PCT/US2015/038141.
International search report and written opinion dated Dec. 16, 2013 for PCT/US2013/054797.
International Search Report and Written Opinion of the International Searching Authority for International Application No. PCTIUS2008/013912, mailed Apr. 3, 2009.
International Search Report and Written Opinion of the International Searching Authority for International Application No. PCT/US2008/003185, mailed Jan. 12, 2009.
International Search Report and Written Opinion of the International Searching Authority for International Application No. PCT/US2008/008563, mailed Oct. 29, 2008.
International Search Report and Written Opinion of the International Searching Authority for International Application No. PCT/US2009/004037, mailed Oct. 2, 2009.
International search report dated Apr. 22, 2009 for PCT/US2009/000664.
Invitrogen Dynal. Dynabeads M-280 Streptavidin 2006 product sheet.
Ioannidis, N. Manufacturing of agarose-based chromatographic adsorbents with controlled pore and particle sizes. A thesis submitted to The University of Birmingham for the degree of Doctor of Philosophy. 2009.
Japanese Final Rejection dated Aug. 5, 2014 for Application No. JP 2012-536941.
Japanese Office Action and mailed Jul. 17, 2013 for Application No. JP 2010-539498.
Japanese Office Action mailed Nov. 19, 2013 for Application No. JP 2012-536941.
Jarosz, M. et al. "Using 1ng of DNA to detect haplotype phasing and gene fusions from whole exome sequencing of cancer cell lines" Cancer Res (2015) 75(suppl5):4742.
Jena, et al. Cyclic olefin copolymer based microfluidic devices for biochip applications: Ultraviolet surface grafting using 2-methacryloyloxyethyl phosphorylcholine. Biomicrofluidics. Mar. 2012;6(1):12822-1 to 12822-12. doi: 10.1063/1.3682098. Epub Mar. 15, 2012.
Jin, et al. Genome-wide detection of DNase I hypersensitive sites in single cells and FFPE tissue samples. Nature. Dec. 3, 2015;528(7580):142-6. doi: 10.1038/nature15740.
Joneja, et al. Linear nicking endonuclease-mediated strand-displacement DNA amplification. Anal Biochem. Jul. 1, 2011;414(1):58-69. doi: 10.1016/j.ab.2011.02.025. Epub Feb. 20, 2011.
JPK "Determining the elastic modulus of biological samples using atomic force microscopy" (https://www.jpk.com/ app-technotes-img/AFM/pdf/jpk-app-elastic-modulus.14-1.pdf) 2009, pp. 1-9 (Year: 2009).
Jung, et al. Micro machining of injection mold inserts for fluidic channel of polymeric biochips. Sensors. 2007; 7(8):1643-1654.

(56) References Cited

OTHER PUBLICATIONS

Kamperman, et al. Centering Single Cells in Microgels via Delayed Crosslinking Supports Long-Term 3D Culture by Preventing Cell Escape. Small. Jun. 2017; 13(22). doi: 10.1002/smll.201603711. Epub Apr. 28, 2017.
Kanehisa et al. "KEGG: Kyoto Encyclopedia of Genes and Genomes," Nucleic Acids Research (2000) 28:27-30.
Kaper, et al. Supporting Information for "Whole-genome haplotyping by dilution, amplification, and sequencing." Proc Natl Acad Sci U S A. Apr. 2, 2013;110(14):5552-7. doi: 10.1073/pnas.1218696110. Epub Mar. 18, 2013.
Kaper, et al. Whole-genome haplotyping by dilution, amplification, and sequencing. Proc Natl Acad Sci U S A. Apr. 2, 2013;110(14):5552-7. doi: 10.1073/pnas.1218696110. Epub Mar. 18, 2013.
Karmakar, et al. Organocatalytic removal of formaldehyde adducts from RNA and DNA bases. Nat Chem. Sep. 2015;7(9):752-8. doi: 10.1038/nchem.2307. Epub Aug. 3, 2015.
Katsura, et al. Indirect micromanipulation of single molecules in water-in-oil emulsion. Electrophoresis. Jan. 2001;22(2):289-93.
Kebschull, et al. High-Throughput Mapping of Single-Neuron Projections by Sequencing of Barcoded RNA. Neuron. Sep. 7, 2016;91(5):975-87. doi: 10.1016/j.neuron.2016.07.036. Epub Aug. 18, 2016.
Kenis, et al. Microfabrication Inside Capillaries Using Multiphase Laminar Flow Patterning. Science. 1999; 285:83-85.
Khomiakova et al., Analysis of perfect and mismatched DNA duplexes by a generic hexanucleotide microchip. Mol Biol(Mosk). Jul. 2003-Aug. 37(4):726-41. Russian. Abstract only.
Kim et al., Albumin loaded microsphere of amphiphilic poly(ethylene glycol)/poly(a-ester) multiblock copolymer. Eu. J. Pharm. Sci. 2004;23:245-51. Available online Sep. 27, 2004.
Kim, et al. Fabrication of monodisperse gel shells and functional microgels in microfluidic devices. Angew Chem Int Ed Engl. 2007;46(11):1819-22.
Kim et al. "HapEdit: an accuracy assessment viewer for haplotype assembly using massively parallel DNA-sequencing technologies," Nucleic Acids Research (2011) pp. W557-W561.
Kim, et al. Rapid prototyping of microfluidic systems using a PDMS/polymer tape composite. Lab Chip. May 7, 2009;9(9):1290-3. doi: 10.1039/b818389a. Epub Feb. 10, 2009.
Kirkness et al. "Sequencing of isolated sperm cells for direct haplotyping of a human genome," Genome Res (2013) 23:826-832.
Kirkness et al. Sequencing of isolated sperm cells for direct haplotyping of a human genome,â€ Genome Res (2013) 23:826-832.
Kitzman et al. "Haplotype-resolved genome sequencing of a Gujarati Indian individual." Nat Biotechnol (2011) 29:59-63.
Kitzman, et al. Noninvasive whole-genome sequencing of a human fetus. Sci Transl Med. Jun. 6, 2012;4(137):137ra76. doi: 10.1126/scitranslmed.3004323.
Kivioja, et al. Counting absolute numbers of molecules using unique molecular identifiers. Nat Methods. Nov. 20, 2011;9(1):72-4.
Klein, et al. Droplet barcoding for single-cell transcriptomics applied to embryonic stem cells. Cell. May 21, 2015;161(5):1187-201. doi: 10.1016/j.cell.2015.04.044.
Knapp, et al. Generating barcoded libraries for multiplex high-throughput sequencing. Methods Mol Biol. 2012;840:155-70. doi: 10.1007/978-1-61779-516-9_19.
Knight, et al. Subtle chromosomal rearrangements in children with unexplained mental retardation. Lancet. Nov. 13, 1999;354(9191):1676-81.
Kobayashi, et al. Effect of slot aspect ratio on droplet formation from silicon straight-through microchannels. J Colloid Interface Sci. Nov. 1, 2004;279(1):277-80.
Kolodeziejczyk et al., "The technology and biology of single-cell RNA sequencing", Molecular Cell, vol. 58 (May 21, 2015).
Korlach et al., Methods in Enzymology, Real-Time DNA Sequencing from Single Polymerase Molecules, (2010) 472:431-455.
Koster et al., "Drop-based microfluidic devices for encapsulation of single cells", Lab on a Chip The Royal Soc. of Chem. 8: 1110-1115 (2008).
Kozarewa, et al., "96-plex molecular barcoding for the Illumina Genome Analyzer", Methods Mol Biol., 733:279-98, 2011.
Kozarewa, et al. "Amplification-free Illumina sequencing-library preparation facilitates improved mapping and assembly of GC-biased genomes", Nat Methods., 6: 291-5, 2009.
Kutyavin, et al. Oligonucleotides containing 2-aminoadenine and 2-thiothymine act as selectively binding complementary agents. Biochemistry. Aug. 27, 1996;35(34):11170-6.
Kwok, et al., "Single-molecule analysis for molecular haplotyping", Hum Mutat., 23:442-6, 2004.
Lagally, et al. Single-Molecular DNA Amplification and Analysis in an Integrated Microfluidic Device. Anal Chem. Feb. 1, 2001;73(3):565-70.
Lagus, et al. A review of the theory, methods and recent applications of high-throughput single-cell droplet microfluidics. J. Phys. D: Appl. Phys. (2013) 46:114005. (21 pages).
Lai; et al., ""Characterization and Use of Laser-Based Lysis for Cell Analysis On-Chip", Journal of the Royal Society, Interface, vol. 5, Supplement 2, pp. S113-S121, Oct. 2008, (Year:2008)", Journal of the Royal Society, Interface, Oct. 2008, vol. 5, Supplement 2, S113-S121.
Laird et al, Hairpin-bisulfite PCR: Assessing epigenetic methylation patterns on complementary strands of individual DNA molecules, 2004, PNAS, 101, 204-209.
Lake, et al. "Integrative Single-Cell Analysis By Transcriptional And Epigenetic States In Human Adult Brain". Apr. 19, 2017. doi: https://doi.org/10.1101/128520.
Lan, et al. "Single-cell genome sequencing at ultra-high-throughput with microfluidic droplet barcoding" with Supplementary Material. Nat Biotechnol. May 29, 2017. doi: 10.1038/nbt.3880. [Epub ahead of print].
Lander, et al. Initial sequencing and analysis of the human genome. Nature, 409 (Feb. 15, 2001): 860-921.
Lasken, et al. (1996) Archaebacterial DNA Polymerases Tightly Bind Uracil-containing DNA. The Journal of Biological Chemistry, 271(30):17692-17696 (Year: 1996).
Layer et al. "Lumpy: A probabilistic framework for structural variant discovery," Genome Biology (2014) 15(6):R84.
Lebedev, A. et al. "Hot Start PCR with heat-activatable primers: a novel approach for improved PCR performance" NAR (2008) 36(20):E131-1.
Lee, et al. ACT-PRESTO: Rapid and consistent tissue clearing and labeling method for 3-dimensional (3D) imaging. Sci Rep. Jan. 11, 2016;6:18631. doi: 10.1038/srep18631.
Lee et al. Alginate: Properties and biomedical applications. Prog Polym Sci 37(1):106-126 (2012).
Lee, et al., "Fluorescent in situ sequencing (FISSEQ) of RNA for gene expression profiling in intact cells and tissues" Nature Protocols (Feb. 12, 2015) 10(3):442-458. XP055272042, GB ISSN:1754-2189, DOI: 10.1038/nprot.2014.191.
Lee, et al., Highly Multiplexed Subcellular RNA Sequencing in Situ. Science 343.6177 (Mar. 2014): 1360-1363, doi: 10.1126/science.1250212.
Lennon et al. A scalable, fully automated process for construction of sequence-ready barcoded libraries for 454. Genome Biology 11:R15 (2010).
Li, et al. A single-cell-based platform for copy No. variation profiling through digital counting of amplified genomic DNA fragments. ACS Appl Mater Interfaces. Mar. 24, 2017. doi: 10.1021/acsami.7b03146. [Epub ahead of print].
Li, et al. Fast and accurate long-read alignment with Burrows-Wheeler transform. Bioinformatics 26.5 (2010): 589-595.
Li, et al. Step-emulsification in a microfluidic device. Lab Chip. Feb. 21, 2015;15(4):1023-31. doi: 10.1039/c4lc01289e.
Li, Y., et al., "PEGylated PLGA Nanoparticles as protein carriers: synthesis, preparation and biodistribution in rats," Journal of Controlled Release, vol. 71, pp. 203-211 (2001).
Lienemann, et al. Single cell-laden protease-sensitive microniches for long-term culture in 3D. Lab Chip. Feb. 14, 2017;17(4):727-737. doi: 10.1039/c6lc01444e.
Linch, et al. Bone marrow processing and cryopreservation. Journal of Clinical Pathology; Feb. 1982, vol. 35, No. 2; pp. 186-190.

(56) References Cited

OTHER PUBLICATIONS

Lippert et al. Algorithmic strategies for the single nucleotide polymorphism haplotype assembly problem, Brief. Bionform (2002) 3:23-31.

"List of sequenced bacterial genomes" (Wikipedia.com; accessed Jan. 24, 2014).

Liu, et al. Preparation of uniform-sized PLA microcapsules by combining Shirasu porous glass membrane emulsification technique and multiple emulsion-solvent evaporation method. J Control Release. Mar. 2, 2005;103(1):31-43. Epub Dec. 21, 2004.

Liu, et al. Smart thermo-triggered squirting capsules for Nanoparticle delivery. Soft Matter. 2010; 6(16):3759-3763.

Lo, et al. On the design of clone-based haplotyping. Genome Biol. 2013;14(9):R100.

Loscertales, I.G., et al., "Micro/Nano Encapsulation via Electrified Coaxial Liquid Jets," Science, vol. 295, pp. 1695-1698 (2002).

Love, "A microengraving method for rapid selection of single cells producing antigen-specific antibodies", Nature Biotech, 24:6 703 (Jun. 2006).

Lowe, Adam J. Norbornenes and [n]polynorbornanes as molecular scaffolds for anion recognition. Ph.D. Thesis (May 2010). (361 pages).

Lundin, et al., "Hierarchical molecular tagging to resolve long continuous sequences by massively parallel sequencing", Sci Rep., 3:1186, 2013.

Lupski. Genomic rearrangements and sporadic disease. Nat Genet. Jul. 2007;39(7 Suppl):S43-7.

Maan, et al. Spontaneous droplet formation techniques for monodisperse emulsions preparation—Perspectives for food applications. Journal of Food Engineering. vol. 107, Issues 3-4, Dec. 2011, pp. 334-346.

Macaulay, et al. G&T-seq: parallel sequencing of single-cell genomes and transcriptomes. Nature Methods, 2015, p. 1-7.

Macaulay, et al. Single-Cell Multiomics: Multiple Measurements from Single Cells. Trends in Genetics 33.2 (2017): 155-168. PMC. Web. Dec. 18, 2017.

Macosko, et al. Highly Parallel Genome-wide Expression Profiling of Individual Cells Using Nanoliter Droplets. Cell. May 21, 2015; 161(5):1202-14. doi: 10.1016/j.cell.2015.05.002.

Maeda, et al. Development of a DNA barcode tagging method for monitoring dynamic changes in gene expression by using an ultra high-throughput sequencer. Biotechniques. Jul. 2008;45(1):95-7. doi: 10.2144/000112814.

Mair, et al. Injection molded microfluidic chips featuring integrated interconnects. Lab Chip. Oct. 2006;6(10):1346-54. Epub Jul. 31, 2006.

Makino, et al. Preparation of hydrogel microcapsules: Effects of preparation conditions upon membrane properties. Colloids and Surfaces B: Biointerfaces. Nov. 1998; 12(2), 97-104.

Mali, et al. Barcoding cells using cell-surface programmable DNA-binding domains. Nat Methods. May 2013;10(5):403-6. doi: 10.1038/nmeth.2407. Epub Mar. 17, 2013.

Mamedov, I.Z., et al. (2013), Preparing unbiased T-cell receptor and antibody cDNA libraries for the deep next generation sequencing profiling, Front Immunol 4: 456.

Man. Monolithic Structures for Integrated Microfluidic Analysis. PhD Thesis. 2001.

Marcus. Gene method offers diagnostic hope. The Wall Street Journal. Jul. 11, 2012.

Margulies 2005 Supplementary methods (Year: 2005).

Margulies et al. "Genome sequencing in microfabricated high-density picoliter reactors", Nature (2005) 437:376-380.

Maricic T, et al. Optimization of 454 sequencing library preparation from small amounts of DNA permits sequence determination of both DNA strands. Biotechniques. Jan. 2009; 46(1):51-2, 54-7.

Matochko, et al. Uniform amplification of phage display libraries in monodisperse emulsions. Methods. Sep. 2012;58(1):18-27. doi: 10.1016/j.ymeth.2012.07.012. Epub Jul. 20, 2012.

Mazutis, et al. Selective droplet coalescence using microfluidic systems. Lab Chip. Apr. 24, 2012;12(10):1800-6. doi: 10.1039/c2lc40121e. Epub Mar. 27, 2012.

McCoy, R. et al. "Illumina TruSeq Synthetic Long-Reads Empower De Novo Assembly and Resolve Complex, Highly-Repetitive Transposable Elements" PLOS (2014) 9(9):e1016689.

McGinnis, et al. MULTI-seq: Scalable sample multiplexing for single-cell RNA sequencing using lipid-tagged indices. bioRxiv (2018) 387241; doi: https://doi.org/10.1101/387241.

McKenna, Aaron et al. "The Genome Analysis Toolkit: A MapReduce Framework for Analyzing next-Generation DNA Sequencing Data." Genome Research 20.9 (2010): 1297-1303. PMC. Web. Feb. 2, 2017.

Merriman, et al. Progress in ion torrent semiconductor chip based sequencing. Electrophoresis. Dec. 2012;33(23):3397-417. doi: 10.1002/elps.201200424.

"Meyer, et al., From micrograms to picograms: quantitative PCR reduces the material demands of high-throughput sequencing, Nucleic Acids Research, 2008, vol. 36, No. 1, 6 pages".

Meyer, et al. Targeted high-throughput sequencing of tagged nucleic acid samples. Nucleic Acids Res. 2007;35(15):e97.

Microfluidic ChipShop. Microfluidic product catalogue. Mar. 2005.

Microfluidic ChipShop. Microfluidic product catalogue. Oct. 2009.

Mignardi, M. et al. "Oligonucleotide gap-fill ligation for mutation detection and sequencing in situ" Nucl Acids Res (2015) 43(22):e151.

Miller et al. "Assembly Algorithms for next-generation sequencing data," Genomics, 95 (2010), pp. 315-327.

Miller JC, et al. An improved zinc-finger nuclease architecture for highly specific genome editing. Nat. Biotechnol. 2007;25:778-785.

Miller-Stephenson Chemicals 157 FS Series catalog, http://www.miller-stephenon.com. Feb. 6, 2018.

MiRNA (http://www.exiqon.com/what-are-microRNAs) accessed Oct. 19, 2017.

Mirzabekov, "DNA Sequencing by Hybridization—a Megasequencing Method and A Diagnostic Tool?" Trends in Biotechnology 12(1): 27-32 (1994).

Moore, et al. Behavior of capillary valves in centrifugal microfluidic devices prepared by three-dimensional printing. Microfluidics and Nanofluidics. 2011; 10(4):877-888.

Morgan, et al. Chapter 12: Human microbiome analysis. PLoS Comput Biol. 2012;8(12):e1002808. doi: 10.1371/journal.pcbi.1002808. Epub Dec. 27, 2012.

Morimoto, et al. Monodisperse semi-permeable microcapsules for continuous observation of cells. 2009. Lab Chip 9(15):2217-2223.

Morton. Parameters of the human genome. Apr. 23, 1991. Proceedings of the National Academy of Sciences of the United States of America, 88: 7474-7476.

Mouritzen et al., Single nucleotide polymorphism genotyping using locked nucleic acid (LNa). Expert Rev Mol Diagn. Jan. 2003;3(1):27-38.

Mozhanova, A.A. et al. "Local elastic properties of biological materials studied by SFM" (2003) XP055314108, Retrieved from the Internet: URL:http://www.ntmdt.com/data/media/files/publications/2003/08.08_a.a.mozhanova_n.i.n_english.pdf.

Muotri, et al. L1 retrotransposition in neurons is modulated by MeCP2. Nature. Nov. 18, 2010;468(7322):443-6. doi: 10.1038/nature09544.

Myllykangas et al. "Efficient targeted resequencing of human germline and cancer genomes by oligonucleotide-selective sequencing," Nat Biotechnol, (2011) 29:1024-1027.

Myllykangas et al., Targeted Sequencing Library Preparation By Genomic DNA Circularization, BMC Biotechnology, 2011, 11(122), 1-12.

Nagano, et al. Single-cell Hi-C reveals cell-to-cell variability in chromosome structure. Nature. Oct. 3, 2013;502(7469):59-64. doi: 10.1038/nature12593. Epub Sep. 25, 2013.

Nagashima, et al. Preparation of monodisperse poly (acrylamide-co-acrylic acid) hydrogel microspheres by a membrane emulsification technique and their size-dependent surface properties. Colloids and Surfaces B: Biointerfaces. Jun. 15, 1998; 11(1-2), 47-56.

Narayanan, J. et al. "Determination of agarose gel pore size: Absorbance measurements vis a vis other techniques" Journal of Physics: Conference Series 28 (2006) 83-86 (Year: 2006).

National Human Genome Research Institute (NHGRI). The Human Genome Project Completion: Frequently Asked Questions. Last Updated: Oct. 30, 2010.

(56) References Cited

OTHER PUBLICATIONS

Navin. The first five years of single-cell cancer genomics and beyond. Genome Res. Oct. 2015;25(10):1499-507. doi: 10.1101/gr.191098.115.
Nguyen, et al. In situ hybridization to chromosomes stabilized in gel microdrops. Cytometry. 1995; 21:111-119.
Nisisako, et al. Droplet formation in a microchannel network. Lab Chip. Feb. 2002;2(1):24-6. Epub Jan. 18, 2002.
Nisisako, T. et al. Droplet Formation in a Microchannel on PMMA Plate. Micro Total Analysis Systems. 2001. Kluwer Academic Publishers. pp. 137-138.
Notice of Allowance mailed Jan. 27, 2014 for U.S. Appl. No. 13/139,326.
Novak, et al. Single cell multiplex gene detection and sequencing using microfluidicallygenerated agarose emulsions. Angew Chem Int Ed Engl. Jan. 10, 2011;50(2):390-5. doi: 10.1002/anie.201006089.
Oberholzer, et al. Polymerase chain reaction in liposomes. Chem Biol. Oct. 1995;2(10):677-82.
Office action dated Jan. 15, 2015 for U.S. Appl. No. 14/250,701.
Office action dated Jan. 29, 2016 for U.S. Appl. No. 14/175,935.
Office action dated Feb. 23, 2016 for U.S. Appl. No. 14/104,650.
Office action dated Mar. 1, 2016 for U.S. Appl. No. 14/250,701.
Office action dated Mar. 4, 2016 for U.S. Appl. No. 14/175,973.
Office action dated Mar. 14, 2016 for U.S. Appl. No. 14/680,808.
Office action dated Apr. 20, 2015 for US Appl. No. 13/966,150.
Office action dated May 20, 2014 for U.S. Appl. No. 14/172,266.
Office action dated May 20, 2014 for U.S. Appl. No. 14/172,326.
Office action dated May 28, 2013 for U.S. Appl. No. 12/529,926.
Office action dated Jun. 23, 2016 for U.S. Appl. No. 14/624,473.
Office action dated Jun. 24, 2016 for U.S. Appl. No. 14/624,468.
Office action dated Aug. 5, 2016 for U.S. Appl. No. 14/175,935.
Office action dated Aug. 6, 2014 for U.S. Appl. No. 12/529,926.
Office action dated Aug. 11, 2016 for U.S. Appl. No. 14/250,701.
Office action dated Sep. 10, 2014 for U.S. Appl. No. 14/250,701.
Office action dated Sep. 15, 2016 for U.S. Appl. No. 15/200,928.
Office action dated Sep. 16, 2015 for U.S. Appl. No. 14/175,973.
Office action dated Sep. 25, 2015 for U.S. Appl. No. 14/250,701.
Office action dated Oct. 1, 2012 for U.S. Appl. No. 12/529,926.
Office action dated Oct. 9, 2015 for U.S. Appl. No. 14/680,808.
Office action dated Oct. 12, 2016 for U.S. Appl. No. 14/316,447.
Office action dated Nov. 6, 2015 for US Appl. No. 13/966,150.
Office Action from U.S. Appl. No. 12/172,186 dated Jan. 4, 2010.
Office Action mailed Apr. 24, 2013 for U.S. Appl. No. 13/119,470.
Office Action mailed Apr. 29, 2014 for EP Application No. 08865992.5.
Office Action mailed Dec. 16, 2013 for CN Application No. 201080055990.9.
Office Action mailed Dec. 5, 2013 for U.S. Appl. No. 13/119,470.
Office Action mailed Feb. 10, 2014 for U.S. Appl. No. 13/503,588.
Office Action mailed Feb. 28, 2013 for U.S. Appl. No. 13/139,326.
Office Action mailed Jan. 23, 2012 for EP 08865992.5.
Office Action mailed Jul. 30, 2014 for Appl. No. 12/809,120.
Office Action mailed Jun. 18, 2012 for CN Application No. 200880127116.4.
Office Action mailed May 23, 2013 for CN Application No. 200880127116.4.
Office Action mailed Sep. 17, 2013 for U.S. Appl. No. 13/503,588.
Office Communication mailed Apr. 5, 2013 for Application No. EP 08865992.5.
Office Communication mailed Aug. 29, 2013 for Application No. EP 08865992.5.
Ogawa, et al. Production and characterization of O/W emulsions containing cationic droplets stabilized by lecithin-chitosan membranes. J Agric Food Chem. Apr. 23, 2003;51(9):2806-12.
Okushima, S., et al.,. "Controlled Production of Monodisperse Double Emulsions by Two-Step Droplet Breakup in Microfluidic Devices," Langmuir, vol. 20, pp. 9905-9908 (2004).

Oligotex Handbook. For purification of poly A+ RNA from total RNA and directly from cultured cells or tissues as well as purification of polyadenylated in vitro transcripts. Jun. 2012.
Orakdogen, N. "Novel responsive poly(N,N-dimethylaminoethyl methacrylate) gel beads: preparation, mechanical properties and pH-dependent swelling behavior" J Polym Res (2012) 19:9914.
Oyola, et al, "Optimizing Illumina next-generation sequencing library preparation for extremely AT-biased genomes", BMC Genomics., 13:1, 2012.
Pantel, et al. Detection methods of circulating tumor cells. J Thorac Dis. Oct. 2012;4(5):446-7. doi: 10.3978/j.issn.2072-1439.2012.08.15.
Park. ChIP-seq: advantages and challenges of a maturing technology. Nature Reviews Genetics vol. 10, pp. 669-680 (2009).
Patel, et al. Single-cell RNA-seq highlights intratumoral heterogeneity in primary glioblastoma. Science. Jun. 20, 2014;344(6190):1396-401. doi: 10.1126/science.1254257. Epub Jun. 12, 2014.
PCT/IB2010/002243, International Search Report and Written Opinion, mailed Feb. 9, 2011, 13pgs.
Perez, C., et al., "Poly(lactic acid)-poly(ethylene glycol) Nanoparticles as new carriers for the delivery of plasmid DNA," Journal of Controlled Release, vol. 75, pp. 211-224 (2001).
Perrott, Jimmy. Optimization and Improvement of Emulsion PCR for the Ion Torrent Next-Generation Sequencing Platform. (2011) Thesis.
Peters, B.A. et al. Accurate whole-genome sequencing and haplotyping from 10 to 20 human cells. Nature, 487(7406):190-195 (Jul. 11, 2012).
Pfeifer, et al. Bivalent cholesterol-based coupling of oligonucleotides to lipid membrane assemblies. J Am Chem Soc. Aug. 25, 2004;126(33):10224-5.
Picot, J. et al. "A biomimetic microfluidic chip to study the circulation and mechanical retention of red blood cells in the spleen" Am J Hematology (Jan. 12, 2015) 90(4):339-345.
Pinto, et al. Functional impact of global rare copy number variation in autism spectrum disorders. Nature. Jul. 15, 2010;466(7304):368-72. doi: 10.1038/nature09146. Epub Jun. 9, 2010.
Plunkett, et al. Chymotrypsin responsive hydrogel: application of a disulfide exchange protocol for the preparation of methacrylamide containing peptides. Biomacromolecules. Mar.-Apr. 2005;6(2):632-7.
"Portable Water Filters" (http://www.portablewaterfilters.org/water-filter-guide/particle-contaminant-size-chart-microns/) 2015, accessed Oct. 19, 2017.
Porteus MH, Baltimore D. Chimeric nucleases stimulate gene targeting in human cells. Science. 2003;300:763.
Pott, et al. Single-cell ATAC-seq: strength in numbers. Genome Biol. Aug. 21, 2015;16:172. doi: 10.1186/s13059-015-0737-7.
Preissl, et al. Single nucleus analysis of the chromatin landscape in mouse forebrain development. Posted Jul. 4, 2017. bioRxiv 159137; doi: https://doi.org/10.1101/159137.
"U.S. Appl. No. 61/982,001, filed Apr. 21, 2014 (Year:2014)".
Pushkarev et al. Single-molecule sequencing of an individual human genome, Nature Biotech (2009) 17:847-850.
Qiagen. Omniscript Reverse Transcription Handbook. Oct. 2010.
Rakszewska, A. et al. "One drop at a time: toward droplet microfluidics as a versatile tool for single-cell analysis" NPG Asia Materials (2014) 6(10):e133 (12 pages).
Ram, et al. Strategy for microbiome analysis using 16S rRNA gene sequence analysis on the Illumina sequencing platform. Syst Biol Reprod Med. Jun. 2011;57(3):162-70. doi: 10.3109/19396368.2011.555598. Epub Mar. 1, 2011.
Ramsey, J.M. "The burgeoning power of the shrinking laboratory" Nature Biotech (1999) 17:1061-1062.
Ramskold et al. (2012) "Full-length mRNA-Seq from single-cell levels of RNA and individual circulating tumor cells" Nature Biotechnology 30(8):777-782.
Ran et al. Genome engineering using the CRISPR-Cas9 system. Nature Protocols 8:2281-2308 (2013).
Reis, A. et al. "CRISPR/Cas9 and Targeted Genome Editing: A New Era in Molecular Biology" (2014) XP002766825: URL:https://ww.neb.com/tools-and-resources/feabture-articles/crispr-cas9-and-targeted-genome-editing-a-new-era-in-molecular-biology.

(56) References Cited

OTHER PUBLICATIONS

Reisner, et al, "Single-molecule denaturation mapping of DNA in nanofluidic channels", Proc Natl Acad Sci U.S.A., 107: 13294-9, 2010.
Repp et al. "Genotyping by Multiplex Polymerase Chain Reaction for Detection of Endemic Hepatitis B Virus Transmission" J Clinical Microbiology (1993) 31:1095-1102.
Richardson, et al. Novel inhibition of archaeal family-D DNA polymerase by uracil. Nucleic acids research 41.7 (2013): 4207-4218.
Ritz, A. et al. "Characterization of structural variants with single molecule and hybrid sequencing approaches" Bioinformatics (2014) 30(24):3458-3466.
Roche. Using Multiplex Identifier (MID) Adaptors for the GS FLX Titanium Chemistry Basic MID Set Genome Sequencer FLX System, Technical Bulletin 004-2009, (Apr. 1, 2009) pp. 1-11. URL:http://454.com/downloads/my454/documentation/technical-bulletins/TCB-09004 UsingMultiplexIdentifierAdaptorsForTheGSFLXTitaniumSeriesChemistry-BasicMIDSet.pdf.
Roche. Using Multiplex Identifier (MID) Adaptors for the GS FLX Titanium Chemistry Extended MID Set Genome Sequencer FLX System, Technical Bulletin 005-2009, (Apr. 1, 2009) pp. 1-7. URL:http://454.com/downloads/my454/documentation/technical-bulletins/TCB-09005UsingMultiplexIdentifierAdaptorsForTheGSFLXTitaniumChemistry-ExtendedMIDSet.pdf.
Rodrigue, S. et al. "Whole genome amplification and de novo assembly of single bacterial cells" PLoS One. Sep. 2, 2009;4(9):e6864. doi: 10.1371/journal.pone.0006864.
Rogozin, et al. A highly conserved family of inactivated archaeal B family DNA polymerases. Biol Direct. Aug. 6, 2008;3:32. doi: 10.1186/1745-6150-3-32.
Ropers. New perspectives for the elucidation of genetic disorders. Am J Hum Genet. Aug. 2007;81(2):199-207. Epub Jun. 29, 2007.
Rotem, et al. High-Throughput Single-Cell Labeling (Hi-SCL) for RNA-Seq Using Drop-Based Microfluidics. PLoS One. May 22, 2015;10(5):e0116328. doi: 10.1371/journal.pone.0116328. eCollection 2015.
Rotem, et al. Single Cell Chip-Seq Using Drop-Based Microfluidics. Abstract #50. Frontiers of Single Cell Analysis, Stanford University Sep. 5-7, 2013.
Rotem, et al. Single-cell ChIP-seq reveals cell subpopulations defined by chromatin state. Nat Biotechnol. Nov. 2015;33(11):1165-72. doi: 10.1038/nbt.3383. Epub Oct. 12, 2015.
Ryan, "Rapid assay for mycobacterial growth and antibiotic susceptibility using gel microdrop and encapsulation", J. Clinical Microbial., 33:7 1720-1726 (1995).
Sahin, et al. Microfluidic EDGE emulsification: the importance of interface interactions on droplet formation and pressure stability. Sci Rep. May 27, 2016;6:26407. doi: 10.1038/srep26407.
Sakaguchi, et al. (1996) Cautionary Note on the Use of dUMP-Containing PCR Primers with Pfu and VentR. Biotechniques, 21(3): 368-370 (Year: 1996).
Sander JD, et al. Selection-free zinc-finger-nuclease engineering by context-dependent assembly (CoDA). Nat. Methods. 2011;8:67-69.
Savva, et al. The structural basis of specific base-excision repair by uracil-DNA glycosylase. Nature. Feb. 9, 1995;373(6514):487-93.
Schirinzi et al., Combinatorial sequencing-by-hybridization: Analysis of the NF1 gene. Genet Test. 2006 Spring;10(1):8-17.
Schmieder, et al. Fast identification and removal of sequence contamination from genomic and metagenomic datasets. PLoS One. Mar. 9, 2011;6(3):e17288. doi: 10.1371/journal.pone.0017288.
Schmitt, "Bead-based multiplex genotyping of human papillomaviruses", J. Clinical Microbial., 44:2 504-512 (2006).
Schubert, et al. Microemulsifying fluorinated oils with mixtures of fluorinated and hydrogenated surfactants. Colloids and Surfaces A; Physicochemical and Engineering Aspects, 84(1994) 97-106.
Schwartz, et al., "Capturing native long-range contiguity by in situ library construction and optical sequencing", PNAS (Nov. 2012), 109(46)18749-18754.
Sebat, et al. Strong association of de novo copy number mutations with autism. Science. Apr. 20, 2007;316(5823):445-9. Epub Mar. 15, 2007.
Seiffert, et al. Microfluidic fabrication of smart microgels from macromolecular precursors.Polymer. vol. 51, Issue 25, Nov. 26, 2010, pp. 5883-5889.
Seiffert, et al. Smart microgel capsules from macromolecular precursors. J Am Chem Soc. May 12, 2010;132(18):6606-9. doi: 10.1021/ja102156h.
Shah, "Fabrication of mono disperse thermosensitive microgels and gel capsules in micro fluidic devices", Soft Matter, 4:2303-2309 (2008).
Shahi, et al. Abseq: Ultrahigh-throughput single cell protein profiling with droplet microfluidic barcoding. Sci Rep. 2017; 7: 44447. Published online Mar. 14, 2017. doi: 10.1038/srep44447.
Shaikh, et al. A modular microfluidic architecture for integrated biochemical analysis. Proc Natl Acad Sci U S A. Jul. 12, 2005;102(28):9745-50. Epub Jun. 28, 2005.
Shendure, et al., Accurate Multiplex Polony Sequencing of an Evolved Bacterial Genome. Science 309.5741 (Sep. 2005): 1728-1732. XP002427180, ISSN: 0036-8075, DOI: 10.1126/SCIENCE.1117839.
Shimkus, et al. A chemically cleavable biotinylated nucleotide: usefulness in the recovery of protein-DNA complexes from avidin affinity cols. Proc Natl Acad Sci U S A. May 1985;82(9):2593-7.
Shlien, et al. Copy number variations and cancer. Genome Med. Jun. 16, 2009;1(6):62. doi: 10.1186/gm62.
Shlien, et al. Excessive genomic DNA copy No. variation in the Li-Fraumeni cancer predisposition syndrome. Proc Natl Acad Sci U S A. Aug. 12, 2008;105(32):11264-9. doi: 10.1073/pnas.0802970105. Epub Aug. 6, 2008.
Shuttleworth, et al. Recognition of the pro-mutagenic base uracil by family B DNA polymerases from archaea. J Mol Biol. Mar. 26, 2004;337(3):621-34.
Sigma. Streptavidin-agarose (S1638) product information sheet. www.sigma-aldrich.com.
Simeonov et al., Single nucleotide polymorphism genotyping using short, fluorescently labeled locked nucleic acid (LNA) probes and fluorescence polarization detection. Nucleic Acids Res. Sep. 1, 2002;30(17):e91.
Simon, et al., "Using formaldehyde-assisted isolation of regulatory elements (FAIRE) to isolate active regulatory DNA", Nature Protocols, 2012, 7(2): 256-267.
Skerra. Phosphorothioate primers improve the amplification of DNA sequences by DNA polymerases with proofreading activity. Nucleic Acids Res. Jul. 25, 1992; 20(14):3551-4.
Smith, et al. Highly-multiplexed barcode sequencing: an efficient method for parallel analysis of pooled samples. Nucleic Acids Research, 38(13): e142 (2010).
Song, et al., "DNase-seq: A High-Resolution Technique for Mapping Active Gene Regulatory Elements across the Senome from Mammalian Cells", Cold Spring Harbor Laboratory Press, 2010, 2010(2), doi:10.1101/pdb.prot5384.
Song, et al. Reactions in droplets in microfluidic channels. Angew Chem Int Ed Engl. Nov. 13, 2006;45(44):7336-56.
Sorokin et al., Discrimination between perfect and mismatched duplexes with oligonucleotide gel microchips: role of thermodynamic and kinetic effects during hybridization. J Biomol Struct Dyn. Jun. 2005;22(6):725-34.
Spormann Laboratory, Polymerase Chain Reaction (PCR), Alfred Spormann Laboratory, 2009, 1-3. (Year: 2009).
SSH Tunnel—Local and Remote Port Forwarding Explained With Examples, Trackets Blog, http://blog.trackets.com/2014/05/17/ssh-tunnel-local-and-remote-port-forwarding-explained-with-examples.html; Retrieved from the Internet Jul. 7, 2016.
Stoeckius, et al. Large-scale simultaneous measurement of epitopes and transcriptomes in single cells. bioRxiv 113068; doi: https://doi.org/10.1101/113068; (Mar. 2, 2017).
Stoeckius, et al. Simultaneous epitope and transcriptome measurement in single cells. Nature methods. Jul. 31, 2017.
Su, et al., Microfluidics-Based Biochips: Technology Issues, Implementation Platforms, and Design-Automation Challenges. IEEE

(56) References Cited

OTHER PUBLICATIONS

Transactions on Computer-Aided Design of Integrated Circuits and Systems. 2006;25(2):211-23. (Feb. 2006).
Sun et al., Progress in research and application of liquid-phase chip technology. Chinese Journal Experimental Surgery. May 2005;22(5):639-40.
Susaki, et al. Whole-brain imaging with single-cell resolution using chemical cocktails and computational analysis. Cell. Apr. 24, 2014;157(3):726-39. doi: 10.1016/j.cell.2014.03.042. Epub Apr. 17, 2014.
Syed, et al. Next-generation sequencing library preparation: simultaneous fragmentation and tagging using in vitro transposition. Nature Methods 2 pgs (Nov. 2009).
Tawfik, D.S., et al., "Man-made cell-like compartments for molecular evolution," Nature Biotechnology, vol. 16, pp. 652-656 (1998).
Tayyab, S. et al. Size exclusion chromatography and size exclusion HPLC of proteins. Biochem Ed, Pergamon. 19(3):149-152 (1991).
Tewhey, et al. Microdroplet-based PCR amplification for large-scale targeted sequencing. Nat Biotechnol. Nov. 2009;27(11):1025-31. doi: 10.1038/nbt.1583. Epub Nov. 1, 2009.
Tewhey et al., Supplementary Materials, Nature Biotechnology, 2009, 27(11), 1-22.
Tewhey et al. The importance of phase information for human genomics, Nat Rev Genet (2011) 12:215-223.
Thaxton, C.S. et al. "A Bio-Bar-Code Assay Based Upon Dithiothreitol Oligonucleotide Release" Anal Chem (2005) 77:8174-8178.
The SAM/BAM Format Specificatio Working Group, "Sequence Allignment/ Map Format Specification," Sep. 6, 2016.
Theberge, et al. Microdroplets in microfluidics: an evolving platform for discoveries in chemistry and biology. Angew Chem Int Ed Engl. Aug. 9, 2010;49(34):5846-68. doi: 10.1002/anie.200906653.
ThermoFisher, Protocols, M-270 Streptavidin, ThermoFisherScientific, 2007, 1-5. (Year: 2007).
Thorsen, et al. Dynamic pattern formation in a vesicle-generating microfluidic device. Physical Review Letters. American Physical Society. 2001; 86(18):4163-4166.
Tomer, et al. Advanced CLARITY for rapid and high-resolution imaging of intact tissues. Nat Protoc. Jul. 2014;9(7):1682-97. doi: 10.1038/nprot.2014.123. Epub Jun. 19, 2014.
Tonelli, et al. Perfluoropolyether functional oligomers: unusual reactivity in organic chemistry. Journal of fluorine chemistry. 2002; 118(1)"107-121.
Tubeleviciute, et al. Compartmentalized self-replication (CSR) selection of Thermococcus litoralis Sh1B DNa polymerase for diminished uracil binding. Protein Eng Des Sel. Aug. 2010;23(8):589-97. doi: 10.1093/protein/gzq032. Epub May 31, 2010.
Turner, et al. Assaying chromosomal inversions by single-molecule haplotyping. Nat Methods. Jun. 2006;3(6):439-45.
Turner, et al., "High-throughput haplotype determination over long distances by haplotype fusion PCR and ligation haplotyping", Nat Protoc., 4:1771-83, 2009.
Turner, et al. Methods for genomic partitioning. Annu Rev Genomics Hum Genet. 2009;10:263-84. doi: 10.1146/annurev-genom-082908-150112. Review.
Ullal et al. Cancer Cell Profiling by Barcoding Allows Multiplexed Protein Analysis in Fine-Needle Aspirates. Sci Transl Med. Jan. 15, 2014; 6(219): 219ra9.
Umbanhowar, P.B., et al., "Monodisperse Emulsion Generation via Drop Break Off in a Coflowing Stream," Langmuir, vol. 16, pp. 347-351 (2000).
U.S. Appl. No. 14/682,952, filed Apr. 8, 2015.
U.S. Appl. No. 14/752,602, filed Aug. 26, 2015.
U.S. Appl. No. 14/752,641, filed Aug. 26, 2015.
Ushijima et al, Detection and interpretation of altered methylation patterns in cancer cells, 2005, Nature reviews, 5, 223-231.
Van Dijke, et al. Effect of viscosities of dispersed and continuous phases in microchannel oil-in-water emulsification . Microfluid Nanofluid (2010) 9: 77. https://doi.org/10.1007/s10404-009-0521-7 .
Van Nieuwerburgh, et al., "Illumina mate-paired DNA sequencing-library preparation using Cre-Lox recombination", Nucleic Acids Res., 40:1-8, 2012.
Voskoboynik, A. et al. The genome sequence of the colonial chordate, Botryllus schlosseri. eLife, 2:e00569 (2013). doi: 10.7554/eLife.00569. Epub Jul. 2, 2013.
Wagner, et al. Biocompatible fluorinated polyglycerols for droplet microfluidics as an alternative to PEG-based copolymer surfactants. Lab Chip. Jan. 7, 2016;16(1):65-9. doi: 10.1039/c5lc00823a. Epub Dec. 2, 2015.
Wang, et al. A novel thermo-induced self-bursting microcapsule with magnetic-targeting property. Chemphyschem. Oct. 5, 2009;10(14):2405-9.
Wang, et al. Digital karyotyping. Proc Natl Acad Sci U S A. Dec. 10, 2002;99(25):16156-61. Epub Dec. 2, 2002.
Wang et al., "Self-Formed Adaptor PCR: a Simple and Efficient Method for Chromosome Walking", Applied and Environmental Microbiology (Aug. 2007), 73(15):5048-5051.
Wang et al., Single nucleotide polymorphism discrimination assisted by improved base stacking hybridization using oligonucleotide microarrays. Biotechniques. 2003;35:300-08.
Ward, et al. Microfluidic flow focusing: Drop size and scaling in pressure versus flow-rate-driven pumping. Electrophoresis. Oct. 2005;26(19):3716-24.
Weaver, "Rapid clonal growth measurements at the single-cell level: gel microdroplets and flow cytometry", Biotechnology, 9:873-877 (1991).
Weigl, et al. Microfluidic Diffusion-Based Separation and Detection. Science. 1999; pp. 346-347.
Wesolowska, et al. Cost-effective multiplexing before capture allows screening of 25 000 clinically relevant SNPs in childhood acute lymphoblastic leukemia. Leukemia. Jun. 2011;25(6):1001-6. doi: 10.1038/leu.2011.32. Epub Mar. 18, 2011.
Wheeler et al., "Database resources of the National Center for Biotechnology Information," Nucleic Acids Res. (2007) 35 (Database issue): D5-12.
Whitesides, "Soft lithography in biology and biochemistry", Annual Review of Biomedical Engineering, 3:335-373 (2001).
Williams, et al. Amplification of complex gene libraries by emulsion PCR. Nature Methods. 2006;3(7):545-50.
Wiseman, R.W. et al. "Major histocompatibility complex genotyping with massively parallel pyrosequencing" Nature Medicine (Oct. 11, 2009) 15(11):1322-1326.
Wong, et al. Multiplexed Barcoded CRISPR-Cas9 Screening Enabled By CombiGEM. PNAS. Mar. 1, 2016, vol. 113, pp. 2544-2549.
Woo, et al. G/C-modified oligodeoxynucleotides with selective complementarity: synthesis and hybridization properties. Nucleic Acids Res. Jul. 1, 1996;24(13):2470-5.
Wood AJ, et al. Targeted genome editing across species using ZFNs and TALENs. Science. 2011;333:307.
Xi, et al. New library construction method for single-cell genomes. PLoS One. Jul. 19, 2017;12(7):e0181163. doi: 10.1371/journal.pone. 0181163. eCollection 2017.
Xia and Whitesides, Soft Lithography, Angew. Chem. Int. Ed. 37:550-575 (1998).
Xia and Whitesides, Soft Lithography, Ann. Rev. Mat. Sci. 28:153-184 (1998).
Xiao, et al., "Determination of haplotypes from single DNA molecules: a method for single-molecule barcoding", Hum Mutat., 28:913-21, 2007.
Yamamoto, et al. Chemical modification of Ce(IV)/EDTA-base artificial restriction DNA cutter for versatile manipulation of double-stranded DNA. Nucleic Acids Research. 2007; 35(7):e53.
Yan, Pu et al. "Rapid one-step construction of hairpin RNA" Biochem and Biophys Res Comm (Jun. 12, 2009) 383(4):464-468.
Zeng, et al. High-performance single cell genetic analysis using microfluidic emulsion generator arrays. Anal Chem. Apr. 15, 2010;82(8):3183-90. doi: 10.1021/ac902683t.
Zentner, et al. Surveying the epigenomic landscape, one base at a time. Genome Biol. Oct. 22, 2012;13(10):250. doi: 10.1186/gb4051.
Zerbino, Daniel, "Velvet Manual—version 1.1," Aug. 15, 2008, pp. 1-22.

(56) References Cited

OTHER PUBLICATIONS

Zerbino, D.R. "Using the Velvet de novo assembler for short-read sequencing technologies" Curr Protoc Bioinformatics. Sep. 2010;Chapter 11:Unit 11.5. doi: 10.1002/0471250953.bi1105s31.

Zerbino et al. "Velvet: Algorithms for de novo short read assembly using de Bruijn graphs," Genome Research (2008) 18:821-829.

Zhang, "Combinatorial marking of cells and organelles with reconstituted fluorescent proteins", Cell, 119:137-144 (Oct. 1, 2004).

Zhang, et al. Degradable disulfide core-cross-linked micelles as a drug delivery system prepared from vinyl functionalized nucleosides via the RAFT process. Biomacromolecules. Nov. 2008;9(11):3321-31. doi: 10.1021/bm800867n. Epub Oct. 9, 2008.

Zhang, et al. One-step fabrication of supramolecular microcapsules from microfluidic droplets. Science. Feb. 10, 2012;335(6069):690-4. doi: 10.1126/science.1215416.

Zhang, et al. Reconstruction of DNA sequencing by hybridization. Bioinformatics. Jan. 2003;19(1):14-21.

Zhang F, et al. Efficient construction of sequence-specific TAL effectors for modulating mammalian transcription. Nat. Biotechnol. 2011;29:149-153.

Zhang. Genomics of inherited bone marrow failure and myelodysplasia. Dissertation [online]. University of Washington. 2015 [Retrieved on May 3, 2017].

Zhao, J., et al., "Preparation of hemoglobin-loaded Nano-sized particles with porous structure as oxygen carriers," Biomaterials, vol. 28, pp. 1414-1422 (2007).

Zheng, et al. Massively parallel digital transcriptional profiling of single cells. Nat Commun. Jan. 16, 2017;8:14049. doi: 10.1038/ncomms14049.

Zheng, X.Y. et al. "Haplotyping germline and cancer genomes with high-throughput linked-read sequencing" Nature Biotech (Feb. 1, 2016) 34(3):303-311.

Zhou, Y. et al. "Development of an enzyme activity screening system for p-glucosidase-displaying yeasts using calcium alginate micro-beads and flow sorting" Appl Microbiol Biotechnol (2009) 84:375-382 (Year: 2009).

Zhu et al. Hydrogel Droplet Microfluidics for High-Throughput Single Molecule/Cell Analysis. Accounts of Chemical Research Article ASAP. DOI: 10.1021/acs.accounts.6b00370.

Zhu, et al. Reverse transcriptase template switching: a SMART approach for full-length cDNA library construction. Biotechniques. Apr. 2001;30(4):892-7.

Zhu, et al. Synthesis and self-assembly of highly incompatible polybutadienepoly(hexafluoropropoylene oxide) diblock copolymers. Journal of Polymer Science Part B: Polymer Physics. 2005; 43(24):3685-3694.

Zimmermann et at., Microscale production of hybridomas by hypo-osmolar electrofusion. Hum Antibodies Hybridomas. Jan. 1992;3 (1 ): 14-8.

Zong et al. Genome-Wide Detection of Single Nucleotide and Copy Number Variations of a Single Human Cell. Science 338(6114):1622-1626 (2012).

10X Genomics, Inc. CG000153 Rev A. Chromium Single Cell DNA Reagent Kits User Guide. 2018.

10X Genomics, Inc. CG000184 Rev A. Chromium Single Cell 3' Reagent Kits v3 User Guide with Feature Barcoding Technology for CRISPR Screening. 2018.

10X Genomics, Inc. CG000185 Rev B. Chromium Single Cell 3' Reagent Kits User Guide with Feature Barcoding Technology for Cell Surface Protein. 2018.

10X Genomics, Inc. CG000208 Rev E. Chromium Next GEM Single Cell V(D)J reagent Kits v1.1 User Guide with Feature Barcode Technology for Cell Surface Protein. 2020.

10X Genomics, Inc. CG000209 Rev D. Chromium Next GEM Single Cell ATAC Reagent Kits v1.1 User Guide. 2020.

10X Genomics, Inc. CG000239 Rev B. Visium Spatial Gene Expression Reagent Kits User Guide. 2020.

10X Genomics, Inc. CG00026. Chromium Single Cell 3' Reagent Kit User Guide. 2016.

10X Genomics, Inc. LIT00003 Rev B Chromium Genome Solution Application Note. 2017.

Baret, "Surfactants in droplet-based microfluidics" Lab Chip (12(3):422-433 (2012).

Beer et al. On-Chip, Real-Time, Single-Copy Polymerase Chain Reaction in Picoliter Droplets. Anal Chem 79:8471-8475 (2007).

Chien et al. "Multiport flow-control system for lab-on-a-chip microfluidic devices", Fresenius J. Anal Chem, 371:106-111 (Jul. 27, 2001).

Co-pending U.S. Appl. No. 16/434,076, inventor Giresi; Paul, filed on Jun. 6, 2019.

Co-pending U.S. Appl. No. 16/434,084, inventor Giresi; Paul, filed on Jun. 6, 2019.

Co-pending U.S. Appl. No. 16/434,102, inventors Price; Andrew D. et al., filed on Jun. 6, 2019.

Co-pending U.S. Appl. No. 16/708,214, inventors Wheeler; Tobias Daniel et al., filed on Dec. 9, 2019.

Co-pending U.S. Appl. No. 16/737,762, inventors Price; Andrew D. et al., filed on Jan. 8, 2020.

Co-pending U.S. Appl. No. 16/737,770, inventors Belhocine; Zahara Kamila et al., filed on Jan. 8, 2020.

Co-pending U.S. Appl. No. 16/789,273, inventors Maheshwari; Arundhati Shamoni et al., filed on Feb. 12, 2020.

Co-pending U.S. Appl. No. 16/800,450, inventor Katherine; Pfeiffer, filed on Feb. 25, 2020.

Co-pending U.S. Appl. No. 17/014,909, inventor Giresi; Paul, filed on Sep. 8, 2020.

Co-pending U.S. Appl. No. 17/148,942, inventors McDermott; Geoffrey et al., filed on Jan. 14, 2021.

Co-pending U.S. Appl. No. 17/166,982, inventors McDermott; Geoffrey et al., filed on Feb. 3, 2021.

Co-pending U.S. Appl. No. 17/175,542, inventors Maheshwari; Arundhati Shamoni et al., filed on Feb. 12, 2021.

Co-pending U.S. Appl. No. 17/220,303, inventor Walter; Dagmar, filed on Apr. 1, 2021.

Co-pending U.S. Appl. No. 17/381,612, inventor Martinez; Luigi Jhon Alvarado, filed on Jul. 21, 2021.

Duffy et al., Rapid Protyping of Microfluidic Systems and Polydimethylsiloxane, Anal Chem 70:4974-4984 (1998).

Ellison et al. Mutations in Active-Site Residues of the Uracil-DNA Glycosytase Encoded by Vaccinia Virus are Incompatible with Virus Viability. J Virology (1996) 70(11):7965-7973.

Islam, et al. Highly multiplexed and strand-specific single-cell RNA 5' end sequencing. Nat Protoc. Apr. 5, 2012;7(5):813-28. doi: 10.1038/nprot.2012.022.

Jaitin, et al. Massively parallel single-cell RNA-seq for marker-free decomposition of tissues into cell types. Science. Feb. 14, 2014;343(6172):776-9. doi: 10.1126/science.1247651.

Madl, et al. "Bioorthogonal Strategies for Engineering Extracellular matrices", Madal, Chritopher, Adv. Funct. Master. Jan. 19, 2018, vol. 28, 1706046, pp. 1-21.

Nisisako, T. et al., Microfluidics large-scale integration on a chip for mass production of monodisperse droplets and particles, The Royal Society of Chemistry: Lab Chip, (Nov. 23, 2007) 8:287-293.

Priest, et al. Generation of Monodisperse Gel Emulsions in a Microfluidic Device, Applied Physics Letters, 88:024106 (2006).

Saikia, et al. Simultaneous multiplexed amplicon sequencing and transcriptome profiling in single cells. Nat Methods. Jan. 2019;16(1):59-62. doi: 10.1038/s41592-018-0259-9. Epub Dec. 17, 2018.

Schrider, et al., Gene Copy-Number Polymorphism Caused by Retrotransposition in Humans. PLos Genetics 2013; vol. 9, Issue 1. https://doi.org/10.1371/journal.pgen.1003242.

Turchinovich, et al. "Capture and Amplification by Tailing and Switching (CATS): An Ultrasensitive Ligation-Independent Method for Generation of DNA Libraries for Deep Sequencing from Picogram Amounts of DNA and RNA." RNA Biology 11.7 (2014): 817-828. PMC. Web. Nov. 13, 2017.

Uttamapinant, et al. Fast, cell-compatible click chemistry with copper-chelating azides for biomolecular labeling. Angew. Chem. Int. End. Engl., Jun. 11, 2012: 51(24) pp. 5852-5856.

Vitak, et al. Sequencing thousands of single-cell genomes with combinatorial indexing. Nature methods 14.3 (2017): 302-308.

(56) References Cited

OTHER PUBLICATIONS

Wang, et al. Efficient and unique cobarcoding of second-generation sequencing reads from long DNA molecules enabling cost-effective and accurate sequencing, haplotyping, and de novo assembly. Genome Research 29.5 (2019): 798-808.

* cited by examiner

→ Limited Power to Detect

Fusion

Wild Type

ANALYSIS OF NUCLEIC ACID SEQUENCES

CROSS-REFERENCE

This application is a continuation of U.S. patent application Ser. No. 14/752,589, filed Jun. 26, 2015, which claims priority to U.S. Provisional Patent Application No. 62/017,808, filed Jun. 26, 2014, and U.S. Provisional Patent Application No. 62/072,214, filed Oct. 29, 2014, each of which applications is herein incorporated by reference in its entirety for all purposes.

BACKGROUND

A fundamental understanding of a particular human genome may require more than simply identifying the presence or absence of certain genetic variations such as mutations. It is also important to determine whether certain genetic variations appear on the same or different chromosomes (also known as phasing). Information about patterns of genetic variations, such as haplotypes is also important, as is information about the number of copies of genes.

The term "haplotype" refers to sets of DNA sequence variants (alleles) that are inherited together in contiguous blocks. In general, the human genome contains two copies of each gene—a maternal copy and a paternal copy. For a pair of genes each having two possible alleles, for example gene alleles "A" and "a", and gene alleles "B" and "b", the genome of a given individual will include one of two haplotypes, "AB/ab", where the A and B alleles reside on the same chromosome (the "cis" configuration), or "Ab/aB, where the A and B alleles reside on different chromosomes (the "trans" configuration). Phasing methods or assays can be used to determine whether a specified set of alleles reside on the same or different chromosomes. In some cases, several linked alleles that define a haplotype may correlate with, or be associated with, a particular disease phenotype; in such cases, a haplotype, rather than any one particular genetic variant, may be the most determinative factor as to whether a patient will display the disease.

Gene copy number also plays a role in some disease phenotypes. Most genes are normally present in two copies, however, amplified genes are genes that are present in more than two functional copies. In some instances, genes may also undergo a loss of functional copies. A loss or gain in gene copy number can lead to the production of abnormal levels of mRNA and protein expression, potentially leading to a cancerous state or other disorder. Cancer and other genetic disorders are often correlated with abnormal (increased or decreased) chromosome numbers ("aneuploidy"). Cytogenetic techniques such as fluorescence in situ hybridization or comparative genomic hybridization can be used to detect the presence of abnormal gene or chromosome copy numbers. Improved methods of detecting genetic phasing information, haplotypes or copy number variations are needed in the art.

SUMMARY

The present disclosure provides methods and systems that may be useful in providing significant advances in the characterization of genetic material. These methods and systems can be useful in providing genetic characterizations that may be substantially difficult using generally available technologies, including, for example, haplotype phasing, identifying structural variations, e.g., deletions, duplications, copy-number variants, insertions, inversions, translocations, long tandem repeats (LTRs), short tandem repeats (STRs), and a variety of other useful characterizations.

An aspect of the disclosure provides a method for identifying one or more variations in a nucleic acid, comprising: a) providing a first fragment of the nucleic acid, wherein the first fragment has a length greater than 10 kilobases (kb); (b) sequencing a plurality of second fragments of the first fragment to provide a plurality of fragment sequences, which plurality of fragment sequences share a common barcode sequence; (c) attributing the plurality of fragment sequences to the first fragment by a presence of the common barcode sequence; (d) determining a nucleic acid sequence of the first fragment using the plurality of fragment sequences, wherein the nucleic acid sequence is determined at an error rate of less than 1%; and; (e) identifying the one or more variations in the nucleic acid sequence of the first fragment determined in (d), thereby identifying the one or more variations within the nucleic acid.

In some cases, the first fragment is in a discrete partition in among a plurality of discrete partitions. In some cases, the discrete partition is a droplet in an emulsion. In some cases the identifying comprises identifying phased variants in the nucleic acid sequence of the first fragment. In some cases, the identifying comprises identifying one or more structural variations in the nucleic acid from the nucleic acid sequence of the first fragment. In some cases, the first fragment has a length greater than 15 kb. In some cases, the first fragment has a length greater than 20 kb. In some cases, the determining comprises mapping the plurality of fragment sequences to a reference. In some cases, the determining comprises assembling the plurality of fragment sequences with the common barcode sequence.

In some cases, the method for identifying one or more variations further comprises providing a plurality of first fragments of the nucleic acid that are at least 10 kb in length, and the identifying comprises determining a nucleic acid sequence from each of the plurality of first fragments and identifying the one or more variations in the nucleic acid from the nucleic acid sequence from each of the plurality of first fragments.

In some cases, the method for identifying one or more variations further comprises linking two or more nucleic acid sequences of the plurality of first fragments in an inferred contig based upon overlapping nucleic acid sequences of the two or more nucleic acid sequences, wherein the maximum inferred contig length is at least 10 kb. In some cases, the maximum inferred contig length is at least 20 kb. In some cases, the maximum inferred contig length is at least 40 kb. In some cases, the maximum inferred contig length is at least 50 kb. In some cases, the maximum inferred contig length is at least 100 kb. In some cases, the maximum inferred contig length is at least 200 kb. In some cases, the maximum inferred contig length is at least 500 kb. In some cases, the maximum inferred contig length is at least 750 kb. In some cases, the maximum inferred contig length is at least 1 megabase (Mb). In some cases, the maximum inferred contig length is at least 1.75 Mb. In some cases, the maximum inferred contig length is at least 2.5 Mb.

In some cases, the method for identifying one or more variations further comprises linking two or more nucleic acid sequences of the plurality of first fragments in a phase block based upon overlapping phased variants within the two or more nucleic acid sequences of the plurality of first fragments, wherein the maximum phase block length is at least 10 kb. In some cases, the maximum phase block length is at least 20 kb. In some cases, the maximum phase block length is at least 40 kb. In some cases, the maximum phase block length is at least 50 kb. In some cases, the maximum phase block length is at least 100 kb. In some cases, the maximum phase block length is at least 200 kb. In some cases, the maximum phase block length is at least 500 kb. In some cases, the maximum phase block length is at least 750 kb. In some cases, the maximum phase block length is at least 1 Mb. In some cases, the maximum phase block length is at least 1.75 Mb. In some cases, maximum phase block length is at least 2.5 Mb.

In some cases, the method for identifying one or more variations further comprises linking two or more nucleic acid sequences of the plurality of first fragments in an inferred contig based upon overlapping nucleic acid sequences of the two or more nucleic acid sequences, thereby creating a population of inferred contigs, wherein the N50 of the population of inferred contigs is at least 10 kb. In some cases, the N50 of the population of inferred contigs is at least 20 kb. In some cases, the N50 of the population of inferred contigs is at least 40 kb. In some cases, the N50 of the population of inferred contigs is at least 50 kb. In some cases, the N50 of the population of inferred contigs is at least 100 kb. In some cases, the N50 of the population of inferred contigs is at least 200 kb. In some cases, the N50 of the population of inferred contigs is at least 500 kb. In some cases, the N50 of the population of inferred contigs is at least 750 kb. In some cases, the N50 of the population of inferred contigs is at least 1 Mb. In some cases, the N50 of the population of inferred contigs is at least 1.75 Mb. In some cases, the N50 of the population of inferred contigs is at least 2.5 Mb.

In some cases, the method for identifying one or more variations further comprises linking two or more nucleic acid sequences of the plurality of first fragments in a phase block based upon overlapping phased variants within the two or more nucleic acid sequences of the plurality of first fragments, thereby creating a population of phase blocks, wherein the N50 of the population of phase blocks is at least 10 kb. In some cases, the N50 of the population of phase blocks is at least 20 kb. In some cases, the N50 of the population of phase blocks is at least 40 kb. In some cases, the N50 of the population of phase blocks is at least 50 kb. In some cases, the N50 of the population of phase blocks is at least 100 kb. In some cases, the N50 of the population of phase blocks is at least 200 kb. In some cases, the N50 of the population of phase blocks is at least 500 kb. In some cases, the N50 of the population of phase blocks is at least 750 kb. In some cases, the N50 of the population of phase blocks is at least 1 Mb. In some cases, the N50 of the population of phase blocks is at least 1.75 Mb. In some cases, the N50 of the population of phase blocks is at least 2.5 Mb.

An additional aspect of the disclosure provides a method of determining a presence of a structural variation of a nucleic acid. The method can comprise: (a) providing a plurality of first fragment molecules of the nucleic acid, wherein a given first fragment molecule of the plurality of first fragment molecules comprises the structural variation; (b) sequencing a plurality of second fragment molecules of each of the plurality of first fragment molecules to provide a plurality of fragment sequences, wherein each of the plurality of fragment sequences corresponding to a given first fragment molecule shares a common barcode sequence; and (c) determining the presence of the structural variation by (i) mapping the plurality of fragment sequences to a reference sequence, (ii) identifying the plurality of fragment sequences that share the common barcode sequence, and (iii) identifying the structural variation based on a presence of an elevated amount of the plurality of fragment sequences sharing the common barcode sequence that map to the reference sequence at locations that are further apart than a length of the given first fragment molecule, which elevated amount is relative to a sequence lacking the structural variation.

In some cases, the elevated amount is 1% or more with respect to a total number of the first fragment molecules that are derived from a region of the nucleic acid having the structural variation. In some cases, the elevated amount is 2% or more with respect to the total number of the first fragment molecules that are derived from a region of the nucleic acid having the structural variation. In some cases, the locations are at least about 100 bases apart. In some cases, the locations are at least about 500 bases apart. In some cases, the locations are at least about 1 kilobase (kb) apart. In some cases, the locations are at least about 10 kb apart.

In some cases, the method of determining a presence of a structural variation of a nucleic acid further comprises identifying the structural variation by creating an assembly of the given first fragment molecule from the plurality of fragment sequences, wherein the plurality of fragment sequences are selected as inputs for the assembly based upon a presence of the common barcode sequence. In some cases, the assembly is created by generating a consensus sequence from the plurality of fragment sequences. In some cases, the structural variation comprises a translocation.

An additional aspect of the disclosure provides a method of characterizing a variant nucleic acid sequence. In some cases, the method can comprise: (a) fragmenting a variant nucleic acid to provide a plurality of first fragments having a length greater than 10 kilobases (kb); (b) separating the plurality of first fragments into discrete partitions; (c) creating a plurality of second fragments from each first fragment within its respective partition, the plurality of second fragments having a barcode sequence attached thereto, which barcode sequence within a given partition is a common barcode sequence; (d) sequencing the plurality of second fragments and the barcode sequences attached thereto, to provide a plurality of second fragment sequences; (e) attributing the second fragment sequences to an original first fragment based at least in part on the presence of the common barcode sequence to provide a first fragment sequence context for the second fragment sequences; and (f) identifying a variant portion of the variant nucleic acid from the first fragment sequence context, thereby characterizing the variant nucleic acid sequence. In some cases, the attributing comprises assembling at least a portion of a sequence for an individual fragment from the plurality of first fragments from the plurality of second fragment sequences based, at least in part, on the presence of the common barcode sequence. In some cases, the attributing comprises mapping the plurality of second fragment sequences to an individual first fragment from the plurality of first fragments based at least in part upon the common barcode sequence.

In some cases, the method of characterizing a variant nucleic acid sequence further comprises linking two or more of the plurality of first fragments into an inferred contig, based upon overlapping sequence between the two or more of the plurality of first fragments. In some cases, the identifying comprises identifying one or more phased variants from the first fragment sequence context. In some cases, the method of characterizing a variant nucleic acid sequence further comprises linking two or more of the plurality of first fragments into a phase block, based upon overlapping phased variants between the two or more of the plurality of first fragments. In some cases, the identifying comprises identifying one or more structural variations from the first fragment sequence context. In some cases, the one or more structural variations are independently selected from insertions, deletions, translocations, retrotransposons, inversions, and duplications. In some cases, the structural variation comprises an insertion or a translocation, and the first fragment sequence context indicates a presence of the insertion or translocation.

An additional aspect of the disclosure provides a method of identifying variants in a sequence of a nucleic acid. In some cases, the method comprises: obtaining nucleic acid sequences of a plurality of individual fragment molecules of the nucleic acid, the nucleic acid sequences of the plurality of individual fragment molecules each having a length of at least 1 kilobase (kb); linking sequences of one or more of the plurality of individual fragment molecules in one or more inferred contigs; and identifying one or more variants from the one or more inferred contigs. In some cases, the obtaining comprises obtaining the nucleic acid sequences of a plurality of fragment molecules that are greater than 10 kb in length. In some cases, the obtaining comprises: providing a plurality of barcoded fragments of each individual fragment molecule of the plurality of individual fragment molecules, the barcoded fragments of a given individual fragment molecule having a common barcode; sequencing the plurality of barcoded fragments of the plurality of individual fragment molecules, the sequencing providing a sequencing error rate of less than 1%; and determining a sequence of the plurality of individual fragment molecules from sequences of the plurality of barcoded fragments and their associated barcodes.

In some cases, the linking comprises identifying one or more overlapping sequences between two or more individual fragment molecules to link the two or more individual fragment molecules into the one or more inferred contigs. In some cases, the linking comprises identifying one or more common variants between two or more individual fragment molecules to link the two or more individual fragment molecules into the one or more inferred contigs. In some cases, the one or more common variants are phased variants, and the one or more inferred contigs comprise a maximum phase block length of at least 100 kb. In some cases, the one or more variants identified in the identifying comprise structural variations. In some cases, the structural variations are selected from insertions, deletions, translocations, retrotransposons, inversions, and duplications.

An additional aspect of the disclosure provides a method of characterizing nucleic acids. In some cases, the method comprises: obtaining nucleic acid sequences of a plurality of fragment molecules having a length of at least 10 kilobases (kb); identifying one or more phased variant positions in the nucleic acid sequences of the plurality of fragment molecules; linking the nucleic acid sequences of at least a first fragment molecule to at least a second fragment molecule based upon a presence of one or more common phased variant positions within the first and second fragment molecules, to provide a phase block with a maximum phase block length of at least 10 kb; and identifying one or more phased variants from the phase block with the maximum phase block length of at least 10 kb. In some cases, the method of characterizing nucleic acids further comprises identifying one or more additional phased variants from the phase block. In some cases, the plurality of fragment molecules are in discrete partitions. In some cases, the discrete partitions are droplets in an emulsion. In some cases, the length of the plurality of fragment molecules is at least 50 kb. In some cases, the length of the plurality of fragment molecules is at least 100 kb. In some cases, the maximum phase block length is at least 50 kb. In some cases, the maximum phase block length is at least 100 kb. In some cases, the maximum phase block length is at least 1 Mb. In some cases, the maximum phase block length is at least 2 Mb. In some cases, the maximum phase block length is at least 2.5 Mb.

An additional aspect of the disclosure provides a method comprising: (a) partitioning a first nucleic acid into a first partition, where the first nucleic acid comprises the target sequence derived from a first chromosome of an organism; (b) partitioning a second nucleic acid into a second partition, where the second nucleic acid comprises the target sequence derived from a second chromosome of the organism; (c) in the first partition, attaching a first barcode sequence to fragments of the first nucleic acid or to copies of portions of the first nucleic acid to provide first barcoded fragments; (d) in the second partition, attaching a second barcode sequence to fragments of the second nucleic acid or to copies of portions of the second nucleic acid to provide second barcoded fragments, the second barcode sequence being different from the first barcode sequence; (e) determining the nucleic acid sequence of the first and second barcoded fragments, and assembling a nucleic acid sequence of the first and second nucleic acids; and (f) comparing the nucleic acid sequence of the first and second nucleic acids to characterize the first and second nucleic acids as deriving from first and second chromosomes, respectively. In some cases, oligonucleotides comprising the first barcode sequence are co-partitioned with the first nucleic acid, and oligonucleotides comprising the second barcode sequence are co-partitioned with the second nucleic acid. In some cases, the oligonucleotides comprising the first barcode sequence are releasably attached to a first bead, and the oligonucleotides comprising the second barcode sequence are releasably attached to a second bead, and the co-partitioning comprises co-partitioning the first and second beads into the first and second partitions, respectively. In some cases, the first and second partitions comprise droplets in an emulsion. In some cases, the first chromosome is a paternal chromosome and the second chromosome is a maternal chromosome. In some cases, the first chromosome and the second chromosome are homologous chromosomes. In some cases, the first nucleic acid and the second nucleic acid comprise one or more variations.

In some cases, the first and second chromosomes are derived from a fetus. In some cases, the first and second nucleic acids are obtained from a sample taken from a pregnant woman. In some cases, the first chromosome is chromosome 21, 18, or 13. In some cases, the second chromosome is chromosome 21, 18, or 13. In some cases, the method further comprises determining the relative quantity of the first or second chromosome. In some cases, the method further comprises determining the quantity of the first or second chromosome relative to a reference chromosome. In some cases, the first chromosome or second chromosome, or both, has an increase in copy number. In some cases, the increase in copy number is a result of cancer or aneuploidy. In some cases, the first chromosome or second chromosome, or both, has a decrease in copy number. In some cases, the decrease in copy number is a result of cancer or aneuploidy.

An additional aspect of the disclosure provides a method comprising: (a) partitioning a first nucleic acid into a first partition, where the first nucleic acid comprises the target sequence derived from a first chromosome of an organism; (b) partitioning a second nucleic acid into a second partition, where the second nucleic acid comprises the target sequence derived from a second chromosome of the organism; (c) in the first partition, attaching a first barcode sequence to fragments of the first nucleic acid or to copies of portions of the first nucleic acid to provide first barcoded fragments; (d) in the second partition, attaching a second barcode sequence to fragments of the second nucleic acid or to copies of portions of the second nucleic acid to provide second barcoded fragments, the second barcode sequence being different from the first barcode sequence; (e) determining the nucleic acid sequence of the first and second barcoded fragments, and assembling a nucleic acid sequence of the first and second nucleic acids; and (f) comparing the nucleic acid sequence of the first and second nucleic acids to identify any variation between the nucleic acid sequence of the first and second nucleic acids. In some cases, oligonucleotides comprising the first barcode sequence are co-partitioned with the first nucleic acid, and oligonucleotides comprising the second barcode sequence are co-partitioned with the second nucleic acid. In some cases, the oligonucleotides comprising the first barcode sequence are releasably attached to a first bead, and the oligonucleotides comprising the second barcode sequence are releasably attached to a second bead, and the co-partitioning comprises co-partitioning the first and second beads into the first and second partitions, respectively. In some cases, the first and second partitions comprise droplets in an emulsion. In some cases, the first chromosome is a paternal chromosome and the second chromosome is a maternal chromosome. In some cases, first chromosome and the second chromosome are homologous chromosomes. In some cases, the first nucleic acid and the second nucleic acid comprise one or more variations. In some cases, the first and second chromosomes are derived from a fetus. In some cases, the first and second nucleic acids are obtained from a sample taken from a pregnant woman. In some cases, the first chromosome is chromosome 21, 18, or 13. In some cases, the second chromosome is chromosome 21, 18, or 13. In some cases, the method further comprises determining the relative quantity of the first or second chromosome. In some cases, the method further comprises determining the quantity of the first or second chromosome relative to a reference chromosome. In some cases, the first chromosome or second chromosome, or both, has an increase in copy number. In some cases, the increase in copy number is a result of cancer or aneuploidy. In some cases, the first chromosome or second chromosome, or both, has a decrease in copy number. In some cases, the decrease in copy number is a result of cancer or aneuploidy.

An additional aspect of the disclosure provides a method for characterizing a fetal nucleic acid sequence. In some cases, the method comprises: (a) determining a maternal nucleic acid sequence, wherein the maternal nucleic acid is derived from a pregnant mother of a fetus, by: (i) fragmenting a maternal nucleic acid to provide a plurality of first maternal fragments; (ii) separating the plurality of first maternal fragments into maternal partitions; (iii) creating a plurality of second maternal fragments from each of the first maternal fragments within their respective maternal partitions, the plurality of second maternal fragments having a first barcode sequence attached thereto, wherein within a given maternal partition of the maternal partitions the second maternal fragments comprise a first common barcode sequence attached thereto; (iv) sequencing the plurality of second maternal fragments to provide a plurality of maternal fragment sequences; (v) attributing the maternal fragment sequences to an original first maternal fragment based at least in part on the presence of the first common barcode sequence to determine the maternal nucleic acid sequence; (b) determining a paternal nucleic acid sequence, wherein the paternal nucleic acid is derived from a father of the fetus, by: (i) fragmenting a paternal nucleic acid to provide a plurality of first paternal fragments; (ii) separating the plurality of first paternal fragments into paternal discrete partitions; (iii) creating a plurality of second paternal fragments from each first paternal fragment within its respective partition, the plurality of second paternal fragments having a second barcode sequence attached thereto, wherein within a given paternal partition, the second paternal fragments comprise a second common barcode sequence attached thereto; (iv) sequencing the plurality of second paternal fragments and the second barcode sequences attached thereto, to provide a plurality of paternal fragment sequences; (v) attributing the paternal fragment sequences to an original first paternal fragment based at least in part on the presence of the second common barcode sequence to determine the paternal nucleic acid sequence; (c) obtaining a fetal nucleic acid from the pregnant mother and determining a sequence of the fetal nucleic acid and/or one or more genetic variations of the sequence of the fetal nucleic acid using the maternal nucleic acid sequence and the paternal nucleic acid sequence.

In some cases, the paternal fragment sequences and the maternal fragment sequences are each used to link sequences into one or more inferred contigs. In some cases, the inferred contigs are used to construct maternal and paternal phase blocks. In some cases, the sequence of the fetal nucleic acid is compared to the maternal and paternal phase blocks to construct fetal phase blocks. In some cases, the paternal fragment sequences are assembled to produce at least a portion of sequences for the plurality of first paternal fragments, thereby determining the paternal nucleic acid sequence, and wherein the maternal fragment sequences are assembled to produce at least a portion of sequences for the plurality of first maternal fragments, thereby determining the maternal nucleic acid sequence. In some cases, the determining the paternal nucleic acid sequence comprises mapping the paternal fragment sequences to a paternal reference, and wherein the determining the maternal nucleic acid sequence comprises mapping the maternal fragment sequences to a maternal reference.

In some cases, the sequence of the fetal nucleic acid is determined with an accuracy of at least 99%. In some cases, the one or more genetic variations of the sequence of the fetal nucleic acid are determined with an accuracy of at least 99%. In some cases, the one or more genetic variations are selected from the group consisting of a structural variation and a single nucleotide polymorphism (SNP). In some cases, the one or more genetic variations are a structural variation selected from the group consisting of a copy number variation, an insertion, a deletion, a translocation, a retrotransposon, an inversion, a rearrangement, a repeat expansion and a duplication.

In some cases, the method for characterizing the fetal nucleic acid sequence further comprises, in (c), determining the one or more genetic variations of the sequence of the fetal nucleic acid using one or more genetic variations determined for the maternal nucleic acid sequence and the paternal nucleic acid sequence. In some cases, the method for characterizing the fetal nucleic acid sequence further comprises, in (c), determining one or more de novo mutations of the fetal nucleic acid. In some cases, the method for characterizing the fetal nucleic acid sequence further comprises, during or after (c), determining an aneuploidy associated with the fetal nucleic acid.

In some cases, the method for characterizing the fetal nucleic acid sequence further comprises, during or after (v) in (a), haplotyping the maternal nucleic acid sequence to provide a haplotype-resolved maternal nucleic acid sequence and, during or after (v) in (b), haplotyping the paternal nucleic acid sequence to provide a haplotype-resolved paternal nucleic acid sequence. In some cases, the method for characterizing the fetal nucleic acid sequence further comprises in (c), determining the sequence of the fetal nucleic acid and/or the one or more genetic variations using the haplotype-resolved maternal nucleic acid sequence and the haplotype-resolved paternal nucleic acid sequence. In some cases, one or more of the maternal nucleic acid and the paternal nucleic acid is genomic deoxyribonucleic acid (DNA). In some cases, in (c), the fetal nucleic acid comprises cell-free nucleic acid. In some cases, the method for characterizing the fetal nucleic acid sequence further comprises, in (a), determining the maternal nucleic acid sequence with an accuracy of at least 99%. In some cases, the method for characterizing the fetal nucleic acid sequence further comprises, in (b), determining the paternal nucleic acid sequence with an accuracy of at least 99%.

In some cases, the maternal nucleic acid sequence and/or the paternal nucleic acid sequence has a length greater than 10 kilobases (kb). In some cases, the maternal and paternal partitions comprise droplets in an emulsion. In some cases, in (a), the first barcode sequence is provided in the given maternal partition releasably attached to a first particle. In some cases, in (b), the second barcode sequence is provided in the given paternal partition releasably attached to a second particle.

An additional aspect of the disclosure provides a method for characterizing a sample nucleic acid. In some cases, the method comprises: (a) obtaining a biological sample from a subject, which biological sample includes a cell-free sample nucleic acid; (b) in a droplet, attaching a barcode sequence to fragments of the cell-free sample nucleic acid or to copies of portions of the sample nucleic acid, to provide barcoded sample fragments; (c) determining nucleic acid sequences of the barcoded sample fragments and providing a sample nucleic acid sequence based on the nucleic acid sequences of the barcoded sample fragments; (d) using a programmed computer processor to generate a comparison of the sample nucleic acid sequence to a reference nucleic acid sequence, which reference nucleic acid sequence has a length greater 10 kilobases (kb) and an accuracy of at least 99%; and (e) using the comparison to identify one or more genetic variations in the sample nucleic acid sequence, thereby associating the sample nucleic acid with a disease. In some cases, the one or more genetic variations in the sample nucleic acid sequence are selected from the group consisting of a structural variation and a single nucleotide polymorphism (SNP). In some cases, the one or more genetic variations of the sample nucleic acid sequence are a structural variation selected from the group consisting of a copy number variation, an insertion, a deletion, a retrotransposon, a translocation, an inversion, a rearrangement, a repeat expansion and a duplication. In some cases, in (c), the sample nucleic acid sequence is provided with an accuracy of at least 99%. In some cases, in (b), the barcode sequence is provided in the droplet releasably attached to a particle, and wherein (b) further comprises releasing the barcode sequence from the particle into the droplet prior to the attaching the barcode sequence. In some cases, in (b), the barcode sequence is provided as a portion of a primer sequence releasably attached to the particle, wherein the primer sequence also includes a random N-mer sequence, and wherein (b) further comprises releasing the primer sequence from the particle into the droplet prior to the attaching the barcode sequence. In some cases, in (b), attaching the barcode sequence to the fragments of the cell-free sample nucleic acid or to the copies of portions of the cell-free sample nucleic acid in an amplification reaction using the primer.

In some cases, the method for characterizing the sample nucleic acid further comprises: (i) in an additional droplet, attaching an additional barcode sequence to fragments of a reference nucleic acid or to copies of portions of the reference nucleic acid to provide barcoded reference fragments; and (ii) determining nucleic acid sequences of the barcoded reference fragments and determining the reference nucleic acid sequence based on the nucleic acid sequences of the barcoded reference fragments. In some cases, the determining the reference nucleic acid sequence comprises assembling the nucleic acid sequences of the barcoded reference fragments. In some cases, the method for characterizing the sample nucleic acid further comprises providing the additional barcode sequence in the additional droplet releasably attached to a particle and releasing the additional barcode sequence from the particle into the additional partition prior to the attaching the additional barcode sequence. In some cases, the method for characterizing the sample nucleic acid further comprises providing the additional barcode sequence as a portion of a primer sequence releasably attached to the particle, wherein the primer sequence also includes a random N-mer sequence, and releasing the primer from the particle into the additional droplet prior to the attaching the additional barcode sequence. In some cases, the method for characterizing the sample nucleic acid further comprises attaching the additional barcode sequence to the fragments of the reference nucleic acid or to the copies of portions of the reference nucleic acid in an amplification reaction using the primer. In some cases, the method for characterizing the sample nucleic acid further comprises determining one or more genetic variations in the reference nucleic acid sequence.

In some cases, the one or more genetic variations in the reference nucleic acid sequence are selected from the group consisting of a structural variation and a single nucleotide polymorphism (SNP). In some cases, the one or more genetic variations in the reference nucleic acid sequence are a structural variation selected from the group consisting of a copy number variation, an insertion, a deletion, a retrotransposon, a translocation, an inversion, a rearrangement, a repeat expansion and a duplication. In some cases, the reference nucleic acid comprises a germline nucleic acid sequence. In some cases, the reference nucleic acid comprises a cancer nucleic acid sequence. In some cases, the sample nucleic acid sequence has a length of greater than 10 kb. In some cases, the reference nucleic acid is derived from a genome indicative of an absence of a disease state. In some cases, the reference nucleic acid is a derived from a genome indicative of a disease state. In some cases, the disease state comprises cancer. In some cases, the disease state comprises an aneuploidy. In some cases, the cell-free sample nucleic acid comprises tumor nucleic acid. In some cases, the tumor nucleic acid comprises a circulating tumor nucleic acid.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference in their entireties to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
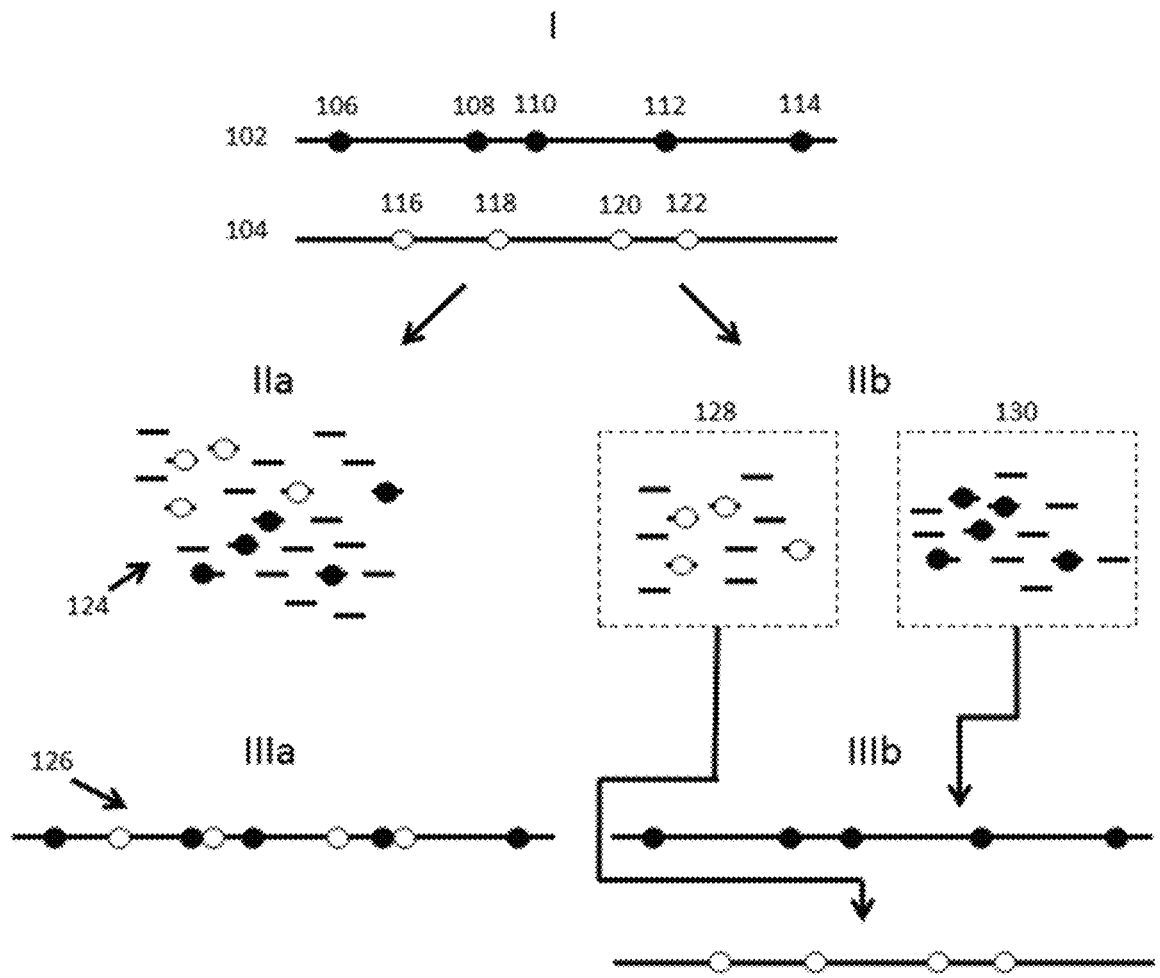
FIG. 1 provides a schematic illustration of identification and analysis of phased variants using conventional processes versus example processes and systems described herein.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

As used herein, the term "organism" generally refers to a contiguous living system. Non-limiting examples of organisms includes animals (e.g., humans, other types of mammals, birds, reptiles, insects, other example types of animals described elsewhere herein), plants, fungi and bacterium.

As used herein, the term "contig" generally refers to a contiguous nucleic acid sequence of a given length. The contiguous sequence may be derived from an individual sequence read, including either a short or long read sequence read, or from an assembly of sequence reads that are aligned and assembled based upon overlapping sequences within the reads, or that are defined as linked within a fragment based upon other known linkage data, e.g., the tagging with common barcodes as described elsewhere herein. These overlapping sequence reads may likewise include short reads, e.g., less than 500 bases, e.g., in some cases from approximately 100 to 500 bases, and in some cases from 100 to 250 bases, or based upon longer sequence reads, e.g., greater than 500 bases, 1000 bases or even greater than 10,000 bases.

I. Overview

This disclosure provides methods and systems useful in providing significant advances in the characterization of genetic material. In some cases, the methods and systems can be useful in providing genetic characterizations that are very difficult or even impossible using generally available technologies, including, for example, haplotype phasing, identifying structural variations, e.g., deletions, duplications, copy-number variants, insertions, inversions, retrotransposons, translocations, LTRs, STRs, and a variety of other useful characterizations.

In general, the methods and systems described herein accomplish the above goals by providing for the sequencing of long individual nucleic acid molecules, which permit the identification and use of long range variant information, e.g., relating variations to different sequence segments, including sequence segments containing other variations, that are separated by significant distances in the originating sequence, e.g., longer than is provided by short read sequencing technologies. However, these methods and systems achieve these objectives with the advantage of extremely low sequencing error rates of short read sequencing technologies, and far below those of the reported long read-length sequencing technologies, e.g., single molecule sequencing, such as SMRT Sequencing and nanopore sequencing technologies.

In general, the methods and systems described herein segment long nucleic acid molecules into smaller fragments that are sequenceable using high-throughput, higher accuracy short-read sequencing technologies, but do such segmentation in a manner that allows the sequence information derived from the smaller fragments to be attributed to the originating longer individual nucleic acid molecules. By attributing sequence reads to an originating longer nucleic acid molecule, one can gain significant characterization information for that longer nucleic acid sequence, that one cannot generally obtain from short sequence reads alone. As noted, such characterization information can include haplotype phasing, identification of structural variations, and identifying copy number variations.

The advantages of the methods and systems described herein are described with respect to a number of general examples. In a first example, phased sequence variants are identified and characterized using the methods and systems described herein. FIG. 1 schematically illustrates the challenges of phased variant calling and the solutions presented by the methods described herein. As shown, nucleic acids 102 and 104 in Panel I represent two haploid sequences of the same region of different chromosomes, e.g., maternally and paternally inherited chromosomes. Each sequence includes a series of variants, e.g., variants 106-114 on nucleic acid 102, and variants 116-122 on nucleic acid 104, at different alleles that characterize each haploid sequence. Because of their very short sequence reads, most sequencing technologies are unable to provide the context of individual variants relative to other variants on the same haploid sequence. Additionally, because they rely on sample preparation techniques that do not separate individual molecular components, e.g., each haploid sequence, one is unable to identify the phasing of the various variants, e.g., the haploid sequence from which a variant derives. As a result, these short read technologies are unable to resolve these variants to their originating molecules. The difficulties with this approach are schematically illustrated in Panels IIa and IIIa. Briefly, pooled fragments from both haploid sequences, shown in Panel IIa, are sequenced, resulting in a large number of short sequence reads 124, and the resulting sequence 126 is assembled (shown in Panel IIIa). As shown, because one does not have the relative phasing context of any of the shorter sequence reads in Panel IIa, one would be unable to resolve the variants as between two different haploid sequences in the assembly process. Accordingly, the resulting assembly shown in Panel IIIa, results in single consensus sequence assembly 126, including all of variants 106-122.

In contrast, and as shown in Panel IIb of FIG. 1, the methods and systems described herein breakdown or segment the longer nucleic acids 102 and 104 into shorter, sequenceable fragments, as with the above described approach, but retain with those fragments the ability to attribute them to their originating molecular context. This is schematically illustrated in Panel IIb, in which different fragments are grouped or "compartmentalized" according to their originating molecular context. In the context of the disclosure, this grouping can be accomplished through one or both of physically partitioning the fragments into groups that retain the molecular context, as well as tagging those fragments in order to subsequently be able to elucidate that context.

This grouping is schematically illustrated as the allocation of the shorter sequence reads as between groups 128 and 130, representing short sequence reads from nucleic acids 102 and 104, respectively. Because the originating sequence context is retained through the sequencing process, one can employ that context in resolving the original molecular context, e.g., the phasing, of the various variants 106-114 and 116-122 as between sequences 102 and 104, respectively.

In another exemplary advantaged application, the methods and systems are useful in characterizing structural variants that are generally unidentifiable or at least difficult to identify, using short read sequence technologies.

This is schematically illustrated with reference to a simple translocation event in FIG. 2. As shown, a genomic sample may include nucleic acids that include a translocation event, e.g., a translocation of genetic element 206 from sequence 202 to sequence 204. Such translocations may be any of a variety of different translocation types, including, for example, translocations between different chromosomes, whether to the same or different regions, between different regions of the same chromosome.

Again, as with the example illustrated in FIG. 1, above, conventional sequencing starts by breaking up the sequences 202 and 204 in Panel I into small fragments and producing short sequence reads 208 from those fragments, as shown in Panel IIa. Because these sequence fragments 208 are relatively short, the context of the translocated sequence 206, i.e., as originating from a variant location on the same or a different sequence, is easily lost during the assembly process. Further, because of their short read lengths, sequence assemblies are often predicated on the use of a reference sequence that would, almost by definition, not reflect structural variations. As such, the short sequence reads 208 would invariably be assembled to disregard the proper location of the translocated sequence 206, and would instead assemble the non-variant sequences 210 and 212, as shown in Panel IIIa.

In contrast, using the methods and systems described herein, the short sequence reads derived from sequences 202 and 204, are provided with a compartmentalization, shown in Panel IIb as groups 214 and 216, that retain the original molecular grouping of the smaller sequence fragments, allowing their assembly as sequences 218 and 220, shown in Panel IIIb, allowing attribution back to the originating sequences 202 and 204, and identification of the translocation variation, e.g., translocated sequence segment 206a in correct sequence assemblies 218 and 220, as illustrated in Panel IIb.

As noted above, the methods and systems described herein provide individual molecular context for short sequence reads of longer nucleic acids. As used herein, individual molecular context refers to sequence context beyond the specific sequence read, e.g., relation to adjacent or proximal sequences, that are not included within the sequence read itself, and as such, will generally be such that they would not be included in whole or in part in a short sequence read, e.g., a read of about 150 bases, or about 300 bases for paired reads. In some aspects, the methods and systems provide long range sequence context for short sequence reads. Such long range context includes relationship or linkage of a given sequence read to sequence reads that are within a distance of each other of longer than 1 kilobase (kb), longer than 5 kb, longer than 10 kb, longer than 15 kb, longer than 20 kb, longer than 30 kb, longer than 40 kb, longer than 50 kb, longer than 60 kb, longer than 70 kb, longer than 80 kb, longer than 90 kb or even longer than 100 kb, or longer. By providing longer range individual molecular context, the methods and systems described herein also provide much longer inferred molecular context. Sequence context, as described herein can include lower resolution context, e.g., from mapping the short sequence reads to the individual longer molecules or contigs of linked molecules, as well as the higher resolution sequence context, e.g., from long range sequencing of large portions of the longer individual molecules, e.g., having contiguous determined sequences of individual molecules where such determined sequences are longer than 1 kb, longer than 5 kb, longer than 10 kb, longer than 15 kb, longer than 20 kb, longer than 30 kb, longer than 40 kb, longer than 50 kb, longer than 60 kb, longer than 70 kb, longer than 80 kb, longer than 90 kb or even longer than 100 kb. As with sequence context, the attribution of short sequences to longer nucleic acids, e.g., both individual long nucleic acid molecules or collections of linked nucleic acid molecules or contigs, may include both mapping of short sequences against longer nucleic acid stretches to provide high level sequence context, as well as providing assembled sequences from the short sequences through these longer nucleic acids.

Furthermore, while one may utilize the long range sequence context associated with long individual molecules, having such long range sequence context also allows one to infer even longer range sequence context. By way of one example, by providing the long range molecular context described above, one can identify overlapping variant portions, e.g., phased variants, translocated sequences, etc., among long sequences from different originating molecules, allowing the inferred linkage between those molecules. Such inferred linkages or molecular contexts are referred to herein as "inferred contigs". In some cases when discussed in the context of phased sequences, the inferred contigs may represent commonly phased sequences, e.g., where by virtue of overlapping phased variants, one can infer a phased contig of substantially greater length than the individual originating molecules. These phased contigs are referred to herein as "phase blocks".

By starting with longer single molecule reads, one can derive longer inferred contigs or phase blocks than would otherwise be attainable using short read sequencing technologies or other approaches to phased sequencing. See, e.g., published U.S. Patent Publication No. 2013/0157870, the full disclosure of which is herein incorporated by reference in its entirety. In particular, using the methods and systems described herein, one can obtain inferred contig or phase block lengths having an N50 (the contig or phase block length for which the collection of all phase blocks or contigs of that length or longer contain at least half of the sum of the lengths of all contigs or phase blocks, and for which the collection of all contigs or phase blocks of that length or shorter also contains at least half the sum of the lengths of all contigs or phase blocks), mode, mean, or median of at least about 10 kilobases (kb), at least about 20 kb, at least about 50 kb. In some aspects, inferred contig or phase block lengths have an N50, mode, mean, or median of at least about 100 kb, at least about 150 kb, at least about 200 kb, and in some cases, at least about 250 kb, at least about 300 kb, at least about 350 kb, at least about 400 kb, and in some cases, at least about 500 kb, at least about 750 kb, at least about 1 Mb, at least about 1.75 Mb, at least about 2.5 Mb or more, are attained. In still other cases, maximum inferred contig or phase block lengths of at least or in excess of 20 kb, 40 kb, 50 kb, 100 kb, 200 kb, 300 kb, 400 kb, 500 kb, 750 kb, 1 megabase (Mb), 1.75 Mb, 2 Mb or 2.5 Mb may be obtained. In still other cases, inferred contigs or phase blocks lengths can be at least about 20 kb, at least about 40 kb, at least about 50 kb, at least about 100 kb, at least about 200 kb, and in some cases, at least about 500 kb, at least about 750 kb, at least about 1 Mb, and in some cases at least about 1.75 Mb, at least about 2.5 Mb or more.

In one aspect, the methods and systems described herein provide for the compartmentalization, depositing or partitioning of sample nucleic acids, or fragments thereof, into discrete compartments or partitions (referred to interchangeably herein as partitions), where each partition maintains separation of its own contents from the contents of other partitions. Unique identifiers, e.g., barcodes, may be previously, subsequently or concurrently delivered to the partitions that hold the compartmentalized or partitioned sample nucleic acids, in order to allow for the later attribution of the characteristics, e.g., nucleic acid sequence information, to the sample nucleic acids included within a particular compartment, and particularly to relatively long stretches of contiguous sample nucleic acids that may be originally deposited into the partitions.

The sample nucleic acids can be partitioned such that the nucleic acids are present in the partitions in relatively long fragments or stretches of contiguous nucleic acid molecules. These fragments can represent a number of overlapping fragments of the overall sample nucleic acids to be analyzed, e.g., an entire chromosome, exome, or other large genomic fragment. These sample nucleic acids may include whole genomes, individual chromosomes, exomes, amplicons, or any of a variety of different nucleic acids of interest. In some cases, these fragments of the sample nucleic acids may be longer than 100 bases, longer 500 bases, longer than 1 kb, longer than 5 kb, longer than 10 kb, longer than 15 kb, longer than 20 kb, longer than 30 kb, longer than 40 kb, longer than 50 kb, longer than 60 kb, longer than 70 kb, longer than 80 kb, longer than 90 kb or even longer than 100 kb, which permits the longer range molecular context described above.

The sample nucleic acids can also be partitioned at a level whereby a given partition has a very low probability of including two overlapping fragments of the starting sample nucleic acid. This can be accomplished by providing the sample nucleic acid at a low input amount and/or concentration during the partitioning process. As a result, in some cases, a given partition may include a number of long, but non-overlapping fragments of the starting sample nucleic acids. The sample nucleic acids in the different partitions are then associated with unique identifiers, where for any given partition, nucleic acids contained therein possess the same unique identifier, but where different partitions may include different unique identifiers. Moreover, because the partitioning allocates the sample components into very small volume partitions or droplets, it will be appreciated that in order to achieve the allocation as set forth above, one need not conduct substantial dilution of the sample, as would can be required in higher volume processes, e.g., in tubes, or wells of a multiwell plate. Further, because the systems described herein employ such high levels of barcode diversity, one can allocate diverse barcodes among higher numbers of genomic equivalents, as provided above. In particular, previously described, multiwell plate approaches (see, e.g., U.S. Patent Publication No. 2013/0079231 and 2013/0157870, the full disclosures of which are herein incorporated by reference in their entireties) may only operate with a hundred to a few hundred different barcode sequences, and employ a limiting dilution process of their sample in order to be able to attribute barcodes to different cells/nucleic acids. As such, they generally operate with far fewer than 100 cells, which would can provide a ratio of genomes: (barcode type) on the order of 1:10, and certainly well above 1:100. The systems described herein, on the other hand, because of the high level of barcode diversity, e.g., in excess of 10,000, 100,000, 500,000, etc. diverse barcode types, can operate at genome: (barcode type) ratios that are on the order of 1:50 or less, 1:100 or less, 1:1000 or less, or even smaller ratios, while also allowing for loading higher numbers of genomes (e.g., on the order of greater than 100 genomes per assay, greater than 500 genomes per assay, 1000 genomes per assay, or even more) while still providing for far improved barcode diversity per genome.

Often, the sample is combined with a set of oligonucleotide tags that are releasably-attached to beads prior to the partitioning. The oligonucleotides may comprise at least a first and second region. The first region may be a barcode region that, as between oligonucleotides within a given partition, may be substantially the same barcode sequence, but as between different partitions, may and, in most cases is a different barcode sequence. The second region may be a an N-mer (e.g., either a random N-mer or an N-mer designed to target a particular sequence) that can be used to prime the nucleic acids within the sample within the partitions. In some cases, where the N-mer is designed to target a particular sequence, it may be designed to target a particular chromosome (e.g., chromosome 1, 13, 18, or 21), or region of a chromosome, an exome or other targeted region. In some cases, the N-mer may be designed to target a particular gene or genetic region, such as a gene or region associated with a disease or disorder (e.g., cancer). Within the partitions, an amplification reaction may be conducted using the second N-mer to prime the nucleic acid sample at different places along the length of the nucleic acid. As a result of the amplification, each partition may contain amplified products of the nucleic acid that are attached to an identical or near-identical barcode, and that may represent overlapping, smaller fragments of the nucleic acids in each partition. The bar-code can serve as a marker that signifies that a set of nucleic acids originated from the same partition, and thus potentially also originated from the same strand of nucleic acid. Following amplification, the nucleic acids may be pooled, sequenced, and aligned using a sequencing algorithm. Because shorter sequence reads may, by virtue of their associated barcode sequences, be aligned and attributed to a single, long fragment of the sample nucleic acid, all of the identified variants on that sequence can be attributed to a single originating fragment and single originating chromosome. Further, by aligning multiple co-located variants across multiple long fragments, one can further characterize that chromosomal contribution. Accordingly, conclusions regarding the phasing of particular genetic variants may then be drawn. Such information may be useful for identifying haplotypes, which are generally a specified set of genetic variants that reside on the same nucleic acid strand or on different nucleic acid strands. Copy number variations may also be identified in this manner.

The described methods and systems provide significant advantages over current nucleic acid sequencing technologies and their associated sample preparation methods. Haplotype phasing and copy number variation data are generally not available by sequencing genomic DNA because biological samples (blood, cells, or tissue samples, for example) are processed en masse to extract the genetic material from an ensemble of cells, and convert it into sequencing libraries that are configured specifically for a given sequencing technology. As a result of this ensemble sample processing approach, sequencing data generally provides non-phased genotypes, in which it is not possible to determine whether genetic information is present on the same or different chromosomes.

In addition to the inability to attribute genetic characteristics to a particular chromosome, such ensemble sample preparation and sequencing methods are also predisposed towards primarily identifying and characterizing the majority constituents in the sample, and are not designed to identify and characterize minority constituents, e.g., genetic material contributed by one chromosome, or by one or a few cells, or fragmented tumor cell DNA molecule circulating in the bloodstream, that constitute a small percentage of the total DNA in the extracted sample. The described methods and systems also provide a significant advantage for detecting minor populations that are present in a larger sample. As such, they can be useful for assessing copy number variations in a sample since often only a small portion of a clinical sample contains tissue with copy number variations. For example, if the sample is a blood sample from a pregnant woman, only a small fraction of the sample would contain circulating cell-free fetal DNA.

The use of the barcoding technique disclosed herein confers the unique capability of providing individual molecular context for a given set of genetic markers, i.e., attributing a given set of genetic markers (as opposed to a single marker) to individual sample nucleic acid molecules, and through variant coordinated assembly, to provide a broader or even longer range inferred individual molecular context, among multiple sample nucleic acid molecules, and/or to a specific chromosome. These genetic markers may include specific genetic loci, e.g., variants, such as SNPs, or they may include short sequences. Furthermore, the use of barcoding confers the additional advantages of facilitating the ability to discriminate between minority constituents and majority constituents of the total nucleic acid population extracted from the sample, e.g. for detection and characterization of circulating tumor DNA in the bloodstream, and also reduces or eliminates amplification bias during any amplification. In addition, implementation in a microfluidics format confers the ability to work with extremely small sample volumes and low input quantities of DNA, as well as the ability to rapidly process large numbers of sample partitions (e.g., droplets) to facilitate genome-wide tagging.

As described previously, an advantage of the methods and systems described herein is that they can achieve results through the use of ubiquitously available, short read sequencing technologies. Such technologies have the advantages of being readily available and widely dispersed within the research community, with protocols and reagent systems that are well characterized and highly effective. These short read sequencing technologies include those available from, e.g., Illumina, Inc. (e.g., GXII, NextSeq, MiSeq, HiSeq, X10), Ion Torrent division of Thermo-Fisher (e.g., Ion Proton and Ion PGM), pyrosequencing methods, as well as others.

Of particular advantage is that the methods and systems described herein utilize these short read sequencing technologies and do so with their associated low error rates. In particular, the methods and systems described herein achieve individual molecular read lengths or context, as described above, but with individual sequencing reads, excluding mate pair extensions, that are shorter than 1000 bp, shorter than 500 bp, shorter than 300 bp, shorter than 200 bp, shorter than 150 bp or even shorter; and with sequencing error rates for such individual molecular read lengths that are less than 5%, less than 1%, less than 0.5%, less than 0.1%, less than 0.05%, less than 0.01%, less than 0.005%, or even less than 0.001%.

II. Work Flow Overview

In one exemplary aspect, the methods and systems described in the disclosure provide for depositing or partitioning individual samples (e.g., nucleic acids) into discrete partitions, where each partition maintains separation of its own contents from the contents in other partitions. As used herein, the partitions refer to containers or vessels that may include a variety of different forms, e.g., wells, tubes, micro or nanowells, through holes, or the like. In some aspects, however, the partitions are flowable within fluid streams. These vessels may be comprised of, e.g., microcapsules or micro-vesicles that have an outer barrier surrounding an inner fluid center or core, or they may be a porous matrix that is capable of entraining and/or retaining materials within its matrix. In some aspects, however, these partitions may comprise droplets of aqueous fluid within a non-aqueous continuous phase, e.g., an oil phase. A variety of different vessels are described in, for example, U.S. patent application Ser. No. 13/966,150, filed Aug. 13, 2013. Likewise, emulsion systems for creating stable droplets in non-aqueous or oil continuous phases are described in detail in, e.g., U.S. Patent Publication No. 2010/0105112, the full disclosure of which is herein incorporated by reference in its entirety. In certain cases, microfluidic channel networks can be suited for generating partitions as described herein. Examples of such microfluidic devices include those described in detail in U.S. Provisional Patent Application No. 61/977,804, filed Apr. 10, 2014, the full disclosure of which is incorporated herein by reference in its entirety for all purposes. Alternative mechanisms may also be employed in the partitioning of individual cells, including porous membranes through which aqueous mixtures of cells are extruded into non-aqueous fluids. Such systems are generally available from, e.g., Nanomi, Inc.

In the case of droplets in an emulsion, partitioning of sample materials, e.g., nucleic acids, into discrete partitions may generally be accomplished by flowing an aqueous, sample containing stream, into a junction into which is also flowing a non-aqueous stream of partitioning fluid, e.g., a fluorinated oil, such that aqueous droplets are created within the flowing stream partitioning fluid, where such droplets include the sample materials. As described below, the partitions, e.g., droplets, can also include co-partitioned barcode oligonucleotides. The relative amount of sample materials within any particular partition may be adjusted by controlling a variety of different parameters of the system, including, for example, the concentration of sample in the aqueous stream, the flow rate of the aqueous stream and/or the non-aqueous stream, and the like. The partitions described herein are often characterized by having extremely small volumes. For example, in the case of droplet based partitions, the droplets may have overall volumes that are less than 1000 picoliters (pL), less than 900 pL, less than 800 pL, less than 700 pL, less than 600 pL, less than 500 pL, less than 400pL, less than 300 pL, less than 200 pL, less than 100pL, less than 50 pL, less than 20 pL, less than 10 pL, or even less than 1 pL. Where co-partitioned with beads, it will be appreciated that the sample fluid volume within the partitions may be less than 90% of the above described volumes, less than 80%, less than 70%, less than 60%, less than 50%, less than 40%, less than 30%, less than 20%, or even less than 10% the above described volumes. In some cases, the use of low reaction volume partitions can be advantageous in performing reactions with very small amounts of starting reagents, e.g., input nucleic acids. Methods and systems for analyzing samples with low input nucleic acids are presented in U.S. Provisional Patent Application No. 62/017,580, filed Jun. 26, 2014, the full disclosure of which is hereby incorporated by reference in its entirety.

Once the samples are introduced into their respective partitions, in accordance with the methods and systems described herein, the sample nucleic acids within partitions are generally provided with unique identifiers such that, upon characterization of those nucleic acids they may be attributed as having been derived from their respective origins. Accordingly, the sample nucleic acids can be co-partitioned with the unique identifiers (e.g., barcode sequences). In some aspects, the unique identifiers are provided in the form of oligonucleotides that comprise nucleic acid barcode sequences that may be attached to those samples. The oligonucleotides are partitioned such that as between oligonucleotides in a given partition, the nucleic acid barcode sequences contained therein are the same, but as between different partitions, the oligonucleotides can have differing barcode sequences. In some aspects, only one nucleic acid barcode sequence may be associated with a given partition, although in some cases, two or more different barcode sequences may be present.

The nucleic acid barcode sequences can include from 6 to about 20 or more nucleotides within the sequence of the oligonucleotides. These nucleotides may be completely contiguous, i.e., in a single stretch of adjacent nucleotides, or they may be separated into two or more separate subsequences that are separated by one or more nucleotides. In some cases, separated subsequences may be from about 4 to about 16 nucleotides in length.

The co-partitioned oligonucleotides can also comprise other functional sequences useful in the processing of the partitioned nucleic acids. These sequences include, e.g., targeted or random/universal amplification primer sequences for amplifying the genomic DNA from the individual nucleic acids within the partitions while attaching the associated barcode sequences, sequencing primers, hybridization or probing sequences, e.g., for identification of presence of the sequences, or for pulling down barcoded nucleic acids, or any of a number of other potential functional sequences. Again, co-partitioning of oligonucleotides and associated barcodes and other functional sequences, along with sample materials is described in, for example, U.S. Provisional Patent Application No. 61/940,318, filed Feb. 7, 2014, U.S. Provisional Patent Application No.

61/991,018, Filed May 9, 2014, and U.S. patent application Ser. No. 14/316,383, filed on Jun. 26, 2014, as well as U.S. patent application Ser. No. 14/175,935, filed Feb. 7, 2014, the full disclosures of which is hereby incorporated by reference in their entireties.

Briefly, in one exemplary process, beads are provided that each may include large numbers of the above described oligonucleotides releasably attached to the beads, where all of the oligonucleotides attached to a particular bead may include the same nucleic acid barcode sequence, but where a large number of diverse barcode sequences may be represented across the population of beads used. In some cases, the population of beads may provide a diverse barcode sequence library that may include at least 1000 different barcode sequences, at least 10,000 different barcode sequences, at least 100,000 different barcode sequences, or in some cases, at least 1,000,000 different barcode sequences. Additionally, each bead may be provided with large numbers of oligonucleotide molecules attached. In particular, the number of molecules of oligonucleotides including the barcode sequence on an individual bead may be at least bout 10,000 oligonucleotides, at least 100,000 oligonucleotide molecules, at least 1,000,000 oligonucleotide molecules, at least 100,000,000 oligonucleotide molecules, and in some cases at least 1 billion oligonucleotide molecules.

The oligonucleotides may be releasable from the beads upon the application of a particular stimulus to the beads. In some cases, the stimulus may be a photo-stimulus, e.g., through cleavage of a photo-labile linkage that may release the oligonucleotides. In some cases, a thermal stimulus may be used, where elevation of the temperature of the beads environment may result in cleavage of a linkage or other release of the oligonucleotides form the beads. In some cases, a chemical stimulus may be used that cleaves a linkage of the oligonucleotides to the beads, or otherwise may result in release of the oligonucleotides from the beads.

In accordance with the methods and systems described herein, the beads including the attached oligonucleotides may be co-partitioned with the individual samples, such that a single bead and a single sample are contained within an individual partition. In some cases, where single bead partitions are desired, the relative flow rates of the fluids can be controlled such that, on average, the partitions contain less than one bead per partition, in order to ensure that those partitions that are occupied, are primarily singly occupied. Likewise, one may wish to control the flow rate to provide that a higher percentage of partitions are occupied, e.g., allowing for only a small percentage of unoccupied partitions. In some aspects, the flows and channel architectures are controlled as to ensure a desired number of singly occupied partitions, less than a certain level of unoccupied partitions and less than a certain level of multiply occupied partitions.

Figure 3:
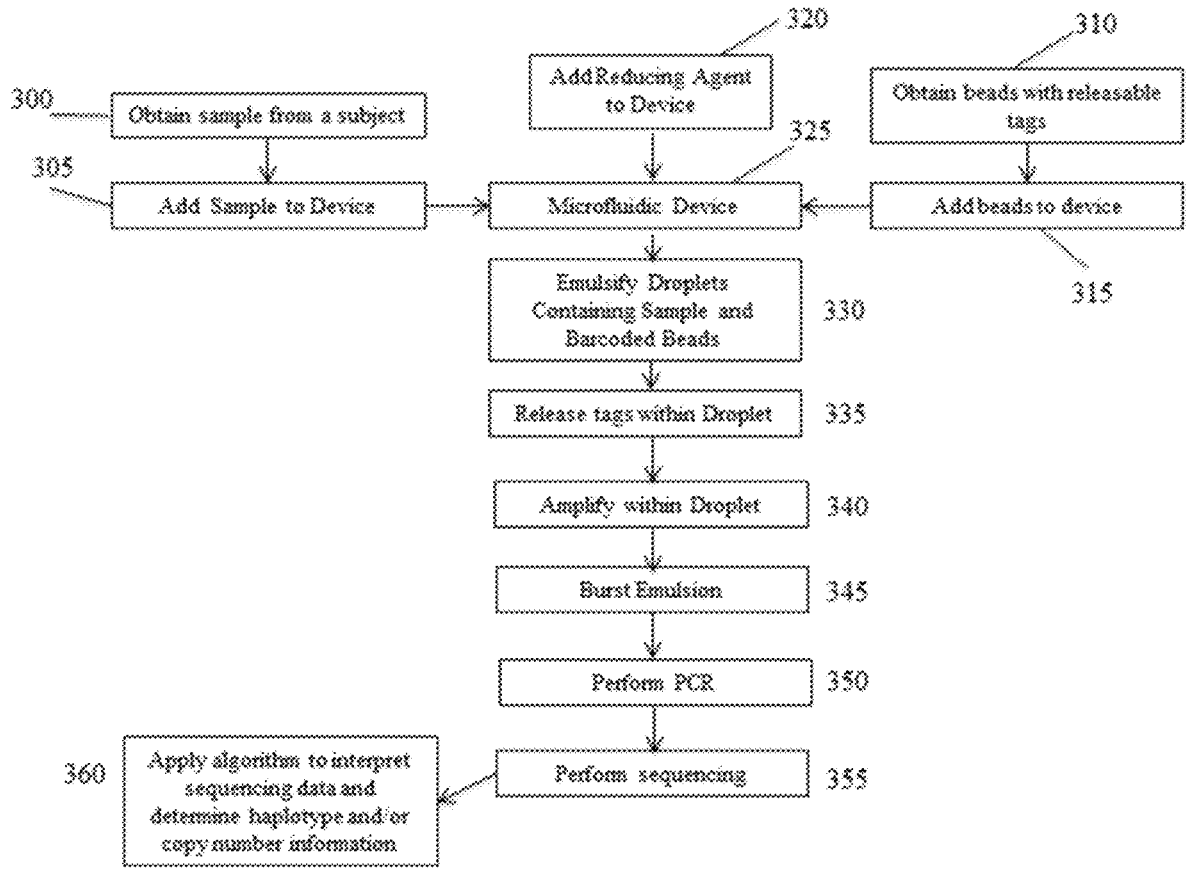
FIG. 3 illustrates an example workflow for performing an assay to detect copy number or haplotype using methods and compositions disclosed herein.

FIG. 3 illustrates an example method for barcoding and subsequently sequencing a sample nucleic acid, such as for use for a copy number variation or haplotype assay. First, a sample comprising nucleic acid may be obtained from a source, 300, and a set of barcoded beads may also be obtained, 310. The beads can be linked to oligonucleotides containing one or more barcode sequences, as well as a primer, such as a random N-mer or other primer. In some cases, the barcode sequences are releasable from the barcoded beads, e.g., through cleavage of a linkage between the barcode and the bead or through degradation of the underlying bead to release the barcode, or a combination of the two. For example, in some aspects, the barcoded beads can be degraded or dissolved by an agent, such as a reducing agent to release the barcode sequences. In this example, a low quantity of the sample comprising nucleic acid, 305, barcoded beads, 315, and, in some cases, other reagents, e.g., a reducing agent, 320, are combined and subject to partitioning. By way of example, such partitioning may involve introducing the components to a droplet generation system, such as a microfluidic device, 325. With the aid of the microfluidic device 325, a water-in-oil emulsion 330 may be formed, where the emulsion contains aqueous droplets that contain sample nucleic acid, 305, reducing agent, 320, and barcoded beads, 315. The reducing agent may dissolve or degrade the barcoded beads, thereby releasing the oligonucleotides with the barcodes and random N-mers from the beads within the droplets, 335. The random N-mers may then prime different regions of the sample nucleic acid, resulting in amplified copies of the sample after amplification, where each copy is tagged with a barcode sequence, 340. In some cases, each droplet contains a set of oligonucleotides that contain identical barcode sequences and different random N-mer sequences. Subsequently, the emulsion is broken, 345 and additional sequences (e.g., sequences that aid in particular sequencing methods, additional barcodes, etc.) may be added, via, for example, amplification methods, 350 (e.g., PCR). Sequencing may then be performed, 355, and an algorithm applied to interpret the sequencing data, 360. Sequencing algorithms are generally capable, for example, of performing analysis of barcodes to align sequencing reads and/or identify the sample from which a particular sequence read belongs.

Figure 4:
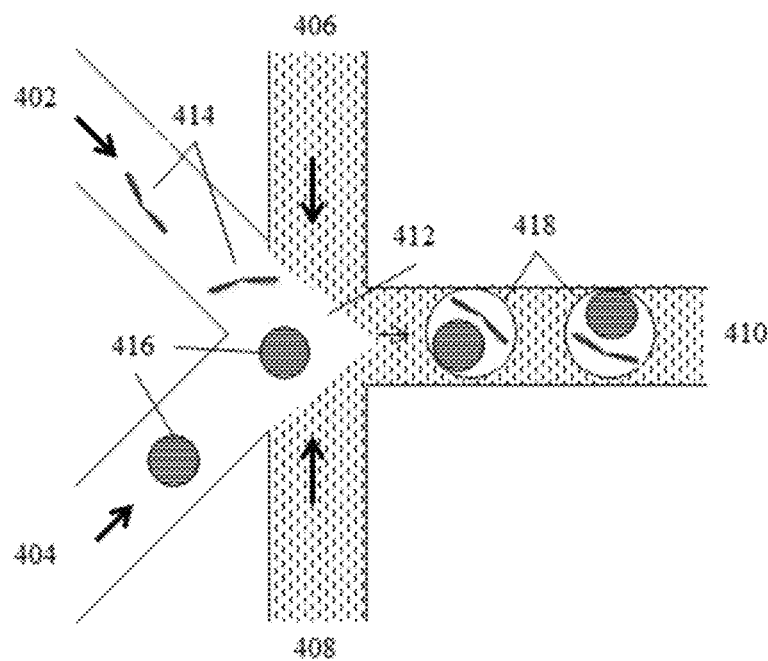
FIG. 4 provides a schematic illustration of an example process for combining a nucleic acid sample with beads and partitioning the nucleic acids and beads into discrete droplets FIG. 5 provides a schematic illustration of an example process for barcoding and amplification of chromosomal nucleic acid fragments.

As noted above, while single bead occupancy may be desired, it will be appreciated that multiply occupied partitions, or unoccupied partitions may often be present. An example of a microfluidic channel structure for co-partitioning samples and beads comprising barcode oligonucleotides is schematically illustrated in FIG. 4. As shown, channel segments 402, 404, 406, 408 and 410 are provided in fluid communication at channel junction 412. An aqueous stream comprising the individual samples 414 is flowed through channel segment 402 toward channel junction 412. As described elsewhere herein, these samples may be suspended within an aqueous fluid prior to the partitioning process.

Concurrently, an aqueous stream comprising the barcode carrying beads 416 is flowed through channel segment 404 toward channel junction 412. A non-aqueous partitioning fluid is introduced into channel junction 412 from each of side channels 406 and 408, and the combined streams are flowed into outlet channel 410. Within channel junction 412, the two combined aqueous streams from channel segments 402 and 404 are combined, and partitioned into droplets 418, that include co-partitioned samples 414 and beads 416. As noted previously, by controlling the flow characteristics of each of the fluids combining at channel junction 412, as well as controlling the geometry of the channel junction, one can optimize the combination and partitioning to achieve a desired occupancy level of beads, samples or both, within the partitions 418 that are generated.

As will be appreciated, a number of other reagents may be co-partitioned along with the samples and beads, including, for example, chemical stimuli, nucleic acid extension, transcription, and/or amplification reagents such as polymerases, reverse transcriptases, nucleoside triphosphates or NTP analogues, primer sequences and additional cofactors such as divalent metal ions used in such reactions, ligation reaction reagents, such as ligase enzymes and ligation sequences, dyes, labels, or other tagging reagents.

Once co-partitioned, the oligonucleotides disposed upon the bead may be used to barcode and amplify the partitioned samples. An example process for use of these barcode oligonucleotides in amplifying and barcoding samples is described in detail in U.S. Patent Application No. 61/940,318, filed Feb. 7, 2014, U.S. Provisional Patent Application No. 61/991,018, Filed May 9, 2014, and U.S. patent application Ser. No. 14/316,383, filed on Jun. 26, 2014, the full disclosures of which are hereby incorporated by reference in their entireties. Briefly, in one aspect, the oligonucleotides present on the beads that are co-partitioned with the samples and released from their beads into the partition with the samples. The oligonucleotides can include, along with the barcode sequence, a primer sequence at its 5' end. This primer sequence may be a random oligonucleotide sequence intended to randomly prime numerous different regions of the samples, or it may be a specific primer sequence targeted to prime upstream of a specific targeted region of the sample.

Figure 5:
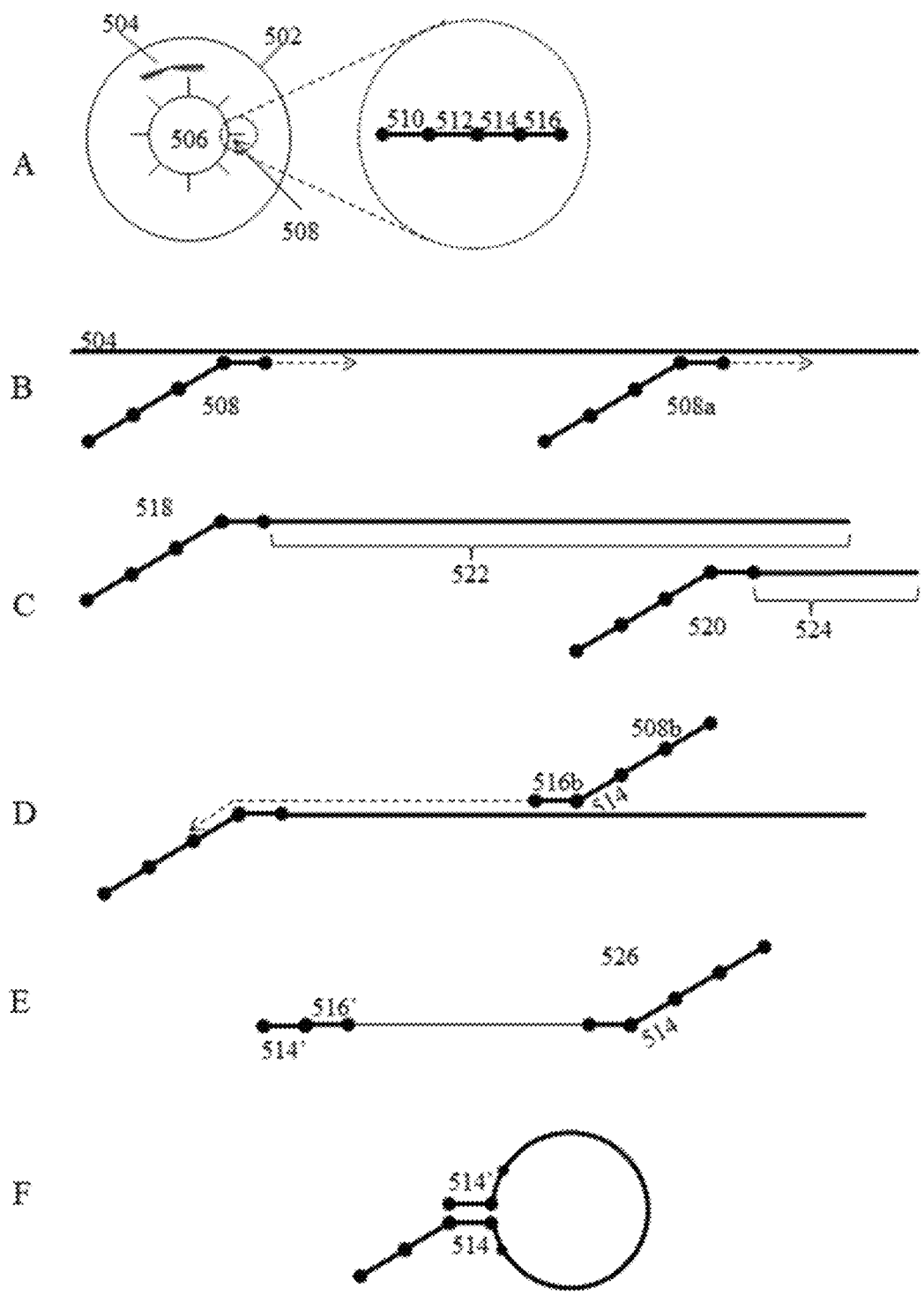

Once released, the primer portion of the oligonucleotide can anneal to a complementary region of the sample. Extension reaction reagents, e.g., DNA polymerase, nucleoside triphosphates, co-factors (e.g., $Mg^{2+}$ or $Mn^{2+}$ etc.), that are also co-partitioned with the samples and beads, then extend the primer sequence using the sample as a template, to produce a complementary fragment to the strand of the template to which the primer annealed, with complementary fragment includes the oligonucleotide and its associated barcode sequence. Annealing and extension of multiple primers to different portions of the sample may result in a large pool of overlapping complementary fragments of the sample, each possessing its own barcode sequence indicative of the partition in which it was created. In some cases, these complementary fragments may themselves be used as a template primed by the oligonucleotides present in the partition to produce a complement of the complement that again, includes the barcode sequence. In some cases, this replication process is configured such that when the first complement is duplicated, it produces two complementary sequences at or near its termini, to allow the formation of a hairpin structure or partial hairpin structure, that reduces the ability of the molecule to be the basis for producing further iterative copies. A schematic illustration of one example of this is shown in FIG. 5.

As the figure shows, oligonucleotides that include a barcode sequence are co-partitioned in, e.g., a droplet 502 in an emulsion, along with a sample nucleic acid 504. As noted elsewhere herein, the oligonucleotides 508 may be provided on a bead 506 that is co-partitioned with the sample nucleic acid 504, which oligonucleotides can be releasable from the bead 506, as shown in panel A. The oligonucleotides 508 include a barcode sequence 512, in addition to one or more functional sequences, e.g., sequences 510, 514 and 516. For example, oligonucleotide 508 is shown as comprising barcode sequence 512, as well as sequence 510 that may function as an attachment or immobilization sequence for a given sequencing system, e.g., a P5 sequence used for attachment in flow cells of an Illumina Hiseq or Miseq system. As shown, the oligonucleotides also include a primer sequence 516, which may include a random or targeted N-mer for priming replication of portions of the sample nucleic acid 504. Also included within oligonucleotide 508 is a sequence 514 which may provide a sequencing priming region, such as a "read1" or R1 priming region, that is used to prime polymerase mediated, template directed sequencing by synthesis reactions in sequencing systems. In some cases, the barcode sequence 512, immobilization sequence 510 and sequence 514 may be common to all of the oligonucleotides attached to a given bead. The primer sequence 516 may vary for random N-mer primers, or may be common to the oligonucleotides on a given bead for certain targeted applications.

Based upon the presence of primer sequence 516, the oligonucleotides are able to prime the sample nucleic acid as shown in panel B, which allows for extension of the oligonucleotides 508 and 508a using polymerase enzymes and other extension reagents also co-portioned with the bead 506 and sample nucleic acid 504. As shown in panel C, following extension of the oligonucleotides that, for random N-mer primers, would anneal to multiple different regions of the sample nucleic acid 504; multiple overlapping complements or fragments of the nucleic acid are created, e.g., fragments 518 and 520. Although including sequence portions that are complementary to portions of sample nucleic acid, e.g., sequences 522 and 524, these constructs are generally referred to herein as comprising fragments of the sample nucleic acid 504, having the attached barcode sequences. As will be appreciated, the replicated portions of the template sequences as described above are often referred to herein as "fragments" of that template sequence. Notwithstanding the foregoing, however, the term "fragment" encompasses any representation of a portion of the originating nucleic acid sequence, e.g., a template or sample nucleic acid, including those created by other mechanisms of providing portions of the template sequence, such as actual fragmentation of a given molecule of sequence, e.g., through enzymatic, chemical or mechanical fragmentation. In some aspects, however, fragments of a template or sample nucleic acid sequence may denote replicated portions of the underlying sequence or complements thereof The barcoded nucleic acid fragments may then be subjected to characterization, e.g., through sequence analysis, or they may be further amplified in the process, as shown in panel D. For example, additional oligonucleotides, e.g., oligonucleotide 508b, also released from bead 306, may prime the fragments 518 and 520. In particular, again, based upon the presence of the random N-mer primer 516b in oligonucleotide 508b (which in some cases can be different from other random N-mers in a given partition, e.g., primer sequence 516), the oligonucleotide anneals with the fragment 518, and is extended to create a complement 526 to at least a portion of fragment 518 which includes sequence 528, that comprises a duplicate of a portion of the sample nucleic acid sequence. Extension of the oligonucleotide 508b continues until it has replicated through the oligonucleotide portion 508 of fragment 518. As noted elsewhere herein, and as illustrated in panel D, the oligonucleotides may be configured to prompt a stop in the replication by the polymerase at a desired point, e.g., after replicating through sequences 516 and 514 of oligonucleotide 508 that is included within fragment 518. As described herein, this may be accomplished by different methods, including, for example, the incorporation of different nucleotides and/or nucleotide analogues that are not capable of being processed by the polymerase enzyme used. For example, this may include the inclusion of uracil containing nucleotides within the sequence region 512 to prevent a non-uracil tolerant polymerase to cease replication of that region. As a result a fragment 526 is created that includes the full-length oligonucleotide 508b at one end, including the barcode sequence 512, the attachment sequence 510, the R1 primer region 514, and the random N-mer sequence 516b. At the other end of the sequence can be included the complement 516' to the random N-mer of the first oligonucleotide 508, as well as a complement to all or a portion of the R1 sequence, shown as sequence 514'. The R1 sequence 514 and its complement 514' are then able to hybridize together to form a partial hairpin structure 528. As will be appreciated because the random N-mers differ among different oligonucleotides, these sequences and their complements would not be expected to participate in hairpin formation, e.g., sequence 516', which is the complement to random N-mer 516, would not be expected to be complementary to random N-mer sequence 516b. This would not be the case for other applications, e.g., targeted primers, where the N-mers would be common among oligonucleotides within a given partition.

By forming these partial hairpin structures, it allows for the removal of first level duplicates of the sample sequence from further replication, e.g., preventing iterative copying of copies. The partial hairpin structure also provides a useful structure for subsequent processing of the created fragments, e.g., fragment 526.

Figure 6:
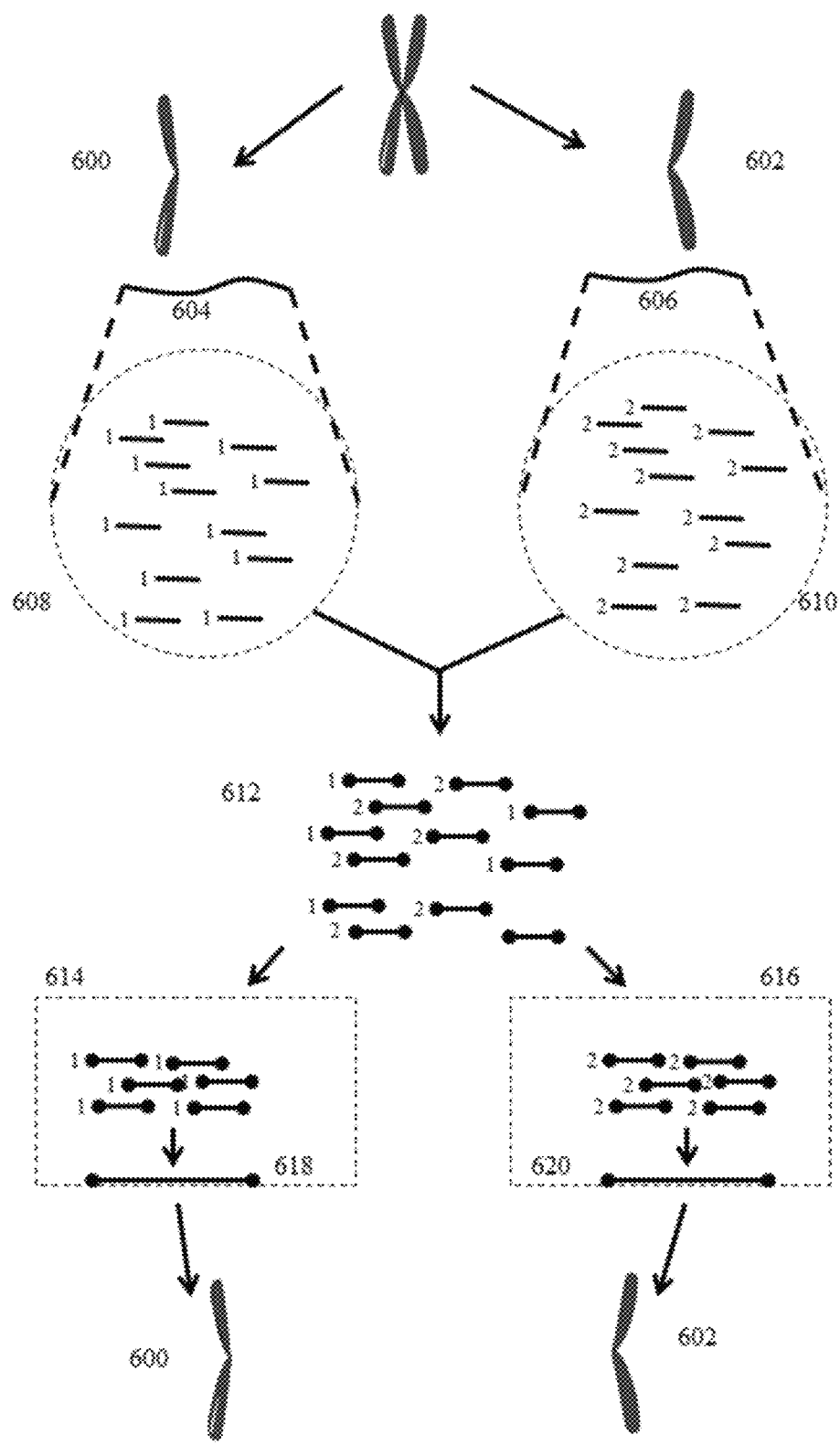
FIG. 6 provides a schematic illustration of an example use of barcoding of chromosomal nucleic acid fragments in attributing sequence data to individual chromosomes.

All of the fragments from multiple different partitions may then be pooled for sequencing on high throughput sequencers as described herein. Because each fragment is coded as to its partition of origin, the sequence of that fragment may be attributed back to its origin based upon the presence of the barcode. This is schematically illustrated in FIG. 6. As shown in one example, a nucleic acid 604 originated from a first source 600 (e.g., individual chromosome, strand of nucleic acid, etc.) and a nucleic acid 606 derived from a different chromosome 602 or strand of nucleic acid are each partitioned along with their own sets of barcode oligonucleotides as described above.

Within each partition, each nucleic acid 604 and 606 is then processed to separately provide overlapping set of second fragments of the first fragment(s), e.g., second fragment sets 608 and 610. This processing also provides the second fragments with a barcode sequence that is the same for each of the second fragments derived from a particular first fragment. As shown, the barcode sequence for second fragment set 608 is denoted by "1" while the barcode sequence for fragment set 610 is denoted by "2". A diverse library of barcodes may be used to differentially barcode large numbers of different fragment sets. However, it is not necessary for every second fragment set from a different first fragment to be barcoded with different barcode sequences. In some cases, multiple different first fragments may be processed concurrently to include the same barcode sequence. Diverse barcode libraries are described in detail elsewhere herein.

The barcoded fragments, e.g., from fragment sets 608 and 610, may then be pooled for sequencing using, for example, sequence by synthesis technologies available from Illumina or Ion Torrent division of Thermo Fisher, Inc. Once sequenced, the sequence reads 612 can be attributed to their respective fragment set, e.g., as shown in aggregated reads 614 and 616, at least in part based upon the included barcodes, and in some cases, in part based upon the sequence of the fragment itself. The attributed sequence reads for each fragment set are then assembled to provide the assembled sequence for each sample fragment, e.g., sequences 618 and 620, which in turn, may be further attributed back to their respective original chromosomes (600 and 602). Methods and systems for assembling genomic sequences are described in, for example, U.S. Provisional Patent Application No. 62/017,589, filed Jun. 26, 2014, the full disclosure of which is hereby incorporated by reference in its entirety. In some examples, genomic sequences are assembled by de novo assembly and/or reference based assembly (e.g., mapping to a reference).

III. Application of Methods and Systems to Phasing and Copy Number Assays

In one aspect of the systems and methods described herein, the ability to attribute sequence reads to longer originating molecules is used in determining phase information about the sequence. In one example, barcodes associated with sequences that reveal two or more specific gene variant sequences (e.g., alleles, genetic markers) are compared to determine whether or not that set of genetic markers reside on the same chromosome or different chromosomes in the sample. Such phasing information can be used in order to determine the relative copy number of certain target chromosomes or genes in a sample. An advantage of the described methods and symptoms is that multiple locations, loci, variants, etc. can be used to identify individual chromosomes or nucleic acid strands from which they originate in order to determine phasing and copy number information. Often, multiple locations (e.g., greater than 2, 3, 4, 5, 6, 7, 8, 9, 10, 20, 30, 40, 50, 100, 500, 1000, 5000, 10000, 50000, 100000, or 500000) along a chromosome are used in order to determine phasing, haplotype and copy number variation information described herein.

By way of example, as noted above, the methods and systems described herein, by virtue of the partitioning and attribution aspects described above, can be useful at providing effective long sequence reads from individual nucleic acid fragments, e.g., individual nucleic acid molecules, despite utilizing sequencing technology that may provide relatively shorter sequence reads. Because these long sequence reads may be attributed to single starting fragments or molecules, variant locations in the sequence can, likewise, be attributed to a single molecule, and by extrapolation, to a single chromosome. In addition, one may employ the multiple locations on any given fragment, as alignment features for adjacent fragments, to provide aligned sequences that can be inferred as originating from the same chromosome. By way of example, a first fragment may be sequenced, and by virtue of the attribution methods and systems described above, the variants present on that sequence may all be attributed to a single chromosome. A second fragment that shares a plurality of these variants that are determined to be present only on one chromosome, may then be assumed to be derived from the same chromosome, and thus aligned with the first, to create a phased alignment of the two fragments. Repeating this allows for the identification of long range phase information. Identification of variants on a single chromosome can be obtained from either known references, e.g., HapMap, or from an aggregation of the sequencing data, e.g., showing differing variants on an otherwise identical sequence stretch.

Figure 7:
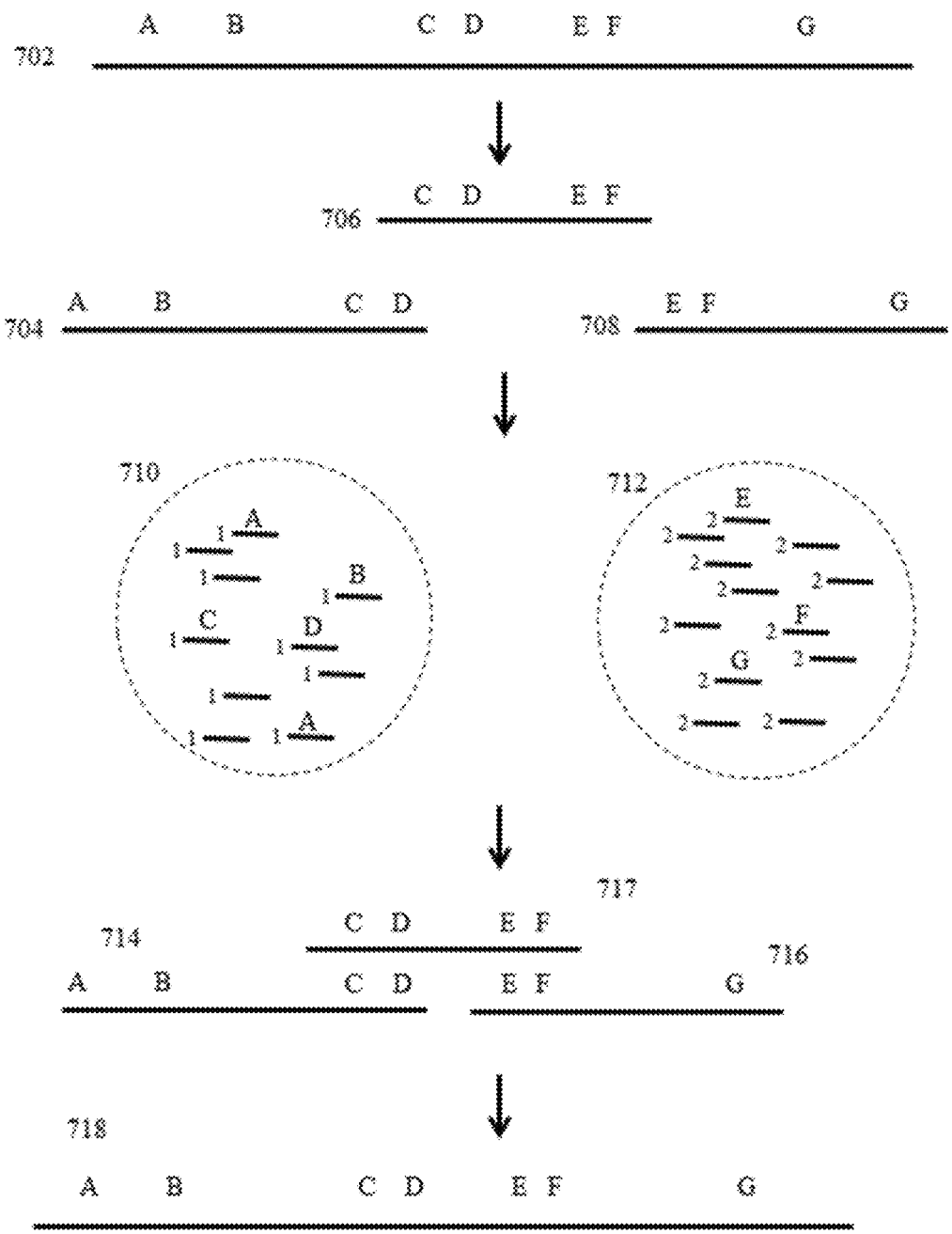
FIG. 7 provides a schematic illustration of an example of phased sequencing processes.

FIG. 7 provides a schematic illustration of an example phased sequencing process. As shown, an originating nucleic acid 702, such as, for example, a chromosome, a chromosome fragment, an exome, or other large, single nucleic acid molecule, can be fragmented into multiple large fragments 704, 706, 708. The originating nucleic acid 702 may include a number of sequence variants (A, B, C, D, E, F, and G) that are specific to the particular nucleic acid molecule, e.g., chromosome. In accordance with the processes described herein, the originating nucleic acid can be fragmented into multiple large, overlapping fragments 704, 706 and 708, that include subsets of the associated sequence variants. Each fragment can then be partitioned, further fragmented into subfragments, and barcoded, as described herein to provide multiple overlapping, barcoded subfragments of the larger fragments, where subfragments of a given larger fragment bear the same barcode sequence. For example, subfragments associated with barcode sequence "1" and barcode sequence "2" are shown in partitions 710 and 712, respectively, The barcoded subfragments can then be pooled, sequenced, and the sequenced subfragments assembled to provide long fragment sequences 714, 716, and 717. One or more of the long fragment sequences 714, 716, and 717 can include multiple variants. The long fragment sequences may then be further assembled, based upon overlapping phased variant information from sequences 714, 716, and 717 to provide a phased sequence 718, from which phased locations can be determined.

Once the phased locations are determined, one may further exploit that information in a variety of ways. For example, one can utilize knowledge of phased variants in assessing genetic risk for certain disorders, identify paternal vs. maternal characteristics, identify aneuploidies, or identify haplotyping information.

In some aspects of the systems and methods disclosed herein, copy number variation assays are performed using simultaneous detection of two or more phased genetic markers to improve the accuracy of copy number counting. Utilizing the phasing information can increase the relative strength of the signal compared to the variance under a naive method just based on counting reads over multiple loci and across haplotypes. Additionally, utilizing phasing information allows for normalization of position-specific biases, boosting the signal substantially further. Copy number variation (CNV) accuracy may depend on myriad factors including sequencing depth, length of CNV, number of copies, etc). The methods and systems provided herein may determine CNV with an accuracy of at least 70%, 80%, 85%, 90%, 91%, 92%, 93%, 94%, 95%, 99%, 99.1%, 99.2%, 99.3% 99.4%, 99.5%, 99.6%, 99.7%, 99.8%, 99.9%, 99.95%, 99.99%, 99.995%, or 99.999%. In some cases, the methods and systems provided herein determine CNV with an error rate of less than 10%, 9%, 8%, 7%, 6%, 5%, 4%, 3%, 2%, 1%, 0.1%, 0.05%, 0.01%, 0.005%, 0.001%, 0.0005%, 0.0001%, 0.00005%, 0.00001%, or 0.000005%. Similarly, the methods and systems provided herein may detect phasing/haplotype information of two or more genetic variants with an accuracy of at least 70%, 80%, 85%, 90%, 91%, 92%, 93%, 94%, 95%, 99%, 99.1%, 99.2%, 99.3% 99.4%, 99.5%, 99.6%, 99.7%, 99.8%, 99.9%, 99.95%, 99.99%, 99.995%, or 99.999%. In some cases, the methods and systems provided herein determine phasing or haplotype information with an error rate of less than 10%, 9%, 8%, 7%, 6%, 5%, 4%, 3%, 2%, 1%, 0.1%, 0.05%, 0.01%, 0.005%, 0.001%, 0.0005%, 0.0001%, 0.00005%, 0.00001%, or 0.000005%. This disclosure also provides methods of removing locus-specific biases, where the locus-specific variance are reduced by at least 2-fold, 3-fold, 4-fold, 5-fold, 10-fold, 20-fold, 30-fold, 40-fold, 50-fold, 60-fold, 70-fold, 80-fold, 90-fold, 100-fold, 200-fold, 500-fold, 1000-fold, 5000-fold, or 10000-fold. The methods and systems provided herein can be used to detect variations in copy number, such as where the change in copy number reflects a change in the number of chromosomes, or portions of chromosomes. In some cases, the methods and systems provided herein can be used to detect variations in copy number of a gene present on the same chromosome.

Figure 8:
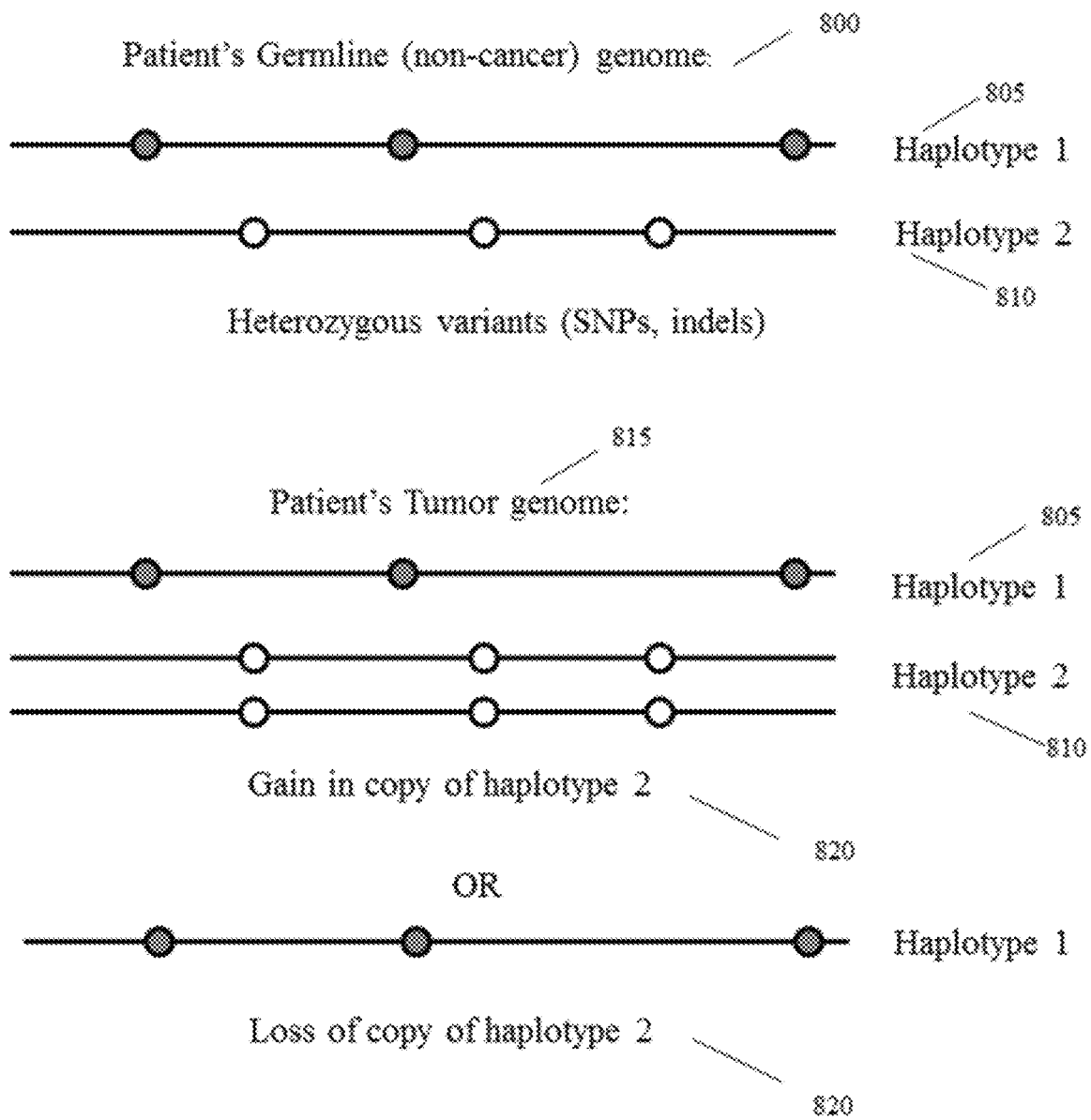
FIG. 8 provides a schematic illustration of an example subset of the genome of a healthy patient (top panel) and a cancer patient with a gain in haplotype copy number (central panel) or loss of haplotype copy number (bottom panel).
Figure 9A:
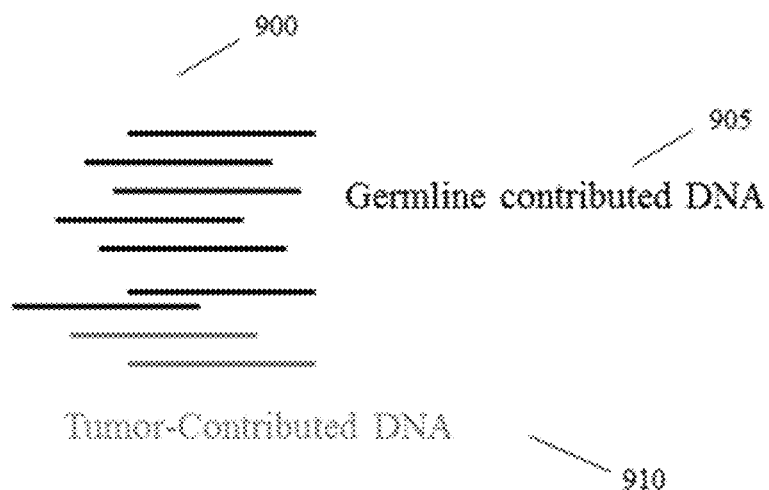
FIGS. 9A-B provides: (a) a schematic illustration showing a relative contribution of tumor DNA and (b) a representation of detecting such copy gains and losses by ordinary sequencing methods.
Figure 9B:
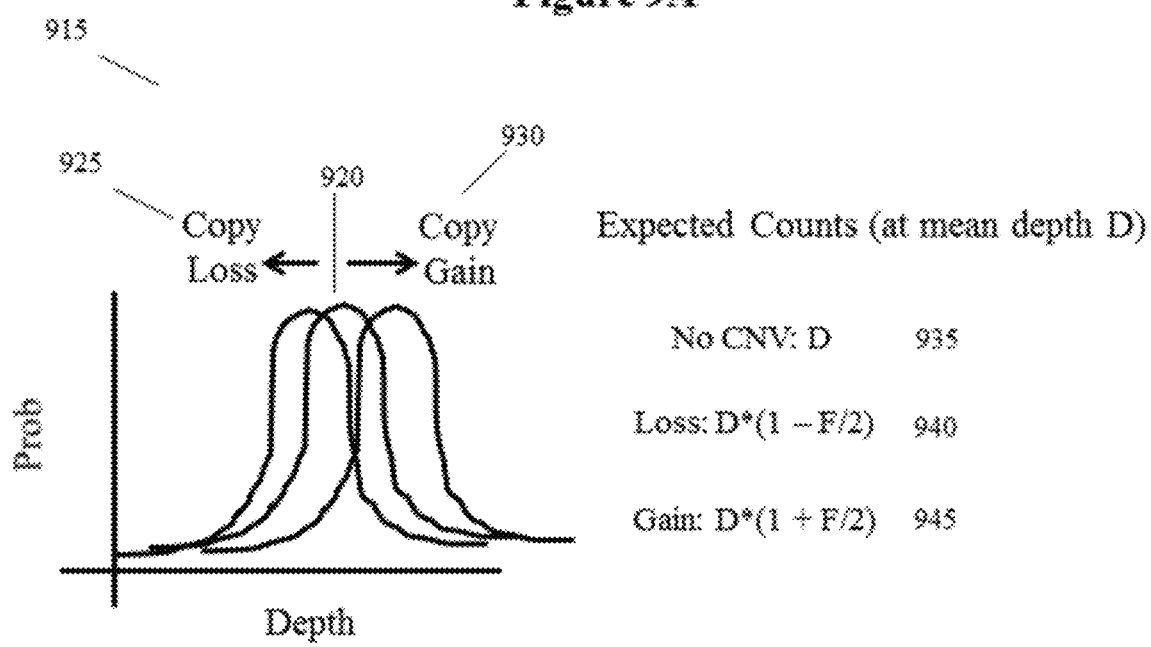
Figure 10:
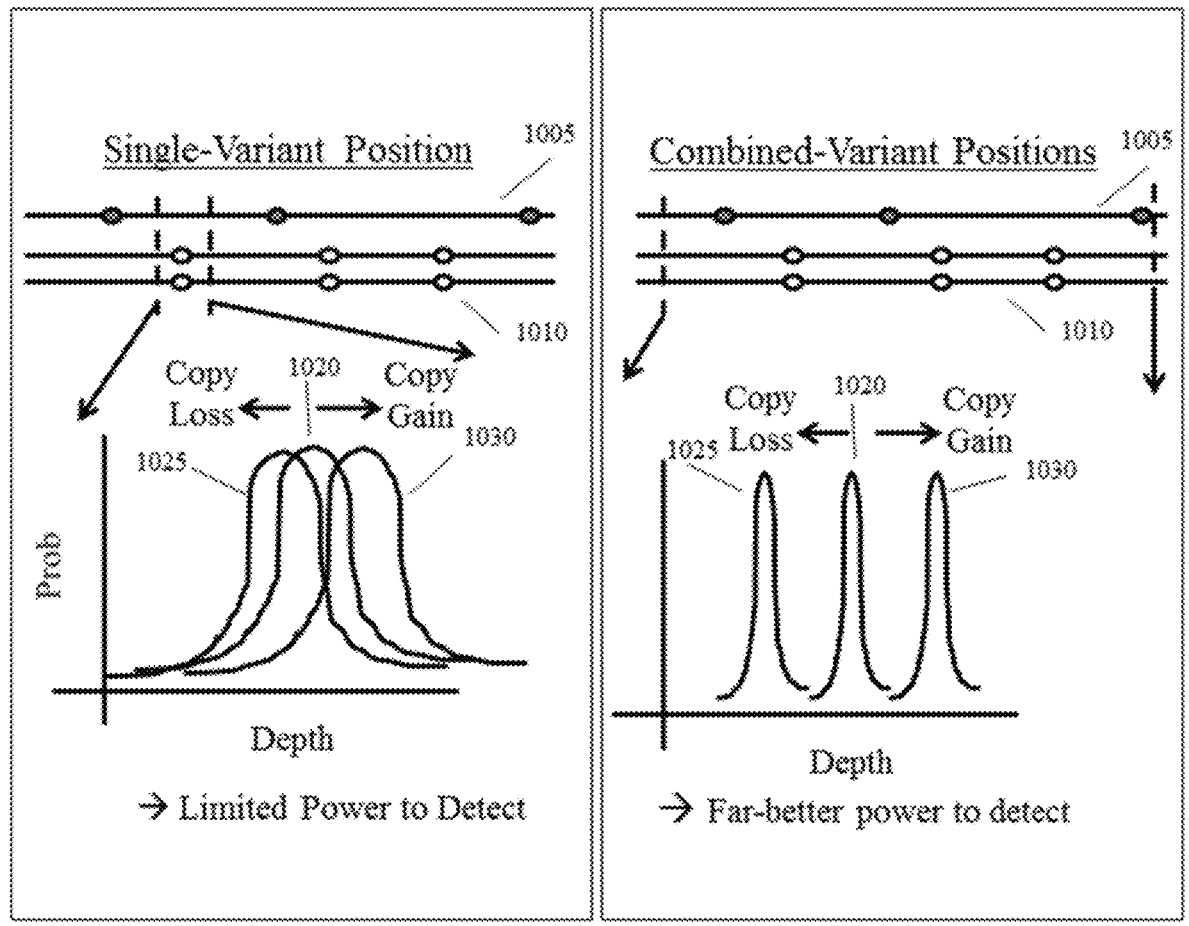
FIG. 10 provides a schematic illustration of an example of detecting copy gains and losses using a single variant position (left panel) and combined variant positions (right panel).
Figure 11:
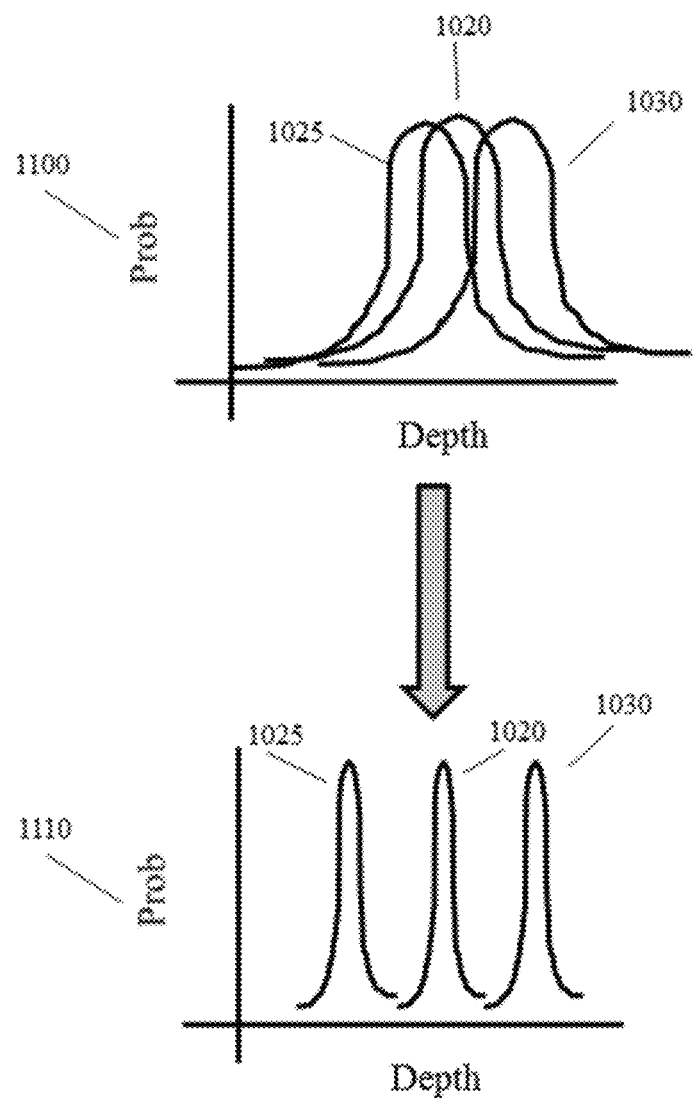
FIG. 11 provides a schematic illustration of the potential of described methods and systems to identify gains and losses in copy number.

FIG. 8 (top panel) is a schematic illustrating a subset of a healthy patient's genome. This patient has a heterozygous genotype at the indicated loci and two separate haplotypes (1 and 2) 805, 810 located on separate chromosome strands. The patient's naturally-occurring variations (such as SNPs or indels) are depicted as circles. FIG. 8 also depicts the genome of a patient with cancer 815. Certain cancers are associated with a gain in haplotype copy number. The middle panel depicts a gain in a haplotype 2, 810. Cancers may also be associated with a loss in haplotype number, as depicted in the bottom panel of FIG. 8, which shows a loss of haplotype 2 820. Common sequencing techniques cannot accurately determine this loss or gain of haplotype copies. As shown in FIG. 9a this is in part due to the fact that the tumor-contributed DNA 910 in a patient's blood is only a small fraction of the total DNA, of which a majority is the DNA contributed by normal tissue 905. This low concentration of tumor DNA results in imprecise detection of copy number with normal sequencing techniques, see FIG. 9b. The difference in the peaks of expected counts at mean depth D 935 for no copy variation 920 and the peaks for copy loss 925 (940) and copy gain 930 (945) is difficult to detect. For any given individual marker, the distribution of results of the copy number assay in replicate testing can be distributed around the correct answer in a manner approximating a Poisson distribution, where the width of the distribution is dependent on various sources of random error in the assay. Since for a give sample the change in copy number may be relatively small portion of the sample, broad probability distributions for monitoring of single genetic markers can mask the correct result. This difficulty is due to the fact that normal sequencing techniques only look at one single variant position of a haplotype at a time, as shown in FIG. 10 (left panel). Using such techniques, there can be significant overlap between peaks representing copy loss 1025, normal copy 1020, and copy gain 1030. The techniques disclosed herein allow for detection of whole (or partial) haplotypes, increasing the resolution and improving the detection of copy gain and loss, FIG. 10 (right panel). This improvement is schematically shown in FIG. 11, where normal detection 1100 results in spread out, overlapping peaks while the techniques herein 1110 allow for finer peaks and improved resolution of copy gain or loss. The use of simultaneous monitoring of two or more phased genetic markers, particularly markers that are known to be co-located on a single chromosome, and which can therefore most likely always appear in greater or lesser number in a synchronized, non-random fashion has the effect of narrowing the width of the expected results distribution and simultaneously improving the accuracy of the count.

In addition to advantages in detecting and diagnosing cancers, the methods and systems provided herein also provide more accurate and sensitive processes for detecting fetal aneuploidy.

Fetal aneuploidies are aberrations in fetal chromosome number. Aneuploidies commonly result in significant physical and neurological impairments. For example, a reduction in the number of X chromosomes is responsible for Turner's syndrome. An increase in copy number of chromosome number 21 results in Down Syndrome. Invasive testing such as amniocentesis or Chorionic Villus Sampling (CVS) can lead to risk of pregnancy loss and less invasive methods of testing the maternal blood are used here.

Figure 12:
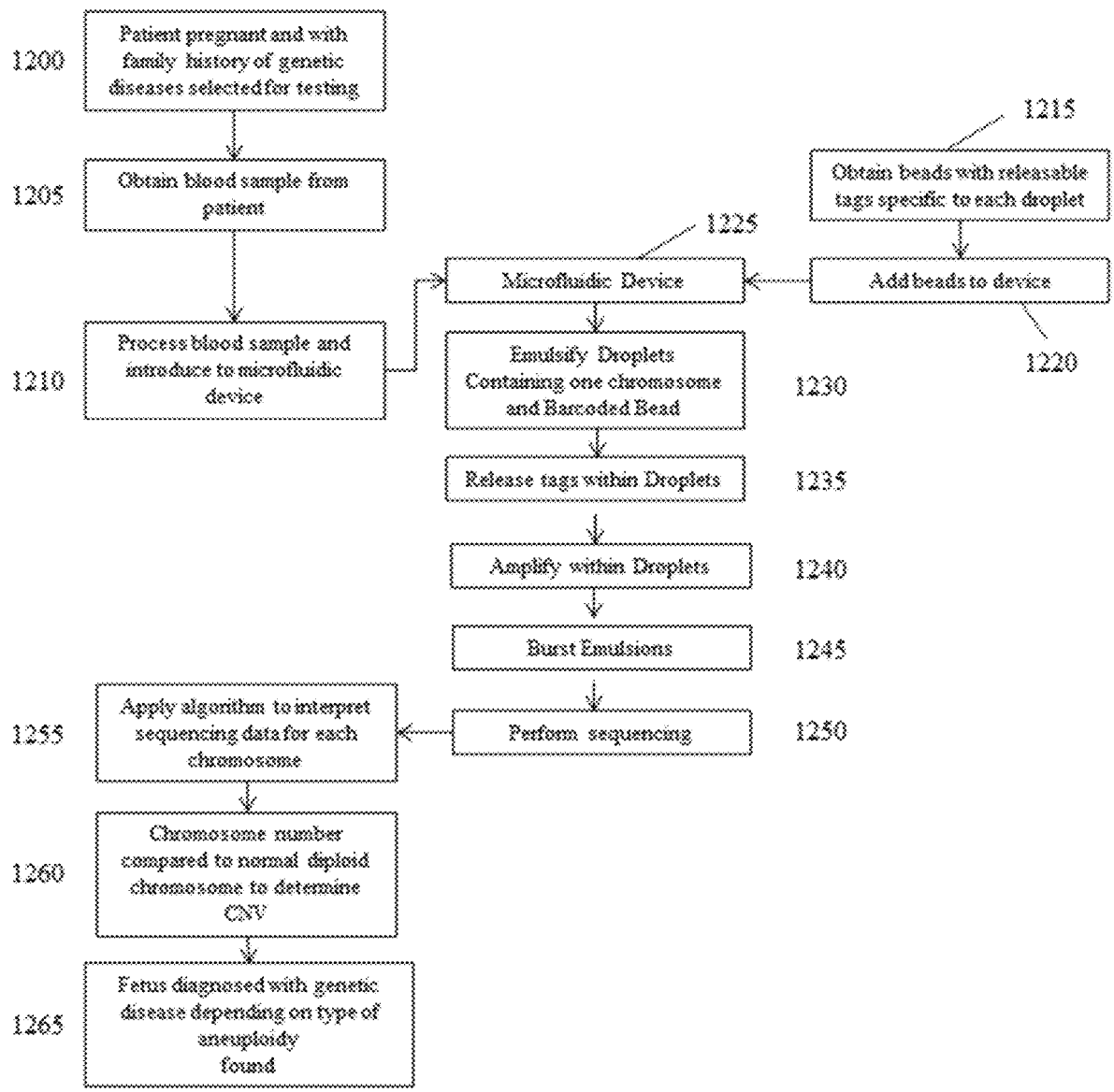
FIG. 12 illustrates an example workflow for performing an aneuploidy test based on determination of chromosome number and copy number variation using methods and compositions described herein.

Methods described herein may be useful in non-invasively detecting fetal aneuploidies. An exemplary process is shown in FIG. 12. A pregnant woman at risk of carrying a fetus with an aneuploid genome is tested, 1200. A maternal blood sample containing fetal genetic material is collected, 1205. Genetic material (e.g., cell-free nucleic acids) is then extracted from the blood sample, 1210. A set of barcoded beads may also be obtained, 1215. The beads can be linked to oligonucleotides containing one or more barcode sequences, as well as a primer, such as a random N-mer or other primer. In some cases, the barcode sequences are releasable from the barcoded beads, e.g., through cleavage of a linkage between the barcode and the bead or through degradation of the underlying bead to release the barcode, or a combination of the two. For example, in some aspects, the barcoded beads can be degraded or dissolved by an agent, such as a reducing agent to release the barcode sequences. In this example, a sample, 1210, barcoded beads, 1220, and, in some cases, other reagents, e.g., a reducing agent, are combined and subjected to partitioning. By way of example, such partitioning may involve introducing the components to a droplet generation system, such as a microfluidic device, 1225. With the aid of the microfluidic device 1225, a water-in-oil emulsion 1230 may be formed, where the emulsion contains aqueous droplets that contain sample nucleic acid, 1210, barcoded beads, 1215, and, in some cases, a reducing agent. The reducing agent may dissolve or degrade the barcoded beads, thereby releasing the oligonucleotides with the barcodes and random N-mers from the beads within the droplets, 1235. The random N-mers may then prime different regions of the sample nucleic acid, resulting in amplified copies of the sample after amplification, where each copy is tagged with a barcode sequence, 1240. In some cases, each droplet contains a set of oligonucleotides that contain identical barcode sequences and different random N-mer sequences. In other embodiments, individual droplets comprise unique bar-code sequences; or, in some cases, a certain proportion of the total population of droplets has unique sequences. Subsequently, the emulsion is broken, 1245 and additional sequences (e.g., sequences that aid in particular sequencing methods, additional barcodes, etc.) may be added, via, for example, amplification methods (e.g., PCR). Sequencing may then be performed via any suitable type of sequencing platform (e.g., Illumina, Ion Torrent, Pacific Biosciences SMRT, Roche 454 sequencing SOLiD sequencing, etc.), 1250, and an algorithm applied to interpret the sequencing data, 1255. Sequencing algorithms are generally capable, for example, of performing analysis of barcodes to align sequencing reads and/or identify the sample from which a particular sequence read belongs. The aligned sequences may be further attributed to their respective genetic origins (e.g., chromosomes) based upon, the unique barcodes attached. The number of chromosome copies is then compared to that of a normal diploid chromosome, 1260. The patient is informed of any copy number aberrations for different chromosomes and the associated risks/disease, 1265.

Phasing, e.g. determining whether genetic variants are linked or reside on different chromosomes can provide useful information for a variety of applications. By way of example, phasing is useful for determining if certain translocations of a genome associated with diseases are present. Detection of such translocations can also allow for differential diagnosis and modified treatment. Determination of which alleles in a genome are linked can be useful for considering how genes are inherited.

It can often be useful to know the pattern of alleles, the haplotype, for each individual chromosome of a chromosome pair. For example, two copies of an inactivating mutation present on one chromosome may be of limited consequence, but could have significant effect if distributed between the two chromosomes, e.g., where neither chromosome supplies active gene product. These effects can be expressed e.g., with increased risk of disease or lack of response to certain medications.

IV. Application of Methods and Systems to Identification/Characterization of Structural Variations In other applications, the method and systems described herein are highly useful in obtaining the long range molecular sequence information for identification and characterization of a wide range of different genetic structural variations. As noted above, these variations include a wide variety of different variant events, including insertions, deletions, duplications, retrotransposons, translocations, inversions short and long tandem repeats, and the like. These structural variations are of significant scientific interest, as they are believed to be associated with a range of diverse genetic diseases.

Despite the interest in these variations, there are few effective and efficient methods of identifying and characterizing these structural variations. In part, this is because these variations are not characterized by the presence of abnormal sequence segments, but instead, involve and abnormal sequence context of what would be considered normal sequence segments, or simply missing sequence information. Because of their relatively short read lengths, most sequencing technologies are unable to provide significant context, and especially, long range sequence context, e.g., beyond their read lengths, for the sequence reads they produce, and thus lose the identification of these variations in the assembly process. The difficulties in identifying these variations is further complicated by the ensemble approach of these technologies in which many molecules, e.g., multiple chromosomes, are combined to yield a consensus sequence that may include genomic material that both includes and does not include the variation.

In the context of the presently described methods and systems, however, one can utilize short read sequencing technologies to derive long range sequence information that is attributable to individual originating nucleic acid molecules, and thus retain the long range sequence context of variant regions contained in whole or in part in those individual molecules.

As described above, the methods and systems described herein are capable of providing long range sequence information that is attributable to individual originating nucleic acid molecules, and further, in possessing this long range sequence information, inferring even longer range sequence context, through the comparing and overlapping of these longer sequence information. Such long range sequence information and/or inferred sequence context allows the identification and characterization numerous structural variations not easily identified using available techniques.

Figure 2:
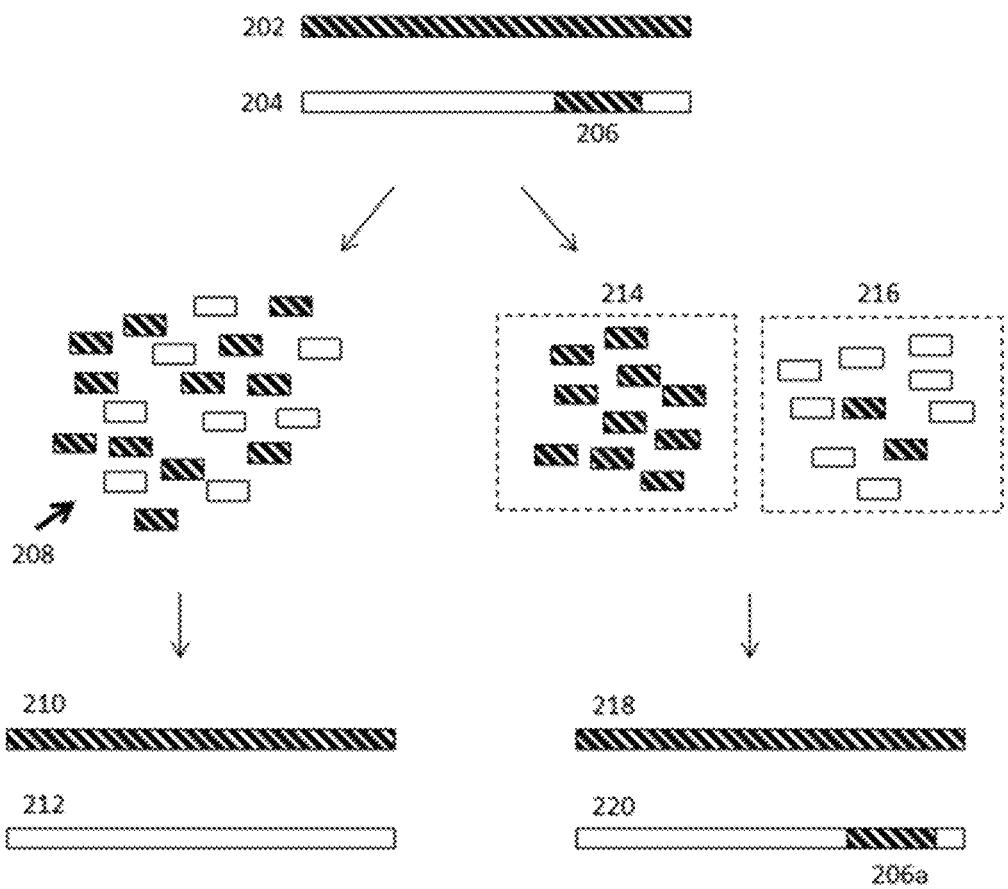
FIG. 2 provides a schematic illustration of the identification and analysis of structural variations using conventional processes versus example processes and systems described herein.
Figures 13A, 13B:
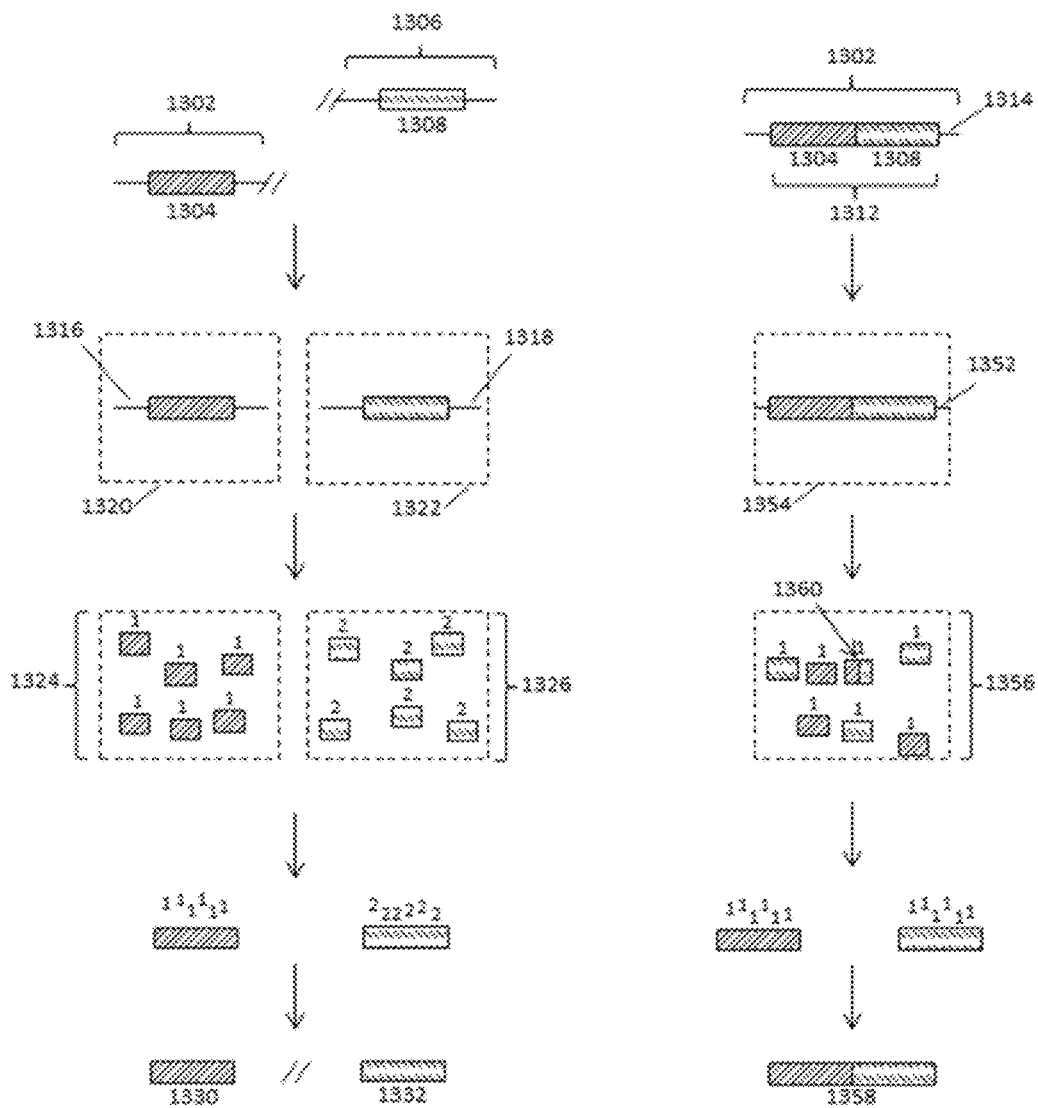
FIGS. 13A-B illustrate an example overview of a process for identifying structural variations such as translocations and gene fusions in genetic samples.

While illustrated in simplified fashion in FIG. 2, FIGS. 13A and 13B provide a more detailed example process for identifying certain types of structural variations using the methods and systems described herein. As shown, the genome of an organism, or tissue from an organism, might ordinarily include the first genotype illustrated in FIG. 13A, where a first gene region 1302 including first gene 1304 is separated from a second gene region 1306 including second gene 1208. This separation may reflect a range of distances between the genes, including, e.g., different regions in the same exon, different exons on the same chromosome, different chromosomes, etc. As shown in FIG. 13B however, a genotype is shown that reflects a translocation event having occurred in which gene 1308 is inserted into gene region 1304 such that it creates a gene fusion between genes 1304 and 1308 as gene fusion 1312 in variant sequence 1314.

Current methods for detecting large genomic structural variants (such as large inversions or translocations) rely on read pairs that span the breakpoints of the variants (for example the genomic loci where the translocated parts fused together). To ensure that such read pairs are observed during a sequencing experiment, very deep sequencing can be required. In targeted sequencing (such as exome sequencing), detecting structural variants with current sequencing technologies is almost impossible, unless the breakpoint is within the targeted regions (e.g. in an exon), which is very unlikely.

Information provided by the barcode methods and systems described herein, however, can greatly improve the ability to detect structural variants. Intuitively, the loci to the left and to the right of a breakpoint, can tend to be on a common fragment of genomic DNA and therefore be maintained within a single partition, and thus barcoded with a common or shared barcode sequence. Due to the stochastic nature of shearing, this sharing of barcodes decreases as the sequences are more distant from the breakpoint. Using statistical methods one can determine whether the barcode overlap between two genomic loci is significantly larger than what would be expected by chance. Such an overlap suggests the presence of a breakpoint. Importantly, the barcode information complements information provided by traditional sequencing (such as information from reads spanning the breakpoint) if such information is available.

In the context of the methods described herein, the genomic material from the organism, including the relevant gene regions is fragmented such that it includes relatively long fragments, as described above. This is illustrated with respect to the non-translocated genotype in FIG. 13A. As shown two long individual first molecule fragments 1316 and 1318 are created that include gene regions 1302 and 1306 respectively. These fragments are separately partitioned into partitions 1320 and 1322, respectively, and each of the first fragments is fragmented into a number of second fragments 1324 and 1326, respectively within the partition, which fragmenting process attaches a unique identifier tag or barcode sequence to the second fragments that is common to all of the second fragments within a given partition. The tag or barcode is indicated by "1" or "2", for each of partitions 1320 and 1322, respectively. As a result, completely separate genes 1304 and 1308 can result in differently partitioned, and differently barcoded groups of second fragments.

Once barcoded, the second fragments may then be pooled and subjected to nucleic acid sequencing processes, which can provide both the sequence of the second fragment as well as the barcode sequence for that fragment. Based upon the presence of a particular barcode, e.g., 1 or 2, a the second fragment sequences may then be attributed to a certain originating sequence, e.g., gene 1304 or 1308, as shown by the attribution of barcodes to each sequence. In some cases, mapping of barcoded second fragment sequences as to separate originating first fragment sequences may be sufficiently definitive to determine that no translocation has occurred. However, in some cases, one may assemble the second fragment sequences to provide an assembled sequence for all or a portion of the originating first fragment sequence, e.g., as shown by assembled sequences 1330 and 1332.

In contrast to the non-translocated genotype example shown in FIG. 13A, FIG. 13B shows a schematic illustration of the same process applied to a translocation containing genotype. As shown, a first long nucleic acid fragment 1352 is generated from the variant sequence 1314, and includes at least a portion of the translocation variant, e.g., gene fusion 1312. The first fragment 1352 is then partitioned into discrete partition 1354. Within partition 1354, first fragment 1352 is further fragmented into second fragments 1356 that again, include unique barcodes that are the same for all second fragments 1356 within the partition 1354 (shown as barcode "1"). As above, pooling the second fragments and sequencing provides the underlying sequences of the second fragments as well as their associated barcodes. These barcoded sequences can then be attributed to their respective gene sequences. As shown, however, both genes can reflect attributed second fragment sequences that include the same barcode sequences, indicating that they originated from the same partition, and potentially the same originating molecule, indicating a gene fusion. This may be further validated by providing a number of overlapping first fragments that also include at least portions of the gene fusion, but processed in different partitions with different barcodes.

In some cases, the presence of multiple different barcode sequences (and their underlying fragment sequences) that attribute to each of the originally separated genes can be indicative of the presence of a gene fusion or other translocation event. In some cases, attribution of at least 2 barcodes, at least 3 different barcodes, at least 4 different barcodes, at least 5 different barcodes, at least 10 different barcodes, at least 20 different barcodes or more, to two genetic regions that would have been expected to have been separated based upon a reference sequence, may provide indication of a translocation event that has placed those regions proximal to, adjacent to or otherwise integrated with each other. In some cases, the size of the fragments that are partitioned can indicate the sensitivity with which one can identify variant linkage. In particular, where the fragments in a given droplet are 10 kb in length, it would be expected that linkages that are within that 10 kb size range would be detectable.

Likewise, where both the variant and the wild type structure fall within the same 10 kb fragment, it would be expected that identification of that variant would be more difficult, as both would show linkage through common or shared barcodes. As such, fragment size selection may be used to adjust the relative proximity of detected linked sequences, whether as wild type or variants. In general, however, structural variants that result in proximal sequences that are normally separated by more than 100 bases, more than 500 bases, more than 1 kb, 10 kb, more than 20 kb, more than 30 kb, more than 40 kb, more than 50 kb, more than 60 kb, more than 70 kb, more than 80 kb, more than 90 kb, more than 100 kb, more than 200 kb or even greater, may be readily identified herein by identifying the linkage between those unlinked sequence segments in variant genomes, which linkage is indicated by shared or common barcodes, and/or, as noted, by sequence data that spans a breakpoint. Such linkage is generally identifiable when those linked sequences are separated within the genomic sequence by less than 50 kb, less than 40 kb, less than 30 kb, less than 20 kb, less than 10 kb, less than 5 kb, less than 4 kb, less than 3 kb, less than 2 kb, less than 1 kb, less than 500 bases, less than 200 bases or even less.

In some cases, a structural variation resulting in two sequences being positioned proximal to each other or linked, where they would normally be separated by, e.g., more than 10 kb, more than 20 kb, more than 30 kb, more than 40 kb, or more than 50 kb or more, may be identified by the percentage of the total number of mappable barcoded sequences that include barcodes that are common to the two sequence portions.

As will be appreciated, in some cases, the processes described herein can ensure that sequences that are within a certain sequence distance will be included, whether as wild type or variant sequences, within a single partition, e.g., as a single nucleic acid fragment. For example, where common or overlapping barcode sequences are greater than 1% of the total number of barcodes mapped to the two sequences, it may be used to identify linkage as between two sequence segments, and particularly, as between two sequence segments that would not normally be linked, e.g., a structural variation. In some cases, the shared or common barcodes can be more than 2%, more than 3%, more than 4%, more than 5%, more than 6%, more than 7%, more than 8%, and in some cases more than 9% or even more than 10% of the total mappable barcodes to two normally separated sequences, in order to identify a structural linkage that constitutes a structural variation within the genome. In some cases, the shared or common barcodes can be detected at a proportion or number that is statistically significantly greater than a control genome that is known not to have the structural variation. Additionally, where second sequence fragments span the point where the variant sequence meets the "normal" sequence, or "breakpoint", e.g., as in second fragment 1358 one can use this information as additional evidence of the gene fusion.

Again, as above, one can further elucidate the structure of the gene fusion 1312, by assembling the second fragment sequences to yield the assembled sequence of the gene fusion 1312, shown as assembled sequence 1360.

Further, while the presence of the barcode sequences allows the assembly of the short sequences into sequences for the longer originating fragments, these longer fragments also permit the inference of longer range sequence information from overlapping long fragments assembled from different, overlapping originating long fragments. This resulting assembly allows for longer range sequence level identification and characterization of gene fusion 1312.

In some cases, the methods described above are useful in identifying the presence of retrotransposons. Retrotransposons can be created by transcription followed by reverse transcription of spliced messenger RNA (mRNA) and insertion into a new location in the genome. Hence, these structural variants lack introns and are often interchromosomal but otherwise have diverse features. When retrotransposons introduce functional copies of genes they are referred to as retrogenes, which have been reported in human and Drosophila genomes. In other cases, retrocopies may contain the entire transcript, specific transcript isoforms or an incomplete transcript. In addition, alternative transcription start sites and promoter sequences sometimes reside within a transcript so retrotransposons sometimes introduce promotor sequences within the reinserted region of the genome that could drive expression of downstream sequences.

Unlike tandem duplications, retrotransposons insert far away from the parental gene within exons or introns. When inserted near genes retrotransposons can exploit local regulatory sequences for expression. Insertions near genes can also inactivate the receiving gene or create new chimera transcripts. Retrotransposon mediated chimeric gene transcripts have been reported in RNA-Seq data from human samples.

Despite the significance of retrotransposons their detection can be limited to directed approaches relying on paired read support from mate pair libraries, exon-exon junction discovery in whole genome sequencing (WGS) or RNA-Seq recognition of retrotransposon chimeras. All of these methods can have false positives that complicate analysis.

Retrotransposons can be identified from whole genome libraries using the systems and methods described herein, and their insertion site can be mapped using the barcode mapping discussed above. For example, the Ceph NA12878 genome has a SKA3-DDX10 chimeric retrotransposon. The SKA3 intron-less transcript is inserted in between exons 10 and 11 of DDX10. Furthermore the CBX3-C15ORF17 retrotransposon can also be detected in NA12878 using the methods described herein. Isoform 2 of CBX3 is inserted in between exons 2 and 3 of C15ORF17. This chimeric transcript has been observed in 20% of European RNA-Seq samples from the HapMap project (D. R. Schrider et al. PLoS Genetics 2013).

Retrotransposons can also be detected in whole exome libraries prepared using the methods and systems described herein. While retrotransposons are easily enriched with exome targeting it can be difficult or not possible to differentiate between a translocation event and a retrotransposon since introns are removed during capture. However, using the systems and methods described herein, one may identify retrotransposons in whole exome sequencing (WES) libraries by introducing intronic baits for suspected retrotransposons (see also U.S. Provisional Patent Application No. 62/072,164, filed Oct. 29, 2014, incorporated herein by reference in its entirety for all purposes). Lack of intron signal can be indicative of retrotransposon structural variants whereas intron signal can be indicative of a translocation.

As will be appreciated, the ability to use longer range sequence context in identifying and characterizing of the above-described variations is equally applicable to identifying the range of other structural variations, including insertions, deletion, retrotransposons, inversions, etc., by mapping barcodes to regions within the variation, and/or spanning the variation.

V. Diseases & Disorders Arising from Copy Number Variation

The present methods and systems provide a highly accurate and sensitive approach to diagnosing and/or detecting a wide range of diseases and disorders. Diseases associated with copy number variations can include, for example, DiGeorge/velocardiofacial syndrome (22q11.2 deletion), Prader-Willi syndrome (15q11-q13 deletion), Williams-Beuren syndrome (7q11.23 deletion), Miller-Dieker syndrome (MDLS) (17p13.3 microdeletion), Smith-Magenis syndrome (SMS) (17p11.2 microdeletion), Neurofibromatosis Type 1 (NF1) (17q11.2 microdeletion), Phelan-McErmid Syndrome (22q13 deletion), Rett syndrome (loss-of-function mutations in MECp2 on chromosome Xq28), Merzbacher disease (CNV of PLP1), spinal muscular atrophy (SMA) (homozygous absence of telomerec SMN1 on chromosome 5q13), Potocki-Lupski Syndrome (PTLS, duplication of chromosome 17p.11.2). Additional copies of the PMP22 gene can be associated with Charcot-Marie-Tooth neuropathy type IA (CMT1A) and hereditary neuropathy with liability to pressure palsies (HNPP). The disease can be a disease described in Lupski J. (2007) Nature Genetics 39: S43-S47.

The methods and systems provided herein can also accurately detect or diagnose a wide range of fetal aneuploidies. Often, the methods provided herein comprise analyzing a sample (e.g., blood sample) taken from a pregnant woman in order to evaluate the fetal nucleic acids within the sample. Fetal aneuploidies, can include, e.g., trisomy 13 (Patau syndrome), trisomy 18 (Edwards syndrome), trisomy 21

(Down Syndrome), Klinefelter Syndrome (XXY), monosomy of one or more chromosomes (X chromosome monosomy, Turner's syndrome), trisomy X, trisomy of one or more chromosomes, tetrasomy or pentasomy of one or more chromosomes (e.g., XXXX, XXYY, XXXY, XYYY, XXXXX, XXXXY, XXXYY, XYYYY and XXYYY), triploidy (three of every chromosome, e.g. 69 chromosomes in humans), tetraploidy (four of every chromosome, e.g. 92 chromosomes in humans), and multiploidy. In some embodiments, an aneuploidy can be a segmental aneuploidy. Segmental aneuploidies can include, e.g., 1p36 duplication, dup(17)(p11.2p11.2) syndrome, Down syndrome, Pelizaeus-Merzbacher disease, dup(22)(q11.2q11.2) syndrome, and cat-eye syndrome. In some cases, an abnormal genotype, e.g., fetal genotype, is due to one or more deletions of sex or autosomal chromosomes, which can result in a condition such as Cri-du-chat syndrome, Wolf-Hirschhorn, Williams-Beuren syndrome, Charcot-Marie-Tooth disease, Hereditary neuropathy with liability to pressure palsies, Smith-Magenis syndrome, Neurofibromatosis, Alagille syndrome, Velocardiofacial syndrome, DiGeorge syndrome, Steroid sulfatase deficiency, Kallmann syndrome, Microphthalmia with linear skin defects, Adrenal hypoplasia, Glycerol kinase deficiency, Pelizaeus-Merzbacher disease, Testis-determining factor on Y, Azospermia (factor a), Azospermia (factor b), Azospermia (factor c), or 1p36 deletion. In some embodiments, a decrease in chromosomal number results in an XO syndrome Excessive genomic DNA copy number variation is also associated with Li-Fraumeni cancer predisposition syndrome (Shlien et al. (2008) PNAS 105:11264-9). CNV is associated with malformation syndromes, including CHARGE (coloboma, heart anomaly, choanal atresia, retardation, genital, and ear anomalies), Peters-Plus, Pitt-Hopkins, and thrombocytopenia-absent radius syndrome (see e.g., Ropers HH (2007) Am J of Hum Genetics 81: 199-207). The relationship between copy number variations and cancer is described, e.g., in Shlien A. and Malkin D. (2009) Genome Med. 1(6): 62. Copy number variations are associated with, e.g., autism, schizophrenia, and idiopathic learning disability. See e.g., Sebat J., et al. (2007) Science 316: 445-9; Pinto J. et al.

As described herein, the methods and systems provided herein are also useful to detect CNVs associated with different types of cancer. For example, the methods and systems can be used to detect EGFR copy number, which can be increased in non-small cell lung cancer.

The methods and systems provided herein can also be used to determine a subject's level of susceptibility to a particular disease or disorder, including susceptibility to infection from a pathogen (e.g., viral, bacterial, microbial, fungal, etc.). For example, the methods can be used to determine a subject's susceptibility to HIV infection by analyzing the copy number of CCL3L1, given that a relatively high level of CCL3L1 is associated with lower susceptibility to HIV infection (Gonzalez E. et al. (2005) Science 307: 1434-1440). In another example, the methods can be used to determine a subject's susceptibility to system lupus erythematosus. In such cases, for example, the methods can be used to detect copy number of FCGR3B (CD16 cell surface immunoglobulin receptor) since a low copy number of this molecule is associated with an increased susceptibility to systemic lupus erythematosus (Aitman T. J. et al. (2006) Nature 439: 851-855). The methods and systems provided herein can also be used to detect CNVs associated with other diseases or disorders, such as CNVs associated with autism, schizophrenia, or idiopathic learning disability (Kinght et al., (1999) The Lancet 354 (9191): 1676-81.). Similarly, the methods and systems can be used to detect autosomal-dominant microtia, which is linked to five tandem copies of a copy-number-variable region at chromosome 4p16 (Balikova I. (2008) Am J. Hum Genet. 82: 181-187).

VI. Detection, Diagnosis and Treatment of Diseases and Disorders

The methods and systems provided herein can also assist with the detection, diagnosis, and treatment of a disease or disorder. In some cases, a method comprises detecting a disease or disorder using a system or method described herein and further providing a treatment to a subject based on the detection of the disease. For example, if a cancer is detected, the subject may be treated by a surgical intervention, by administering a drug designed to treat such cancer, by providing a hormonal therapy, and/or by administering radiation or more generalized chemotherapy.

Often, the methods and systems also permit a differential diagnosis and may further comprise treating a patient with a targeted therapy. In general, differential diagnosis of a disease or disorder (or absence thereof) can be achieved by determining and characterizing a sequence of a sample nucleic acid obtained from a subject suspected of having the disease or disorder and further characterizing the sample nucleic acid as indicative of a disorder or disease state (or absence thereof) by comparing it to a sequence and/or sequence characterization of a reference nucleic acid indicative of the presence (or absence) of the disorder or disease state.

The reference nucleic acid sequence may be derived from a genome that is indicative of an absence of a disease or disorder state (e.g., germline nucleic acid) or may be derived from a genome that is indicative of a disease or disorder state (e.g., cancer nucleic acid, nucleic acid indicative of an aneuploidy, etc.). Moreover, the reference nucleic acid sequence (e.g., having lengths of longer than 1 kb, longer than 5 kb, longer than 10 kb, longer than 15 kb, longer than 20 kb, longer than 30 kb, longer than 40 kb, longer than 50 kb, longer than 60 kb, longer than 70 kb, longer than 80 kb, longer than 90 kb or even longer than 100 kb) may be characterized in one or more respects, with non-limiting examples that include determining the presence (or absence) of a particular sequence, determining the presence (or absence) of a particular haplotype, determining the presence (or absence) of one or more genetic variations (e.g., structural variations (e.g., a copy number variation, an insertion, a deletion, a translocation, an inversion, a retrotransposon, a rearrangement, a repeat expansion, a duplication, etc.), single nucleotide polymorphisms (SNPs), etc.) and combinations thereof. Moreover, any suitable type and number of sequence characteristics of the reference sequence can be used to characterize the sequence of the sample nucleic acid. For example, one or more genetic variations (or lack thereof) or structural variations (or lack thereof) of a reference nucleic acid sequence may be used as a sequence signature to identify the reference nucleic acid as indicative of the presence (or absence) of a disorder or disease state. Based on the characterization of the reference nucleic acid sequence utilized, the sample nucleic acid sequence can be characterized in a similar manner and further characterized/identified as derived (or not derived) from a nucleic acid indicative of the disorder or disease based upon whether or not it displays a similar character to the reference nucleic acid sequence. In some cases, characterizations of sample nucleic acid sequence and/or the reference nucleic acid sequence and their comparisons may be completed with the aid of a programmed computer processor. In some cases, such a programmed computer processor can be included in a computer control system, such as in an example computer control system described elsewhere herein.

The sample nucleic acid may be obtained from any suitable source, including sample sources and biological sample sources described elsewhere herein. In some cases, the sample nucleic acid may comprise cell-free nucleic acid. In some cases, the sample nucleic acid may comprise tumor nucleic acid (e.g., tumor DNA). In some cases, the sample nucleic acid may comprise circulating tumor nucleic acid (e.g., circulating tumor DNA (ctDNA)). Circulating tumor nucleic acid may be derived from a circulating tumor cell (CTC) and/or may be obtained, for example, from a subject's blood, plasma, other bodily fluid or tissue.

Figure 20:
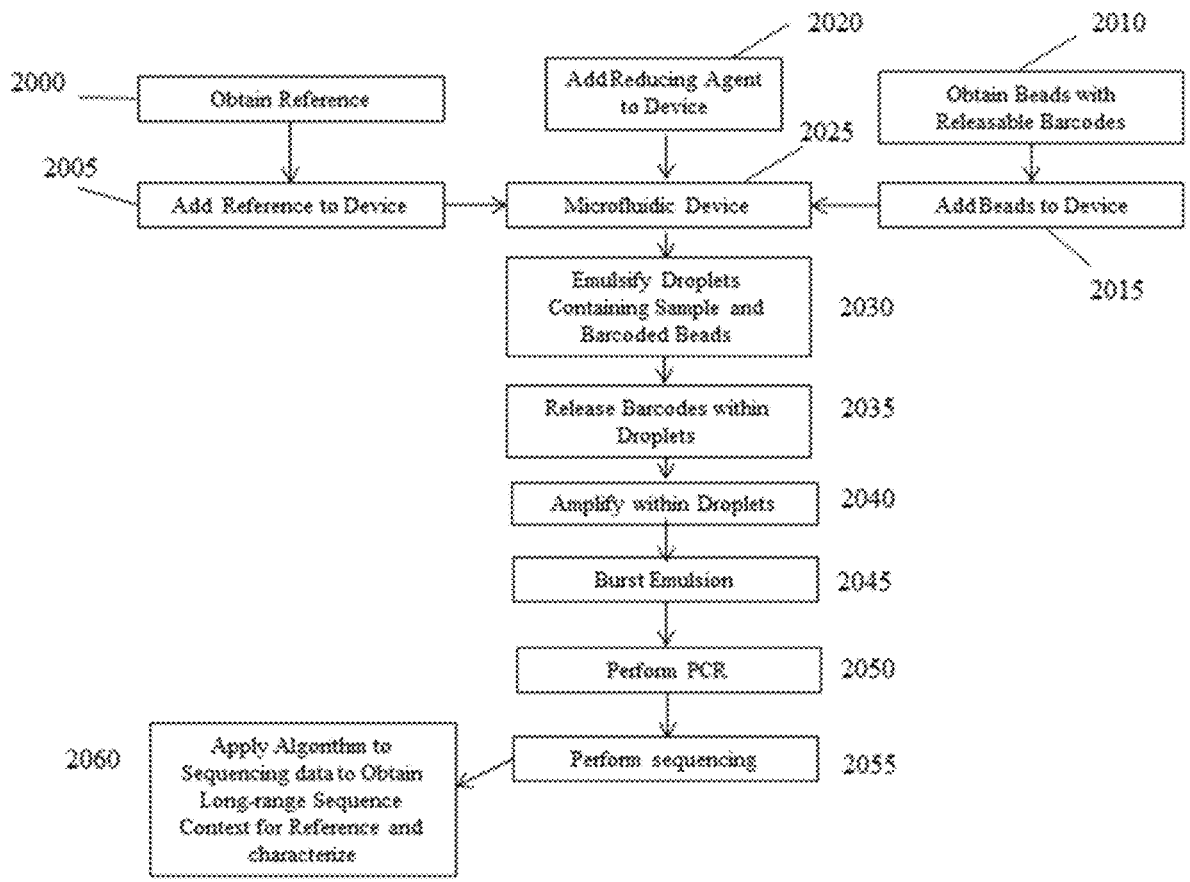
FIG. 20 schematically depicts an example workflow of analyzing a reference nucleic acid sequence as described herein.
Figure 21:
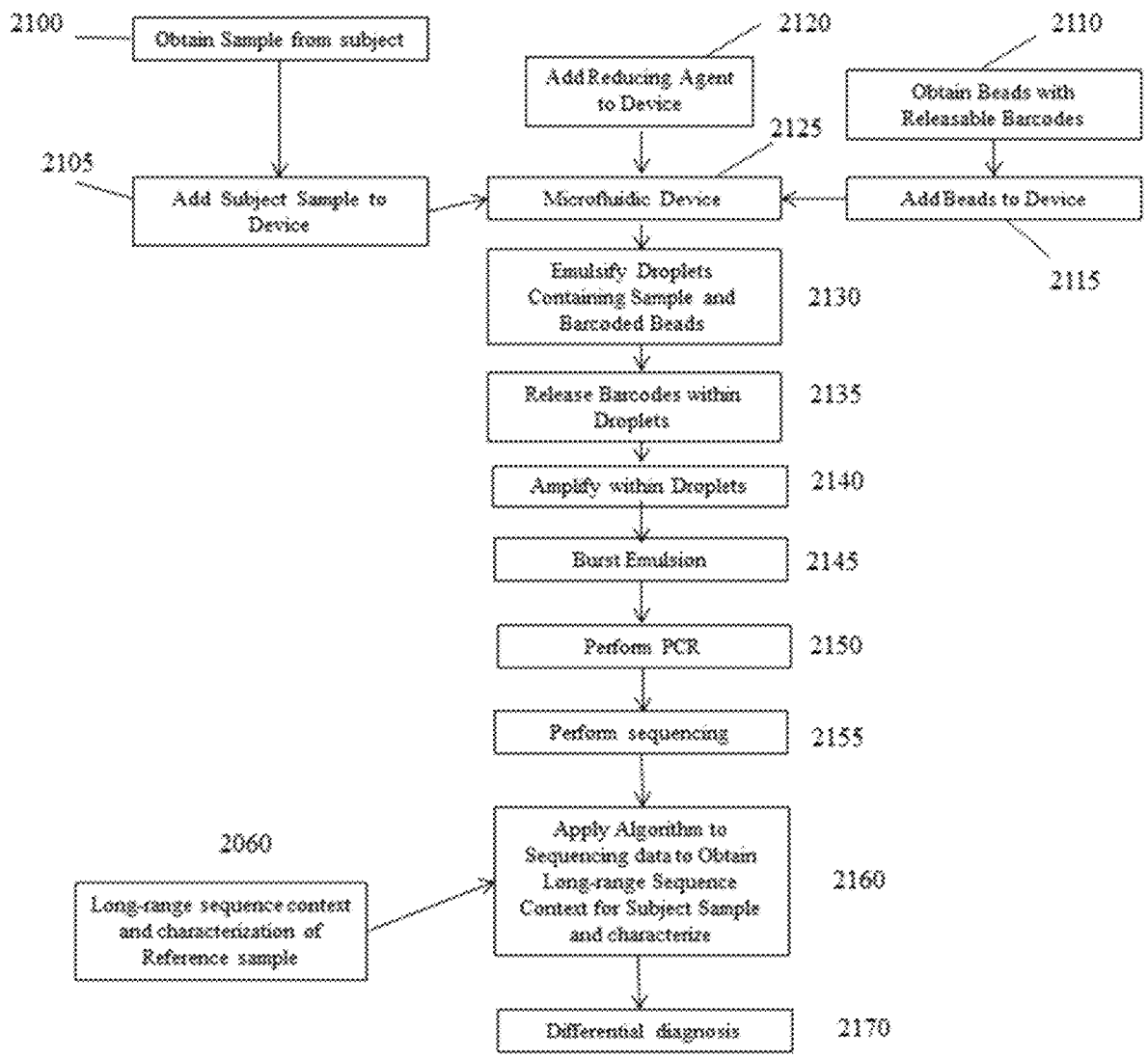
FIG. 21 schematically depicts an example workflow of analyzing a sample nucleic acid sequence as described herein.

FIGS. 20-21 illustrate an example method for characterizing a sample nucleic acid in the context of disease detection and diagnosis. FIG. 20 demonstrates an example method by which long range sequence context can be determined for a reference nucleic acid (e.g., germline nucleic acid (e.g., germline genomic DNA), nucleic acid associated with a particular disorder or disease state) from shorter barcoded fragments, such as, for example in a manner analogous to that shown in FIG. 6. With respect to FIG. 20, a reference nucleic acid may be obtained 2000, and a set of barcoded beads may also be obtained, 2010. The beads can be linked to oligonucleotides containing one or more barcode sequences, as well as a primer, such as a random N-mer or other primer. In some cases, the barcode sequences are releasable from the barcoded beads, e.g., through cleavage of a linkage between the barcode and the bead or through degradation of the underlying bead to release the barcode, or a combination of the two. For example, in some aspects, the barcoded beads can be degraded or dissolved by an agent, such as a reducing agent to release the barcode sequences. In this example, reference nucleic acid, 2005, barcoded beads, 2015, and, in some cases, other reagents, e.g., a reducing agent, 2020, are combined and subject to partitioning. In some cases, the reference nucleic acid 2000 may be fragmented prior to partitioning and at least some of the resulting fragments are partitioned as 2005 for barcoding. By way of example, such partitioning may involve introducing the components to a droplet generation system, such as a microfluidic device, 2025. With the aid of the microfluidic device 2025, a water-in-oil emulsion 2030 may be formed, where the emulsion contains aqueous droplets that contain reference nucleic acid, 2005, reducing agent, 2020, and barcoded beads, 2015. The reducing agent may dissolve or degrade the barcoded beads, thereby releasing the oligonucleotides with the barcodes and random N-mers from the beads within the droplets, 2035. The random N-mers may then prime different regions of the reference nucleic acid, resulting in amplified copies of the reference nucleic acid after amplification, where each copy is tagged with a barcode sequence, 2040. In some cases, amplification 2040 may be achieved by a method analogous to that described elsewhere herein and schematically depicted in FIG. 5. In some cases, each droplet contains a set of oligonucleotides that contain identical barcode sequences and different random N-mer sequences. Subsequently, the emulsion is broken, 2045 and additional sequences (e.g., sequences that aid in particular sequencing methods, additional barcodes, etc.) may be added, via, for example, amplification methods, 2050 (e.g., PCR). Sequencing may then be performed, 2055, and an algorithm applied to interpret the sequencing data, 2060. In some cases, interpretation of the sequencing data 2060 may include providing a sequence for at least a portion of the reference nucleic acid. In some cases, long range sequence context for the reference nucleic acid is obtained and characterized such as, for example, in the case where the reference nucleic acid is derived from a disease state (e.g., determination of one or more haplotypes as described elsewhere herein, determination of one or more structural variations (e.g., a copy number variation, an insertion, a deletion, a translocation, an inversion, a rearrangement, a repeat expansion, a duplication, retrotransposon, a gene fusion, etc.), calling of one or more SNPs, etc.). In some cases, variants can be called for various reference nucleic acids obtained from a source and inferred contigs generated to provide longer range sequence context, such as is described elsewhere herein with respect to FIG. 7.

FIG. 21 demonstrates an example of characterizing a sample nucleic acid sequence from the reference 2060 characterization obtained as shown in FIG. 20. Long range sequence context can be obtained for the sample nucleic acid from sequencing of shorter barcoded fragments as is described elsewhere herein, such as, for example, via the method schematically depicted in FIG. 6. As shown in FIG. 21, a nucleic acid sample (e.g., a sample comprising a circulating tumor nucleic acid) can be obtained from a subject suspected of having a disorder or disease (e.g., cancer) 2100 and a set of barcoded beads may also be obtained, 2110. The beads can be linked to oligonucleotides containing one or more barcode sequences, as well as a primer, such as a random N-mer or other primer. In some cases, the barcode sequences are releasable from the barcoded beads, e.g., through cleavage of a linkage between the barcode and the bead or through degradation of the underlying bead to release the barcode, or a combination of the two. For example, in some aspects, the barcoded beads can be degraded or dissolved by an agent, such as a reducing agent to release the barcode sequences. In this example, sample nucleic acid, 2105, barcoded beads, 2115, and, in some cases, other reagents, e.g., a reducing agent, 2120, are combined and subject to partitioning. In some cases, the fetal sample 2100 is fragmented prior to partitioning and at least some of the resulting fragments are partitioned as 2105 for barcoding. By way of example, such partitioning may involve introducing the components to a droplet generation system, such as a microfluidic device, 2125. With the aid of the microfluidic device 2125, a water-in-oil emulsion 2130 may be formed, where the emulsion contains aqueous droplets that contain sample nucleic acid, 2105, reducing agent, 2120, and barcoded beads, 2115. The reducing agent may dissolve or degrade the barcoded beads, thereby releasing the oligonucleotides with the barcodes and random N-mers from the beads within the droplets, 2135. The random N-mers may then prime different regions of the sample nucleic acid, resulting in amplified copies of the sample nucleic acid after amplification, where each copy is tagged with a barcode sequence, 2140. In some cases, amplification 2140 may be achieved by a method analogous to that described elsewhere herein and schematically depicted in FIG. 5. In some cases, each droplet contains a set of oligonucleotides that contain identical barcode sequences and different random N-mer sequences. Subsequently, the emulsion is broken, 2145 and additional sequences (e.g., sequences that aid in particular sequencing methods, additional barcodes, etc.) may be added, via, for example, amplification methods, 2150 (e.g., PCR). Sequencing may then be performed, 2155, and an algorithm applied to interpret the sequencing data, 2160. In some cases, interpretation of the sequencing data 2160 may include providing a sequence of the sample nucleic acid. In some cases, long range sequence context for the nucleic acid sample is obtained. The sample nucleic acid sequence can be characterized 2160 (e.g., determination of one or more haplotypes as described elsewhere herein, determination of one or more structural variations (e.g., a copy number variation, an insertion, a deletion, a translocation, an inversion, a rearrangement, a repeat expansion, a duplication, retrotransposon, a gene fusion, etc.) using the characterization of the reference nucleic acid sequence 2060. Based on the comparison of the sample nucleic acid sequence and its characterization with the sequence and characterization of the reference nucleic acid, a differential diagnosis 2170 regarding the presence (or absence) of the disorder or disease state can be made.

As can be appreciated, analysis of reference nucleic acids and sample nucleic acids may completed as separate partitioning analyses or may be completed as part of a single partitioning analysis. For example, sample and reference nucleic acids may be added to the same device and barcoded sample and reference fragments generated in droplets according to FIGS. 20 and 21, where an emulsion comprises the droplets for both types of nucleic acid. The emulsion can then be broken and the contents of the droplets pooled, further processed (e.g., bulk addition of additional sequences via PCR) and sequenced as described elsewhere herein. Individual sequencing reads from the barcoded fragments can be attributed to their respective sample sequence via barcode sequences. Sequences obtained from the sample nucleic acid can be characterized based upon the characterization of the reference nucleic acid sequence.

Utilizing methods and systems herein can improve accuracy in determining long range sequence context of nucleic acids, including the long-range sequence context of reference and sample nucleic acid sequences as described herein. The methods and systems provided herein may determine long-range sequence context of reference and/or sample nucleic acids with accuracy of at least 70%, 80%, 85%, 90%, 91%, 92%, 93%, 94%, 95%, 99%, 99.1%, 99.2%, 99.3% 99.4%, 99.5%, 99.6%, 99.7%, 99.8%, 99.9%, 99.95%, 99.99%, 99.995%, or 99.999%. In some cases, the methods and systems provided herein may determine long-range sequence context of reference and/or sample nucleic acids with an error rate of less than 10%, 9%, 8%, 7%, 6%, 5%, 4%, 3%, 2%, 1%, 0.1%, 0.05%, 0.01%, 0.005%, 0.001%, 0.0005%, 0.0001%, 0.00005%, 0.00001%, or 0.000005%.

Moreover, methods and systems herein can also improve accuracy in characterizing a reference nucleic acid sequence and/or sample nucleic acid sequence in one or more aspects (e.g., determination of a sequence, determination of one or more genetic variations, determination of haplotypes, etc.). Accordingly, the methods and systems provided herein may characterize a reference nucleic acid sequence and/or sample nucleic acid sequence in one or more aspects with an accuracy of at least 70%, 80%, 85%, 90%, 91%, 92%, 93%, 94%, 95%, 99%, 99.1%, 99.2%, 99.3% 99.4%, 99.5%, 99.6%, 99.7%, 99.8%, 99.9%, 99.95%, 99.99%, 99.995%, or 99.999%. In some cases, the methods and systems provided herein may characterize a reference nucleic acid sequence and/or sample nucleic acid sequence in one or more aspects with an error rate of less than 10%, 9%, 8%, 7%, 6%, 5%, 4%, 3%, 2%, 1%, 0.1%, 0.05%, 0.01%, 0.005%, 0.001%, 0.0005%, 0.0001%, 0.00005%, 0.00001%, or 0.000005%.

Moreover, as is discussed above, improved accuracy in determining long-range sequence context of reference nucleic acids and characterization of the same can result in improved accuracy in sequencing and characterizing sample nucleic acids and subsequent use in differential diagnosis of a disorder or disease. Accordingly, a sample nucleic acid sequence (including long-range sequence context) can be provided from analysis of a reference nucleic acid sequence with an error rate of less than 10%, 9%, 8%, 7%, 6%, 5%, 4%, 3%, 2%, 1%, 0.1%, 0.05%, 0.01%, 0.005%, 0.001%, 0.0005%, 0.0001%, 0.00005%, 0.00001%, or 0.000005%. In some cases, a sample nucleic acid sequence can be used for differential diagnosis of a disorder or disease (or absence thereof) by comparison with a sequence and/or characterization of a sequence of a reference nucleic acid with accuracy of at least 70%, 80%, 85%, 90%, 91%, 92%, 93%, 94%, 95%, 99%, 99.1%, 99.2%, 99.3% 99.4%, 99.5%, 99.6%, 99.7%, 99.8%, 99.9%, 99.95%, 99.99%, 99.995%, or 99.999%. In some cases, a sample nucleic acid sequence can be used for differential diagnosis of a disorder or disease (or absence thereof) by comparison with a sequence and/or characterization of a sequence of a reference nucleic acid with an error rate of less than 10%, 9%, 8%, 7%, 6%, 5%, 4%, 3%, 2%, 1%, 0.1%, 0.05%, 0.01%, 0.005%, 0.001%, 0.0005%, 0.0001%, 0.00005%, 0.00001%, or 0.000005%.

In an example, the methods and systems may be used to detect copy number variation in a patient with lung cancer in order to determine whether the lung cancer is Non-Small Cell Lung Cancer, which is associated with a variation in the EGFR gene. After such diagnosis, a patient's treatment regimen may be refined to correlate with the differential diagnosis. Targeted therapy or molecularly targeted therapy is one of the major modalities of medical treatment (pharmacotherapy) for cancer, others being hormonal therapy and cytotoxic chemotherapy. Targeted therapy blocks the growth of cancer cells by interfering with specific targeted molecules needed for carcinogenesis and tumor growth, rather than by simply interfering with all rapidly dividing cells (e.g. with traditional chemotherapy).

Figure 14:
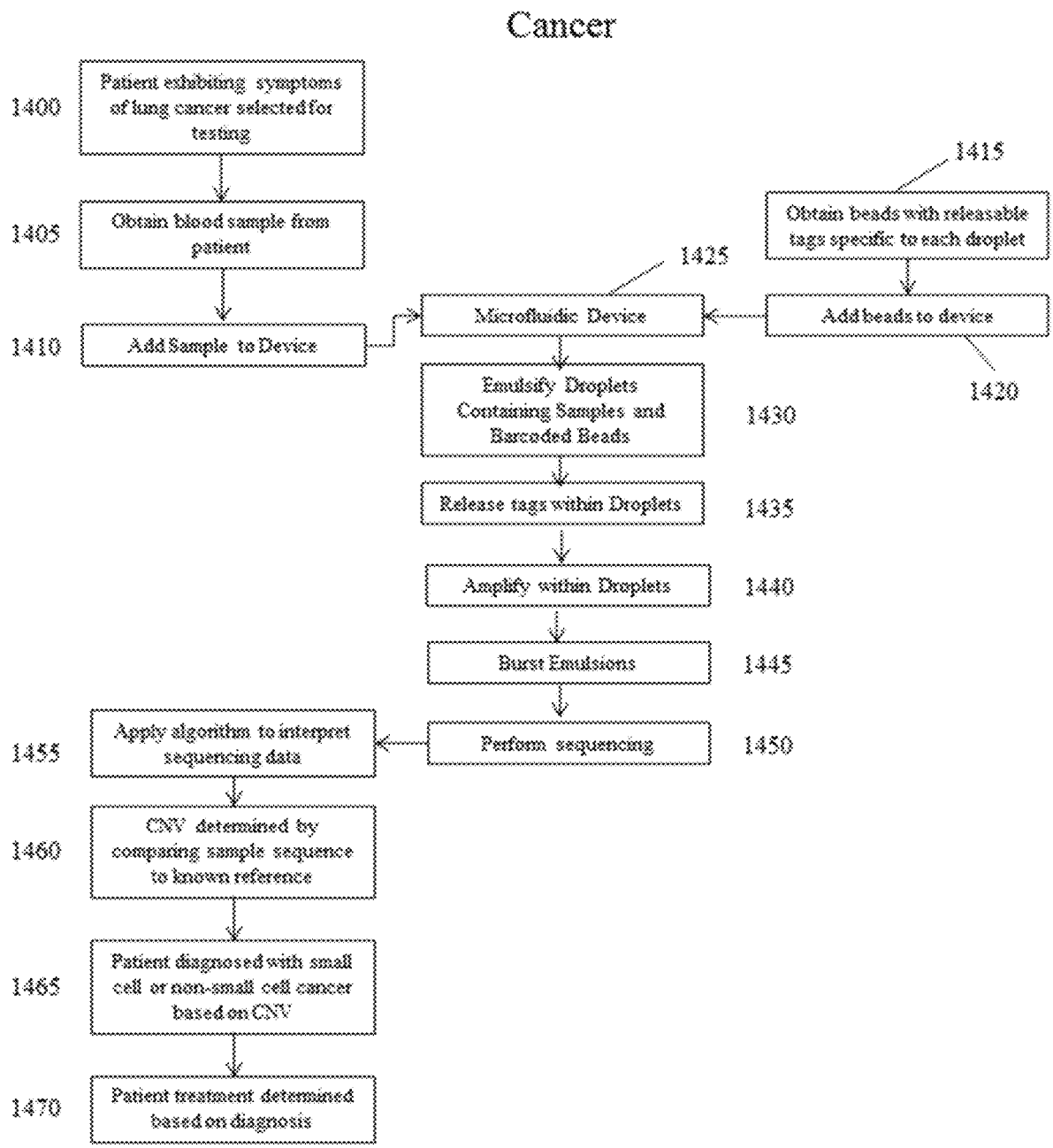
FIG. 14 illustrates an example workflow for performing a cancer diagnostic test based on determination of copy number variation using the methods and compositions described herein.

FIG. 14 shows an exemplary process for differentially diagnosing Non-Small Cell Lung Cancer. A patient with chromic cough, weight loss and shortness of breath is tested for lung cancer 1400. Blood is drawn from the patient 1405 and samples (e.g., circulating tumor cells, cell-free DNA, circulating nucleic acid (e.g., circulating tumor nucleic acid), etc.) are derived from the blood 1410. A set of barcoded beads may also be obtained, 1415. The beads can be linked to oligonucleotides containing one or more barcode sequences, as well as a primer, such as a random N-mer or other primer. In some cases, the barcode sequences are releasable from the barcoded beads, e.g., through cleavage of a linkage between the barcode and the bead or through degradation of the underlying bead to release the barcode, or a combination of the two. For example, in some aspects, the barcoded beads can be degraded or dissolved by an agent, such as a reducing agent to release the barcode sequences. In this example, a sample, 1410, barcoded beads, 1420, and, in some cases, other reagents, e.g., a reducing agent, are combined and subject to partitioning. By way of example, such partitioning may involve introducing the components to a droplet generation system, such as a microfluidic device, 1425. With the aid of the microfluidic device 1425, a water-in-oil emulsion 1430 may be formed, where the emulsion contains aqueous droplets that contain sample nucleic acid, 1410, barcoded beads, 1415, and, in some cases, a reducing agent. The reducing agent may dissolve or degrade the barcoded beads, thereby releasing the oligonucleotides with the barcodes and random N-mers from the beads within the droplets, 1435. The random N-mers may then prime different regions of the sample nucleic acid, resulting in amplified copies of the sample after amplification, where each copy is tagged with a barcode sequence, 1440. In some cases, each droplet contains a set of oligonucleotides that contain identical barcode sequences and different random N-mer sequences. Subsequently, the emulsion is broken, 1445 and additional sequences (e.g., sequences that aid in particular sequencing methods, additional barcodes, etc.) may be added, via, for example, amplification methods (e.g., PCR). Sequencing may then be performed, 1450, and an algorithm applied to interpret the sequencing data, 1455. Sequencing algorithms are generally capable, for example, of performing analysis of barcodes to align sequencing reads and/or identify the sample from which a particular sequence read belongs.

The analyzed sequence is then compared to a known genome reference sequence to determine the CNV of different genes 1460. If the EGFR copy number in the DNA is higher than normal, the patient can be differentially diagnosed with non-small cell lung cancer (NSCLC) instead of small-cell lung cancer 1465. The CTC of non-small cell lung cancer also has other copy number variations that may further distinguish it from small-cell lung cancer. Depending on the stage of the cancer, surgery, chemotherapy, or radiation therapy is prescribed 1470. In some cases, a patient diagnosed with NSLC is administered a drug targeted for such cancer such as an ALK inhibitor (e.g., Crizotinib). In some cases of variations in EGFR, the patient is administered cetuximab, panitumumab, lapatinib, and/or capecitabine. In a different situation, the target may be a different gene, such as ERBB2, and the therapy comprises trastuzumab (Herceptin). (2010) Nature466: 368-72; Cook E. H. and Scherer S. W. (2008) Nature 455: 919-923.

The main categories of targeted therapy are small molecules, small molecule drug conjugates and monoclonal antibodies. Small molecules may include tyrosine-kinase inhibitors such as Imatinib mesylate (Gleevec, also known as STI-571) (which is approved for chronic myelogenous leukemia, gastrointestinal stromal tumor and some other types of cancer); Gefitinib (Iressa, also known as ZD1839) (which targets the epidermal growth factor receptor (EGFR) tyrosine kinase and is approved in the U.S. for non small cell lung cancer); Erlotinib (marketed as Tarceva); Bortezomib (Velcade) (which is an apoptosis-inducing proteasome inhibitor drug that causes cancer cells to undergo cell death by interfering with proteins); tamoxifen; JAK inhibitors (e.g., tofactinib), ALK inhibitors (e.g., crizotinib.); Bcl-2 inhibitors (e.g. obatoclax in clinical trials, ABT-263, and Gossypol); PARP inhibitors (e.g. Iniparib, Olaparib in clinical trials); PI3K inhibitors (e.g. perifosine in a phase III trial). Apatinib (which is a selective VEGF Receptor 2 inhibitor); AN-152, (AEZS-108) doxorubicin linked to [D-Lys(6)]-LHRH; Braf inhibitors (vemurafenib, dabrafenib, LGX818) (used to treat metastatic melanoma that harbors BRAF V600E mutation); MEK inhibitors (trametinib, MEK162); CDK inhibitors, e.g. PD-0332991, LEE011 in clinical trials; Hsp90 inhibitors; and Salinomycin.

Other therapies include Small Molecule Drug Conjugates such as Vintafolide, which is a small molecule drug conjugate consisting of a small molecule targeting the folate receptor. Monoclonal antibodies are another type of therapy that may be administered as part of a method provided herein. Monoclonal drug conjugates may also be administered. Exemplary monoclonal antibodies include: Rituximab (marketed as MabThera or Rituxan)(which targets CD20 found on B cells and targets non Hodgkin lymphoma); Trastuzumab (Herceptin) (which targets the Her2/neu (also known as ErbB2) receptor expressed in some types of breast cancer); Cetuximab (marketed as Erbitux) and Panitumumab Bevacizumab (marketed as Avastin) (which targets VEGF ligand).

VII. Characterizing Fetal Nucleic Acid From Parental Nucleic Acid

As noted elsewhere herein, the methods and systems described herein may also be used to characterize circulating nucleic acids within the blood or plasma of a subject. Such analyses include the analysis of circulating tumor DNA, for use in identification of potential disease states in a patient, or circulating fetal DNA within the blood or plasma of a pregnant female, in order to characterize the fetal DNA in a non-invasive way, e.g., without resorting to direct sampling through amniocentesis or other invasive procedures.

In some cases, the methods may be used to characterize fetal nucleic acid sequences, e.g. circulating fetal DNA, based, at least in part, on analysis of parental nucleic acid sequences. For example, long range sequence context can be determined for both paternal and maternal nucleic acids (e.g., having lengths of longer than 1 kb, longer than 5 kb, longer than 10 kb, longer than 15 kb, longer than 20 kb, longer than 30 kb, longer than 40 kb, longer than 50 kb, longer than 60 kb, longer than 70 kb, longer than 80 kb, longer than 90 kb or even longer than 100 kb) from shorter barcoded fragments using methods and systems described herein. Long range sequence context can be used to determine one or more haplotypes and one or more genetic variations, including single nucleotide polymorphisms (SNPs), structural variations in (e.g., a copy number variation, an insertion, a deletion, a translocation, an inversion, a rearrangement, a repeat expansion, a retrotransposon, a duplication, a gene fusion, etc.) in both the paternal and maternal nucleic acid sequences. Moreover, long range sequence context of paternal and maternal nucleic acids and any determined SNP, haplotype and/or structural variation information can be used to characterize a sequence of a fetal nucleic acid obtained from the pregnant mother (e.g., circulating fetal nucleic acid, such as, for example, cell-free fetal nucleic acid). In some cases, characterizations of a fetal nucleic acid, via comparison with maternal and paternal sequences and characterization, may be completed with the aid of a programmed computer processor. In some cases, such a programmed computer processor can be included in a computer control system, such as in an example computer control system described elsewhere herein.

For example, a sequence and/or long range sequence context of parental and/or maternal nucleic acids may be used as a reference by which to characterize fetal nucleic acid, including a fetal nucleic acid sequence. Indeed, long range sequence context obtained by methods and systems described herein can provide improved, long range sequence context information for paternal and maternal nucleic acids from which fetal nucleic acid sequences can be characterized. In some cases, characterization of a fetal nucleic acid sequence from parental nucleic acids as references may include determining a sequence for at least a portion of a fetal nucleic acid, and/or calling one or more SNPs of a fetal nucleic acid sequence, determining one or more de novo mutations of a fetal nucleic acid sequence, determining one or more haplotypes of a fetal nucleic acid sequence, and/or determining and characterizing one or more structural variations, etc. in a sequence of the fetal nucleic acid.

Figure 17:
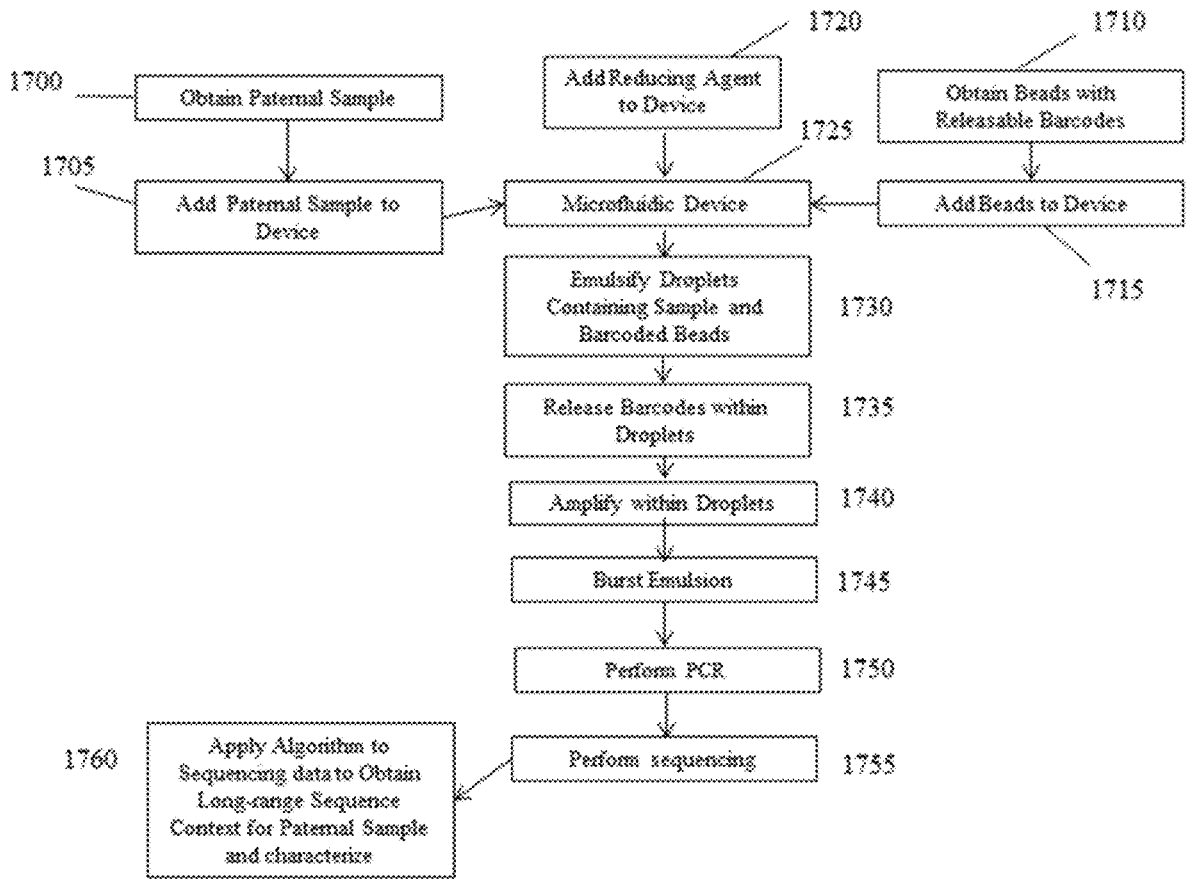
FIG. 17 schematically depicts an example workflow of analyzing a paternal nucleic acid sequence as described herein.
Figure 18:
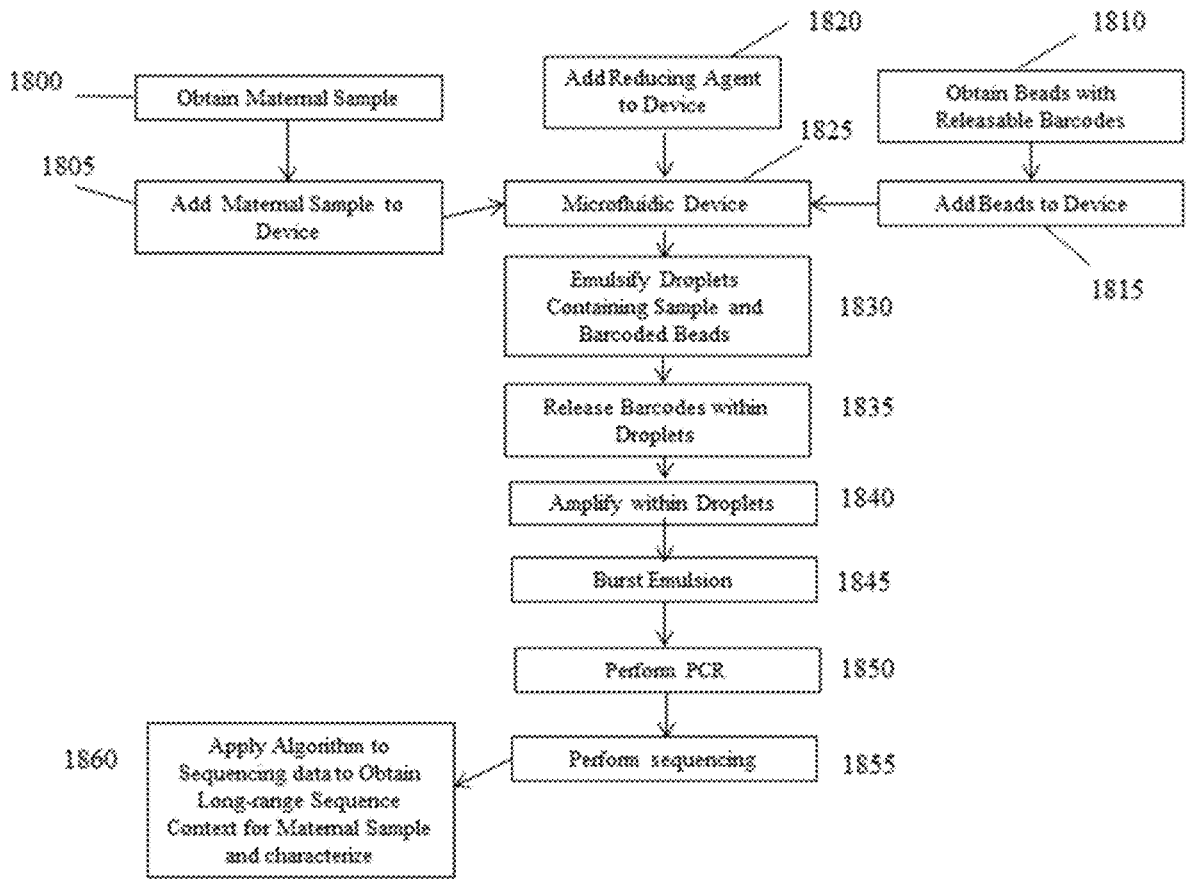
FIG. 18 schematically depicts an example workflow of analyzing a maternal nucleic acid sequence as described herein.
Figure 19:
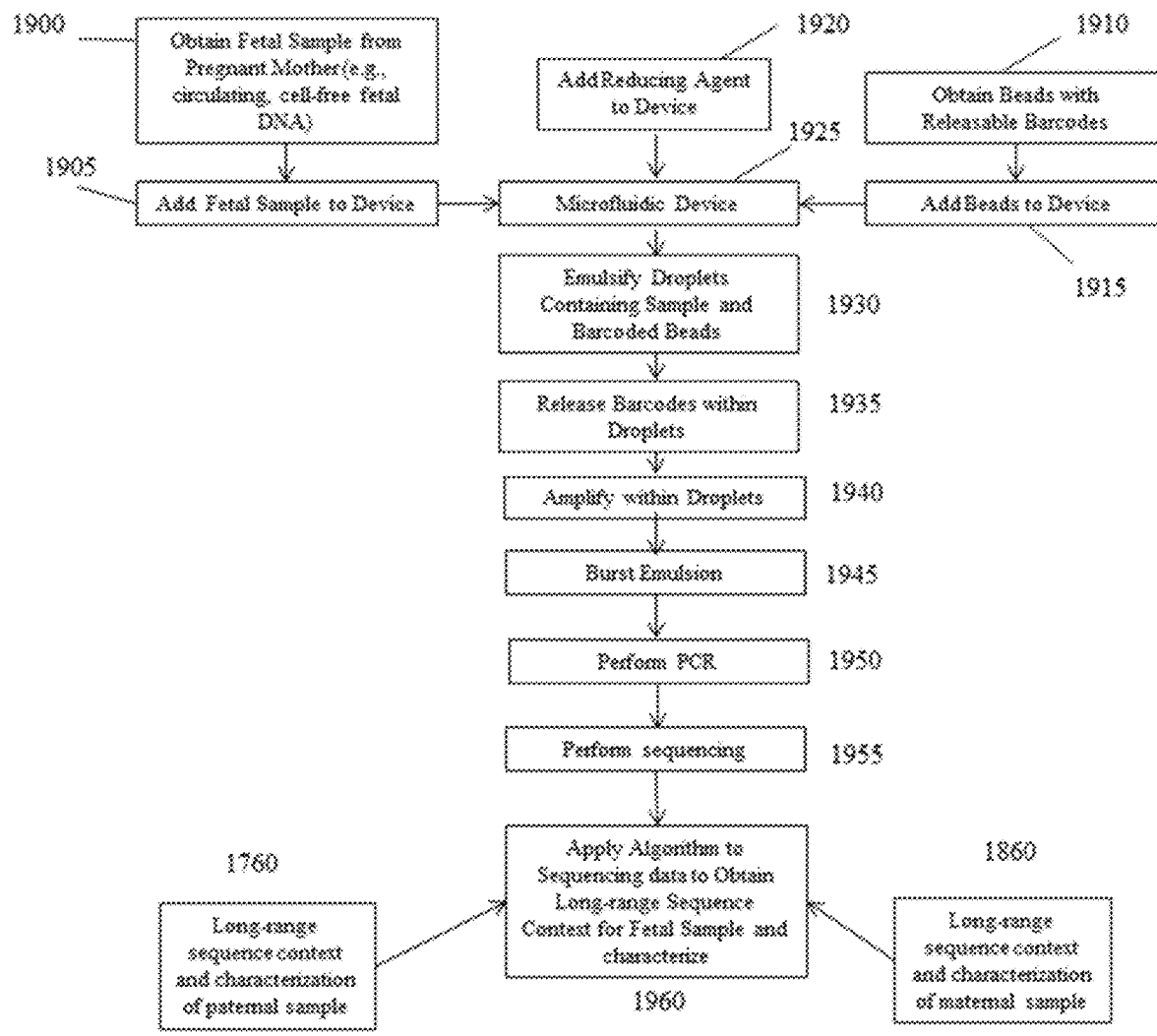
FIG. 19 schematically depicts an example workflow of analyzing a fetal nucleic acid sequence as described herein.

FIGS. 17-19 illustrate an example method for characterizing fetal nucleic acid from longer range sequence context obtained for paternal and maternal nucleic acid, via sequencing of shorter barcoded fragments. FIG. 17 demonstrates an example method by which longer range sequence context can be determined for a paternal nucleic acid sample (e.g., paternal genomic DNA) from shorter barcoded fragments, such as, for example, in a manner analogous to that shown in FIG. 6. With respect to FIG. 17, a sample comprising paternal nucleic acid may be obtained from the father of a fetus, 1700, and a set of barcoded beads may also be obtained, 1710. The beads can be linked to oligonucleotides containing one or more barcode sequences, as well as a primer, such as a random N-mer or other primer. In some cases, the barcode sequences are releasable from the barcoded beads, e.g., through cleavage of a linkage between the barcode and the bead or through degradation of the underlying bead to release the barcode, or a combination of the two. For example, in some aspects, the barcoded beads can be degraded or dissolved by an agent, such as a reducing agent to release the barcode sequences. In this example, paternal sample comprising nucleic acid, 1705, barcoded beads, 1715, and, in some cases, other reagents, e.g., a reducing agent, 1720, are combined and subject to partitioning. In some cases, the paternal sample 1700 is fragmented prior to partitioning and at least some of the resulting fragments are partitioned as 1705 for barcoding. By way of example, such partitioning may involve introducing the components to a droplet generation system, such as a microfluidic device, 1725. With the aid of the microfluidic device 1725, a water-in-oil emulsion 1730 may be formed, where the emulsion contains aqueous droplets that contain paternal sample nucleic acid, 1705, reducing agent, 1720, and barcoded beads, 1715. The reducing agent may dissolve or degrade the barcoded beads, thereby releasing the oligonucleotides with the barcodes and random N-mers from the beads within the droplets, 1735. The random N-mers may then prime different regions of the paternal sample nucleic acid, resulting in amplified copies of the paternal sample after amplification, where each copy is tagged with a barcode sequence, 1740. In some cases, amplification 1740 may be achieved by a method analogous to that described elsewhere herein and schematically depicted in FIG. 5. In some cases, each droplet contains a set of oligonucleotides that contain identical barcode sequences and different random N-mer sequences. Subsequently, the emulsion is broken, 1745 and additional sequences (e.g., sequences that aid in particular sequencing methods, additional barcodes, etc.) may be added, via, for example, amplification methods, 1750 (e.g., PCR). Sequencing may then be performed, 1755, and an algorithm applied to interpret the sequencing data 1760. In some cases, for example, interpretation of sequencing data 1760 may include providing a sequence for at least a portion of the paternal nucleic acid. In some cases, long range sequence context for the paternal nucleic acid sample can be obtained and characterized (e.g., determination of one or more haplotypes as described elsewhere herein, determination of one or more structural variations (e.g., a copy number variation, an insertion, a deletion, a translocation, an inversion, a rearrangement, a repeat expansion, a duplication, a retrotransposon, a gene fusion, etc.), calling of one or more SNPs, determination of one or more other genetic variations, etc.). In some cases, variants can be called for various paternal nucleic acids and inferred contigs generated to provide longer range sequence context, such as is described elsewhere herein with respect to FIG. 7.

FIG. 18 demonstrates an example method by which long range sequence context can be determined for a maternal nucleic acid sample (e.g., maternal genomic DNA) from shorter barcoded fragments, such as, for example, in a manner analogous to that shown in FIG. 6. With respect to FIG. 18, a sample comprising maternal nucleic acid may be obtained from the pregnant mother of a fetus, 1800, and a set of barcoded beads may also be obtained, 1810. The beads can be linked to oligonucleotides containing one or more barcode sequences, as well as a primer, such as a random N-mer or other primer. In some cases, the barcode sequences are releasable from the barcoded beads, e.g., through cleavage of a linkage between the barcode and the bead or through degradation of the underlying bead to release the barcode, or a combination of the two. For example, in some aspects, the barcoded beads can be degraded or dissolved by an agent, such as a reducing agent to release the barcode sequences. In this example, maternal sample comprising nucleic acid, 1805, barcoded beads, 1815, and, in some cases, other reagents, e.g., a reducing agent, 1820, are combined and subject to partitioning. In some cases, the maternal sample 1800 is fragmented prior to partitioning and at least some of the resulting fragments are partitioned as 1805 for barcoding. By way of example, such partitioning may involve introducing the components to a droplet generation system, such as a microfluidic device, 1825. With the aid of the microfluidic device 1825, a water-in-oil emulsion 1830 may be formed, where the emulsion contains aqueous droplets that contain maternal sample nucleic acid, 1805, reducing agent, 1820, and barcoded beads, 1815. The reducing agent may dissolve or degrade the barcoded beads, thereby releasing the oligonucleotides with the barcodes and random N-mers from the beads within the droplets, 1835. The random N-mers may then prime different regions of the maternal sample nucleic acid, resulting in amplified copies of the maternal sample after amplification, where each copy is tagged with a barcode sequence, 1840. In some cases, amplification 1840 may be achieved by a method analogous to that described elsewhere herein and schematically depicted in FIG. 5. In some cases, each droplet contains a set of oligonucleotides that contain identical barcode sequences and different random N-mer sequences. Subsequently, the emulsion is broken, 1845 and additional sequences (e.g., sequences that aid in particular sequencing methods, additional barcodes, etc.) may be added, via, for example, amplification methods, 1850 (e.g., PCR). Sequencing may then be performed, 1855, and an algorithm applied to interpret the sequencing data, 1860. In some cases, for example, interpretation of sequencing data 1860 may include providing a sequence for at least a portion of the maternal nucleic acid. In some cases, long range sequence context for the maternal nucleic acid sample can be obtained and characterized (e.g., determination of one or more haplotypes as described elsewhere herein, determination of one or more structural variations (e.g., a copy number variation, an insertion, a deletion, a translocation, an inversion, a rearrangement, a repeat expansion, a duplication, a retrotransposon, a gene fusion, etc.), calling of one or more SNPs, determination of one or more other genetic variations, etc. In some cases, variants can be called for various maternal nucleic acids obtained from a sample and inferred contigs generated to provide longer range sequence context, such as is described elsewhere herein with respect to FIG. 7.

FIG. 19 demonstrates an example of characterizing a fetal sample sequence from the paternal 1760 and maternal 1860 characterizations obtained as shown in FIG. 17 and FIG. 18, respectively. As shown in FIG. 19, a fetal nucleic acid sample can be obtained from the pregnant mother 1900. Long range sequence context can be obtained for the fetal nucleic acid from sequencing of shorter barcoded fragments as is described elsewhere herein, such as, for example, via the method schematically depicted in FIG. 6. In some cases, the fetal nucleic acid sample may be circulating fetal DNA and/or cell-free DNA that may be, for example, obtained from the pregnant mother's blood, plasma, other bodily fluid, or tissue. A set of barcoded beads may also be obtained, 1910. The beads are can be linked to oligonucleotides containing one or more barcode sequences, as well as a primer, such as a random N-mer or other primer. In some cases, the barcode sequences are releasable from the barcoded beads, e.g., through cleavage of a linkage between the barcode and the bead or through degradation of the underlying bead to release the barcode, or a combination of the two. For example, in some aspects, the barcoded beads can be degraded or dissolved by an agent, such as a reducing agent to release the barcode sequences. In this example, fetal sample comprising nucleic acid, 1905, barcoded beads, 1915, and, in some cases, other reagents, e.g., a reducing agent, 1920, are combined and subject to partitioning as 1905. In some cases, the fetal sample 1900 is fragmented prior to partitioning and at least some of the resulting fragments are partitioned as 1905 for barcoding. By way of example, such partitioning may involve introducing the components to a droplet generation system, such as a microfluidic device, 1925. With the aid of the microfluidic device 1925, a water-in-oil emulsion 1930 may be formed, where the emulsion contains aqueous droplets that contain maternal sample nucleic acid, 1905, reducing agent, 1920, and barcoded beads, 1915. The reducing agent may dissolve or degrade the barcoded beads, thereby releasing the oligonucleotides with the barcodes and random N-mers from the beads within the droplets, 1935. The random N-mers may then prime different regions of the fetal sample nucleic acid, resulting in amplified copies of the fetal sample after amplification, where each copy is tagged with a barcode sequence, 1940. In some cases, amplification 1940 may be achieved by a method analogous to that described elsewhere herein and schematically depicted in FIG. 5. In some cases, each droplet contains a set of oligonucleotides that contain identical barcode sequences and different random N-mer sequences. Subsequently, the emulsion is broken, 1945 and additional sequences (e.g., sequences that aid in particular sequencing methods, additional barcodes, etc.) may be added, via, for example, amplification methods, 1950 (e.g., PCR). Sequencing may then be performed, 1955, and an algorithm applied to interpret the sequencing data, 1960. In general, longer range sequence context for the fetal nucleic acid sample can be obtained from the shorter barcoded fragments that are sequenced. In some cases, for example, interpretation of sequencing data 1960 may include providing a sequence for at least a portion of the fetal nucleic acid. The fetal nucleic acid sequence can be characterized 1960 (e.g., determination of one or more haplotypes as described elsewhere herein, determination of one or more structural variations (e.g., a copy number variation, an insertion, a deletion, a translocation, an inversion, a rearrangement, a repeat expansion, a duplication, retrotransposon, a gene fusion, etc.), determination of one or more de novo mutations, calling of one or more SNPs, etc.) using the long-range sequence contexts and/or characterizations of the paternal 1760 and maternal 1860 samples. In some cases, phase blocks of the fetal nucleic acid can be determined by comparison of the fetal nucleic acid sequence to the maternal and paternal phase blocks.

As can be appreciated, analysis of paternal nucleic acid, maternal nucleic acid and/or fetal nucleic acid may completed as part of separate partitioning analyses or may be completed as part of one or more combined partitioning analyses. For example, paternal, maternal and fetal nucleic acids may be added to the same device and barcoded maternal, paternal and fetal fragments generated in droplets according to FIGS. 17-19, where an emulsion comprises the droplets for the three types of nucleic acid. The emulsion can then be broken and the contents of the droplets pooled, further processed (e.g., bulk addition of additional sequences via PCR) and sequenced as described elsewhere herein. Individual sequencing reads from the barcoded fragments can be attributed to their respective sample sequence via barcode sequences.

In some cases, the sequence of a fetal nucleic acid, including the sequence of the fetal genome, and/or genetic variations in the fetal nucleic acid sequence may be determined from long range paternal and maternal sequence contexts and characterizations obtained using methods and systems described herein. For example, genome sequencing of paternal and maternal genomes, along with sequencing of circulating fetal nucleic acids, may be used to determine a corresponding fetal genome sequence. An example of determining a sequence of genomic fetal nucleic acid from sequence analysis of parental genomes and cell-free fetal nucleic acid can be found in Kitzman et al. (2012 Jun. 6) Sci Transl. Med. 4(137): 137ra76, which is herein entirely incorporated by reference. Determination of a fetal genome may be useful in the prenatal determination and diagnosis of genetic disorders in the fetus, including, for example, fetal aneuploidy. As discussed elsewhere herein, methods and systems provided herein can be useful in resolving haplotypes in nucleic acid sequences. Haplotype-resolved paternal and maternal sequences can be determined for paternal and maternal sample nucleic acid sequences, respectively which can aid in more accurately determining the sequence of a fetal genome and/or characterizing the same.

Utilizing methods and systems herein can improve accuracy in determining long range sequence context of nucleic acids, including the long-range sequence context of parental nucleic acid sequences (e.g., maternal nucleic acid sequences, paternal nucleic acid sequences). The methods and systems provided herein may determine long-range sequence context of parental nucleic acids with accuracy of at least 70%, 80%, 85%, 90%, 91%, 92%, 93%, 94%, 95%, 99%, 99.1%, 99.2%, 99.3% 99.4%, 99.5%, 99.6%, 99.7%, 99.8%, 99.9%, 99.95%, 99.99%, 99.995%, or 99.999%. In some cases, the methods and systems provided herein may determine long-range sequence context of parental nucleic acids with an error rate of less than 10%, 9%, 8%, 7%, 6%, 5%, 4%, 3%, 2%, 1%, 0.1%, 0.05%, 0.01%, 0.005%, 0.001%, 0.0005%, 0.0001%, 0.00005%, 0.00001%, or 0.000005%. Moreover, methods and systems herein can also improve accuracy in characterizing a paternal nucleic acid sequence in one or more aspects (e.g., determination of a sequence, determination of one or more genetic variations, determination of one or more structural variants, determination of haplotypes, etc.). Accordingly, the methods and systems provided herein may characterize a paternal nucleic acid sequence in one or more aspects with an accuracy of at least 70%, 80%, 85%, 90%, 91%, 92%, 93%, 94%, 95%, 99%, 99.1%, 99.2%, 99.3% 99.4%, 99.5%, 99.6%, 99.7%, 99.8%, 99.9%, 99.95%, 99.99%, 99.995%, or 99.999%. In some cases, the methods and systems provided herein may characterize a parental nucleic acid sequence in one or more aspects with an error rate of less than 10%, 9%, 8%, 7%, 6%, 5%, 4%, 3%, 2%, 1%, 0.1%, 0.05%, 0.01%, 0.005%, 0.001%, 0.0005%, 0.0001%, 0.00005%, 0.00001%, or 0.000005%.

Moreover, as is discussed above, improved accuracy in determining long-range sequence context of parental nucleic acids and characterization of the same can result in improved accuracy in sequencing and characterizing fetal nucleic acids. Accordingly, in some cases, a fetal nucleic acid sequence (including long-range sequence context) can be provided from analysis of parental nucleic sequences with accuracy of at least 70%, 80%, 85%, 90%, 91%, 92%, 93%, 94%, 95%, 99%, 99.1%, 99.2%, 99.3% 99.4%, 99.5%, 99.6%, 99.7%, 99.8%, 99.9%, 99.95%, 99.99%, 99.995%, or 99.999%. In some cases, a fetal nucleic acid sequence (including long-range sequence context) can be provided from analysis of parental nucleic sequences with an error rate of less than 10%, 9%, 8%, 7%, 6%, 5%, 4%, 3%, 2%, 1%, 0.1%, 0.05%, 0.01%, 0.005%, 0.001%, 0.0005%, 0.0001%, 0.00005%, 0.00001%, or 0.000005%. In some cases, a fetal nucleic acid sequence can be characterized in one or more aspects via analysis of parental nucleic acid sequences as described herein (e.g., determination of a sequence, determination of one or more genetic variations, determination of one or more structural variations, determination of haplotypes, etc.) with accuracy of at least 70%, 80%, 85%, 90%, 91%, 92%, 93%, 94%, 95%, 99%, 99.1%, 99.2%, 99.3% 99.4%, 99.5%, 99.6%, 99.7%, 99.8%, 99.9%, 99.95%, 99.99%, 99.995%, or 99.999%. In some cases, a fetal nucleic acid sequence can be characterized in one or more aspects via analysis of parental nucleic acid sequences as described herein (e.g., determination of a sequence, determination of one or more genetic variations, determination of haplotypes, determination of one or more structural variations, etc.) with an error rate of less than 10%, 9%, 8%, 7%, 6%, 5%, 4%, 3%, 2%, 1%, 0.1%, 0.05%, 0.01%, 0.005%, 0.001%, 0.0005%, 0.0001%, 0.00005%, 0.00001%, or 0.000005%.

VIII. Samples

Detection of a disease or disorder may begin with obtaining a sample from a patient. The term "sample," as used herein, generally refers to a biological sample. Examples of biological samples include nucleic acid molecules, amino acids, polypeptides, proteins, carbohydrates, fats, or viruses. In an example, a biological sample is a nucleic acid sample including one or more nucleic acid molecules. Exemplary samples may include polynucleotides, nucleic acids, oligonucleotides, cell-free nucleic acid (e.g., cell-free DNA (cfDNA)), circulating cell-free nucleic acid, circulating tumor nucleic acid (e.g., circulating tumor DNA (ctDNA)), circulating tumor cell (CTC) nucleic acids, nucleic acid fragments, nucleotides, DNA, RNA, peptide polynucleotides, complementary DNA (cDNA), double stranded DNA (dsDNA), single stranded DNA (ssDNA), plasmid DNA, cosmid DNA, chromosomal DNA, genomic DNA (gDNA), viral DNA, bacterial DNA, mtDNA (mitochondrial DNA), ribosomal RNA, cell-free DNA, cell free fetal DNA (cffDNA), mRNA, rRNA, tRNA, nRNA, siRNA, snRNA, snoRNA, scaRNA, microRNA, dsRNA, viral RNA, and the like. In summary, the samples that are used may vary depending on the particular processing needs.

Any substance that comprises nucleic acid may be the source of a sample. The substance may be a fluid, e.g., a biological fluid. A fluidic substance may include, but not limited to, blood, cord blood, saliva, urine, sweat, serum, semen, vaginal fluid, gastric and digestive fluid, spinal fluid, placental fluid, cavity fluid, ocular fluid, serum, breast milk, lymphatic fluid, or combinations thereof. The substance may be solid, for example, a biological tissue. The substance may comprise normal healthy tissues, diseased tissues, or a mix of healthy and diseased tissues. In some cases, the substance may comprise tumors. Tumors may be benign (non-cancer) or malignant (cancer). Non-limiting examples of tumors may include: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's, leiomyosarcoma, rhabdomyosarcoma, gastrointestinal system carcinomas, colon carcinoma, pancreatic cancer, breast cancer, genitourinary system carcinomas, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, endocrine system carcinomas, testicular tumor, lung carcinoma, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, or combinations thereof. The substance may be associated with various types of organs. Non-limiting examples of organs may include brain, liver, lung, kidney, prostate, ovary, spleen, lymph node (including tonsil), thyroid, pancreas, heart, skeletal muscle, intestine, larynx, esophagus, stomach, or combinations thereof. In some cases, the substance may comprise a variety of cells, including but not limited to: eukaryotic cells, prokaryotic cells, fungi cells, heart cells, lung cells, kidney cells, liver cells, pancreas cells, reproductive cells, stem cells, induced pluripotent stem cells, gastrointestinal cells, blood cells, cancer cells, bacterial cells, bacterial cells isolated from a human microbiome sample, etc. In some cases, the substance may comprise contents of a cell, such as, for example, the contents of a single cell or the contents of multiple cells. Methods and systems for analyzing individual cells are provided in, e.g., U.S. Provisional Patent Application No. 62/017,558, filed Jun. 26, 2014, the full disclosure of which is hereby incorporated by reference in its entirety.

Samples may be obtained from various subjects. A subject may be a living subject or a dead subject. Examples of subjects may include, but not limited to, humans, mammals, non-human mammals, rodents, amphibians, reptiles, canines, felines, bovines, equines, goats, ovines, hens, avines, mice, rabbits, insects, slugs, microbes, bacteria, parasites, or fish. In some cases, the subject may be a patient who is having, suspected of having, or at a risk of developing a disease or disorder. In some cases, the subject may be a pregnant woman. In some case, the subject may be a normal healthy pregnant woman. In some cases, the subject may be a pregnant woman who is at a risking of carrying a baby with certain birth defect.

A sample may be obtained from a subject by various approaches. For example, a sample may be obtained from a subject through accessing the circulatory system (e.g., intravenously or intra-arterially via a syringe or other apparatus), collecting a secreted biological sample (e.g., saliva, sputum urine, feces, etc.), surgically (e.g., biopsy) acquiring a biological sample (e.g., intra-operative samples, post-surgical samples, etc.), swabbing (e.g., buccal swab, oropharyngeal swab), or pipetting.

CNVs can be associated with efficacy of a therapy. For example, increased HER2 gene copy number can enhance the response to gefitinib therapy in advanced non-small cell lung cancer. See Cappuzzo F. et al. (2005) J. Clin. Oncol. 23: 5007-5018. High EGFR gene copy number can predict for increased sensitivity to lapatinib and capecitabine. See Fabi et al. (2010) J. Clin. Oncol. 28:15s (2010 ASCO Annual Meeting). High EGFR gene copy number is associated with increased sensitivity to cetuximab and panitumumab.

Copy number variations can be associated with resistance of cancer patients to certain therapeutics. For example, amplification of thymidylate synthase can result in resistance to 5-fluorouracil treatment in metastatic colorectal cancer patients. See Wang et al. (2002) PNAS USA vol. 99, pp. 16156-61.

IX. Computer Control Systems

Figure 22:
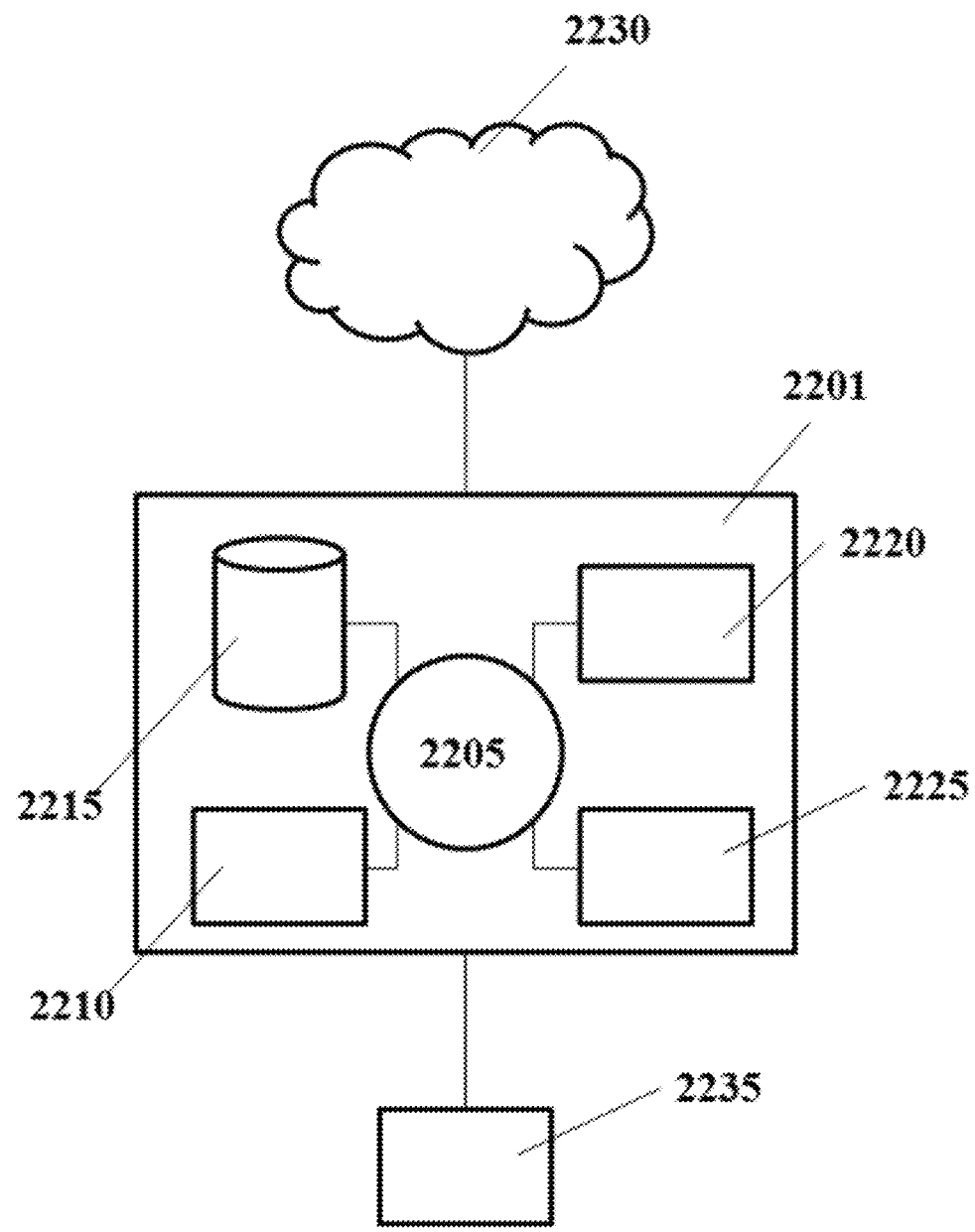
FIG. 22 schematically depicts an example computer control system.

The present disclosure provides computer systems that are programmed or otherwise configured to implement methods provided herein, such as, for example, methods for nucleic sequencing and determination of genetic variations, storing reference nucleic acid sequences, conducting sequence analysis and/or comparing sample and reference nucleic acid sequences as described herein. An example of such a computer system is shown in FIG. 22. As shown in FIG. 22, the computer system 2201 includes a central processing unit (CPU, also "processor" and "computer processor" herein) 2205, which can be a single core or multi core processor, or a plurality of processors for parallel processing. The computer system 2201 also includes memory or memory location 2210 (e.g., random-access memory, read-only memory, flash memory), electronic storage unit 2215 (e.g., hard disk), communication interface 2220 (e.g., network adapter) for communicating with one or more other systems, and peripheral devices 2225, such as cache, other memory, data storage and/or electronic display adapters. The memory 2210, storage unit 2215, interface 2220 and peripheral devices 2225 are in communication with the CPU 2205 through a communication bus (solid lines), such as a motherboard. The storage unit 2215 can be a data storage unit (or data repository) for storing data. The computer system 2201 can be operatively coupled to a computer network ("network") 2230 with the aid of the communication interface 2220. The network 2230 can be the Internet, an internet and/or extranet, or an intranet and/or extranet that is in communication with the Internet. The network 2230 in some cases is a telecommunication and/or data network. The network 2230 can include one or more computer servers, which can enable distributed computing, such as cloud computing. The network 2230, in some cases with the aid of the computer system 2201, can implement a peer-to-peer network, which may enable devices coupled to the computer system 2201 to behave as a client or a server.

The CPU 2205 can execute a sequence of machine-readable instructions, which can be embodied in a program or software. The instructions may be stored in a memory location, such as the memory 2210. Examples of operations performed by the CPU 2205 can include fetch, decode, execute, and writeback.

The storage unit 2215 can store files, such as drivers, libraries and saved programs. The storage unit 2215 can store user data, e.g., user preferences and user programs. The computer system 2201 in some cases can include one or more additional data storage units that are external to the computer system 2201, such as located on a remote server that is in communication with the computer system 2201 through an intranet or the Internet.

The computer system 2201 can communicate with one or more remote computer systems through the network 2230. For instance, the computer system 2201 can communicate with a remote computer system of a user (e.g., operator). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 2201 via the network 2230.

Methods as described herein can be implemented by way of machine (e.g., computer processor) executable code stored on an electronic storage location of the computer system 2201, such as, for example, on the memory 2210 or electronic storage unit 2215. The machine executable or machine readable code can be provided in the form of software. During use, the code can be executed by the processor 2205. In some cases, the code can be retrieved from the storage unit 2215 and stored on the memory 2210 for ready access by the processor 2205. In some situations, the electronic storage unit 2215 can be precluded, and machine-executable instructions are stored on memory 2210.

The code can be pre-compiled and configured for use with a machine have a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 2201, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 2201 can include or be in communication with an electronic display 2235 that comprises a user interface (UI) for providing, for example, an output or readout of a nucleic acid sequencing instrument coupled to the computer system 2201. Such readout can include a nucleic acid sequencing readout, such as a sequence of nucleic acid bases that comprise a given nucleic acid sample. The UI may also be used to display the results of an analysis making use of such readout. Examples of UI's include, without limitation, a graphical user interface (GUI) and web-based user interface. The electronic display 2235 can be a computer monitor, or a capacitive or resistive touchscreen.

EXAMPLES

Example 1: Identification of Phased Variants

Genomic DNA from the NA12878 human cell line was subjected to size based separation of fragments using a Blue Pippin DNA sizing system to recover fragments that were approximately 10 kb in length. The size selected sample nucleic acids were then copartitioned with barcode beads in aqueous droplets within a fluorinated oil continuous phase using a microfluidic partitioning system (see e.g., U.S. Provisional Patent Application No. 61/977,804, filed Apr. 10, 2014, and incorporated herein by reference in its entirety for all purposes), where the aqueous droplets also included the dNTPs, thermostable DNA polymerase and other reagents for carrying out amplification within the droplets, as well as a chemical activator for releasing the barcode oligonucleotides from the beads. This was repeated both for 1 ng of total input DNA and 2 ng of total input DNA. The barcode beads were obtained as a subset of a stock library that represented barcode diversity of over 700,000 different barcode sequences. The barcode containing oligonucleotides included additional sequence components and had the general structure:

Bead-P5-BC-R1-Nmer

Where P5 and R1 refer to the Illumina attachment and Read1 primer sequences, respectively, BC denotes the barcode portion of the oligonucleotide, and N-mer denotes a random 10 base N-mer priming sequence used to prime the template nucleic acids. See, e.g., U.S. patent application Ser. No. 14/316,383, filed Jun. 26, 2014, the full disclosure of which is hereby incorporated herein by reference in its entirety for all purposes.

Following bead dissolution, the droplets were thermocycled to allow for primer extension of the barcode oligos against the template of the sample nucleic acids within each droplet. This resulted in copied fragments of the sample nucleic acids that included the barcode sequence representative of the originating partition, in addition to the other included sequences set forth above.

After barcode labeling of the copy fragments, the emulsion of droplets including the amplified copy fragments was broken and the additional sequencer required components, e.g., read2 primer sequence and P7 attachment sequence for Illumina sequencer, were added to the copy fragments through additional amplification, which attached these sequences to the other end of the copy fragments.

The sequencing library was then sequenced on an Illumina HiSeq system at 10× coverage, 20× coverage and 30× coverage, and the resulting sequence reads and their associated barcode sequences were then analyzed. Proximally mapping sequences that shared common barcodes were then assembled into larger contigs, and single nucleotide polymorphisms were identified and associated with individual starting molecules based upon their associated barcodes and sequence mapping, to identify phased SNPs. Sequences that included overlapping phased SNPs were then assembled into phase blocks or inferred contigs of phased sequence data based upon the overlapping phased SNPs. The resulting data was compared to known haplotype maps for the cell line for comparison.

In at least one approach, each allele of a series of heterozygous variants is assigned to one of two to two haplotypes. A log-likelihood function log P(barcoded reads|phasing assignment, variants) is defined that returns the log-likelihood of the observed read and barcode data, given a set of variants, and a phasing assignment of the heterozygous variants. The form of the log-likelihood function derives from two main observations about barcoded sequence read data: (1) The reads from one barcode cover a small fraction of a haploid genome, so the probability of one barcode containing reads for both haplotypes in a given region of the genome is small. Conversely, the reads for one barcode in a local region of the genome are very likely to come from a single haplotype; (2) the probability that an observed base differs from the true base in haplotype it was derived from is described by the Phred QV of the observed base assigned by the sequencer.

The phasing configuration that maximizes the log-likelihood function, for a given set of barcoded reads and variants is then reported. The maximum-likelihood scoring haplotype configuration is then found by a structured search procedure. First, a beam search is used to find an optimal phasing configuration of a small block of neighboring variants (e.g., ~50 variants). Second the relative phasing of the blocks is determined in a sweep over the block junctions. At this point an overall near-optimal phasing configuration is found and is used as a starting point for further optimization. The haplotype assignment of individual variants is then inverted to find local improvement to the phasing, the difference in the log-likelihood between the swapped configurations provides an estimate of the confidence of that phasing assignment. Finally the phasing configuration is broken into phase blocks that have a high probability of being internally correct. It is then tested whether to break a phase block at each SNP by comparing the log-likelihoods of the optimal configuration with a configuration where all SNPs right of the current SNP have their haplotype assignment inverted.

The table below, provides the phasing metrics obtained for the NA 12878 genome. As is apparent, extremely long phase blocks are obtained from short read sequence data, correctly identifying significant percentages of phased SNPs, with very low short or long switch errors.

|  | 10X Coverage | 20X Coverage | 30X Coverage | 30X Beam Search |
|---|---|---|---|---|
| N50 Phase Block | 193 kb | 385 kb | 428 kb | 489 kb |
| Longest Phase Block | 2121 kb | 2514 kb | 2514 kb | 3027 kb |
| Long Switch Error | 0.0053 | 0.0021 | 0.0018 | 0.0015 |
| Short Switch Error | 0.004 | 0.0017 | 0.0014 | 0.0012 |
| SNPs Phased | 83% | 94% | 95% | 95.2% |

Further experiments phased SNPs from a number of additional samples including the NA12878 trio (NA12878, NA12882 and NA12877), Gujarati (NA20847), Mexican (NA19662) and African (NA19701) cell line samples. N50 phase block lengths of approximately 1MB were achieved with greater than 95% of the SNPs phased with switch errors of less than 0.3%. Whole exome sequencing of the same samples, e.g., where targeted pull down followed the barcoding, showed genic SNP phasing of approximately 90% again with switch errors of less than 0.3%.

Example 2: Identification of EML-4/ALK Gene Inversions/Translocations

Figure 15:
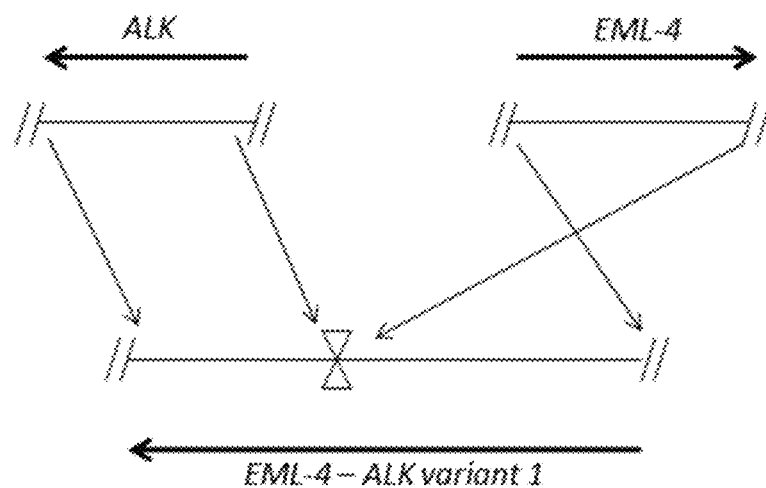
FIG. 15 provides a schematic illustration of an EML-4-ALK structural variation from an NCI-H2228 cancer cell line.
Figure 15:
Figure 15:

The methods and processes described herein were used to detect structural variations from a characterized cancer cell line. In particular, NCI-H2228 lung cancer cell line is known to have an EML4-ALK fusion translocation within its genome. The structure of the variation compared to wild type is illustrated in FIG. 15. As shown in the top panel, in the variant structure, the EML-4 gene, while on the same chromosome, is relatively separate or distant from the ALK gene, is instead translocated and fused to the ALK gene (See e.g., Choi, et al., *Identification of Novel Isoforms of the EML4-LK Transforming Gene in Non-Small Cell Lung Cancer*, J. Cancer Res., 68:4971 (July 2008)). In conjunction with the translocation, the EML4 gene is also inverted. The translocation is further illustrated in Panel II, as compared to the wild type structure, where the translocation results in the fusion of exons 1-6 of EML-4 (shown as black boxes) to exons 20-29 of ALK (shown as white boxes), as well as the fusion of exons 7-23 of ALK fused to exons 1-19 of the EML-4.

In order to identify this variation, genomic DNA from the NCI-H2228 cell line was subjected to size separation using a Blue Pippin® system (Sage Sciences, Inc.), to select for fragments of approximately 10 kb in length.

Figure 16A:
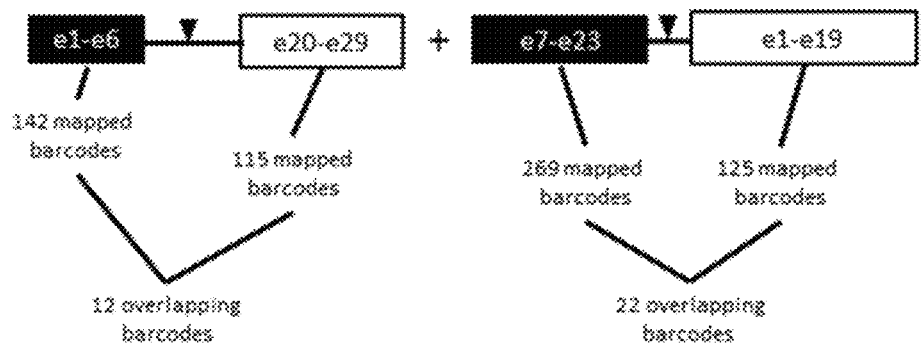
FIGS. 16A and 16B, provide barcode mapping data using the systems described herein for identifying the presence of the EML-4-ALK variant structure shown in FIG. 15, in the cancer cell line (FIG. 16A), as compared to a negative control cell line (FIG. 16B).
Figure 16A:
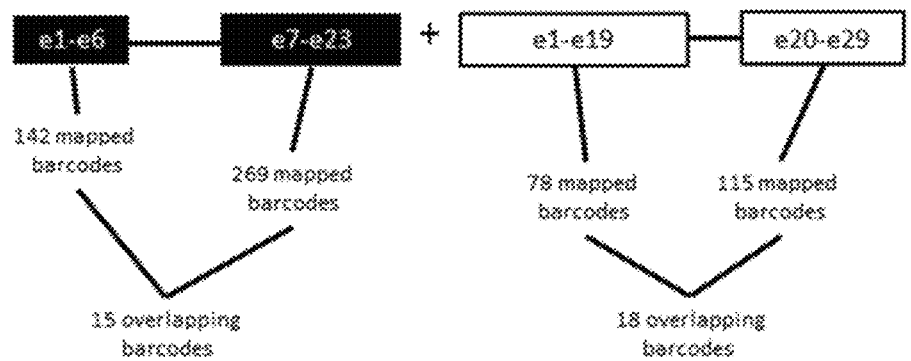

The size selected sample nucleic acids were then copartitioned with barcode beads, amplified and processed into a sequencing library as described above for Example 1, except that the DNA was subjected to hybrid capture using an Agilent SureSelect Exome capture kit after barcoding and prior to sequencing. The sequencing library was then sequenced to approximately 80× coverage on an Illumina HiSeq system and the resulting sequence reads and their associated barcode sequences were then analyzed. The higher number of shared barcodes among portions of the genome that span the translocation event was clearly evident as compared to the wild type, illustrating structural proximity between the fused components where not present in the wild type. In particular, and as shown in FIG. 16A, the fusion structure showed barcode overlap between EML-4 exons 1-6 and ALK exons 20-29, of 12 barcodes, and between EML-4 exons 7-23 and ALK exons 1-19, of 20 barcodes, that were comparable to the overlapping barcodes for the wild type construct for the heterozygous cell line.

Figure 16B:
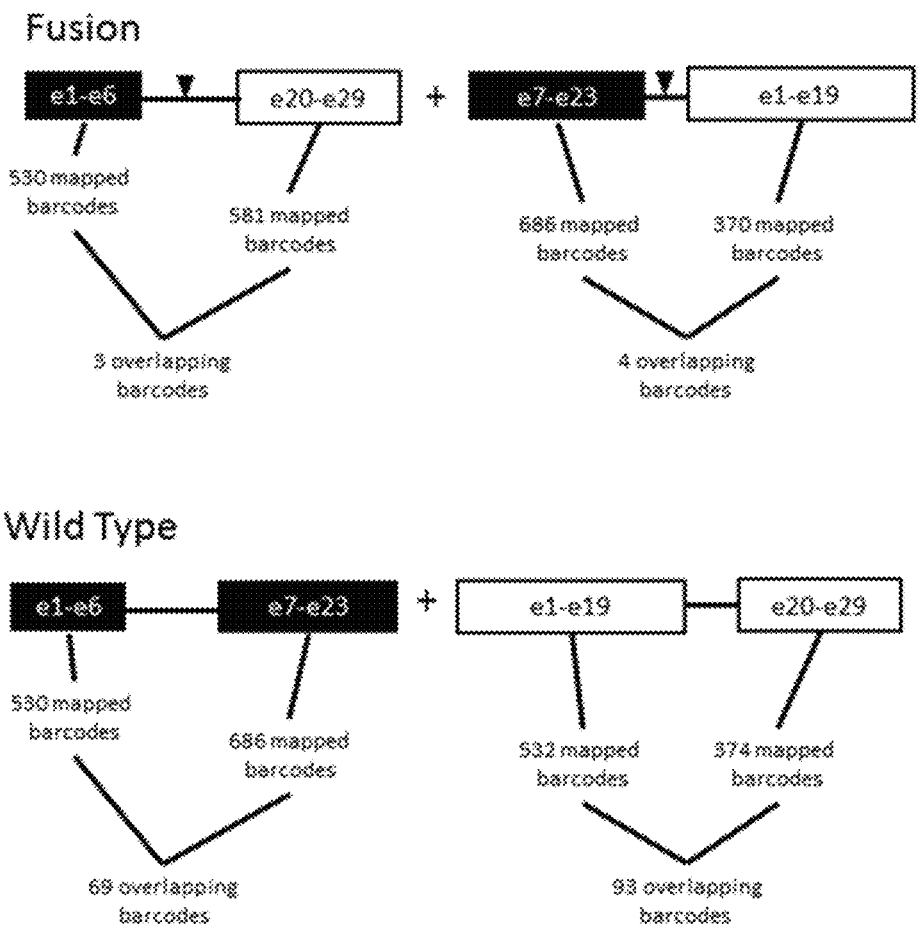

In contrast, a negative control run using a non variant cell line (NA12878) showed substantially only barcode overlap for the wild type vs. the variant construct, as shown in FIG. 16B, with sequence coverage of approximately 140×, and using 3 ng of starting DNA.

In particular, though displaying large numbers of total mapped barcodes to the various sequence segments, only a very small percentage of overlapping barcodes, e.g., less than 0.5% of the total mapped barcoded sequences, were seen for the fusion structure by comparison to the wild type structure which demonstrated very high numbers of common or overlapping barcodes. As a result, the commonly mapping barcodes across fusion or translocation break points provides a powerful basis for identifying those translocation events.

An algorithm for SV detection was also employed that first searches for all pairs of genomic loci with significant barcode intersection/overlap, encoding this search as an efficient sparse matrix-multiplication. Candidates from this first stage are then filtered utilizing a probabilistic model that incorporates read-pair, split-read, and barcode data. SV-calling on NA12878 and NA20847, resulted in calling multiple large-scale deletions and inversions and phasing them with respect to adjacent phase blocks, showing consistency of phasing with inheritance patterns in the nuclear trio descried above.

Example 3: Detecting Increased Susceptibility to Lupus via CNV Screening

A patient is tested for susceptibility to lupus. Blood is drawn from the patient. A cell-free DNA sample is sequenced using techniques recited herein. The sequence is then compared to a known genome reference sequence to determine the CNV of different genes. A low copy number of FCGR3B (the CD16 cell surface immunoglobulin receptor) indicates an increased susceptibility to systemic lupus erythematosus. The patient is informed of any copy number aberrations and the associated risks/disease.

Example 4: Detecting Increased Predisposition to Neuroblastoma via CNV Screening A patient is tested for predisposition to neuroblastoma. Blood is drawn from the patient. A cell-free DNA sample is sequenced using techniques recited herein. The sequence is then compared to a known genome reference sequence to determine the CNV of different genes. CNV at 1q21.1 indicates an increased predisposition to neuroblastoma. The patient is informed of any copy number aberrations and the associated risks/disease.

Example 5: Differential Diagnosis of Lung Cancer via CNV Screening

A patient with chromic cough, weight loss and shortness of breath is tested for lung cancer. Blood is drawn from the patient. The circulating tumor cell (CTC) or cell-free DNA sample is sequenced using techniques recited herein. The CTC sequence is then compared to a known genome reference sequence to determine the CNV of different genes. If the EGFR copy number in the DNA is higher than normal, the patient can be differentially diagnosed with non-small cell lung cancer (NSCLC) instead of small-cell lung cancer. The CTC of non-small cell lung cancer also has other copy number variations that may further distinguish it from small-cell lung cancer. Depending on the stage of the cancer, surgery, chemotherapy, or radiation therapy is prescribed.

Small cell lung cancer is most often more rapidly and widely metastatic than non-small cell lung carcinoma (and hence staged differently). NSCLCs are usually not very sensitive to chemotherapy and/or radiation, so surgery is the treatment of choice if diagnosed at an early stage, often with adjuvant (ancillary) chemotherapy involving cisplatin. Targeted therapy may also be available for patients with non-small cell lung cancer (NSCLC), for example ALK inhibitors such as Crizotinib. Targeted therapy blocks the growth of cancer cells by interfering with specific targeted molecules needed for carcinogenesis and tumor growth, rather than by simply interfering with all rapidly dividing cells (e.g. with traditional chemotherapy).

Example 6: Differential Diagnosis of Fetal Aneuploidies via Phasing

Fetal aneuploidies are aberrations in chromosome number. Aneuploidies commonly result in significant physical and neurological impairments. A reduction in the number of X chromosomes is responsible for Turner's syndrome. An increase in copy number of chromosome number 21 results in Down's syndrome. Invasive testing such as amniocentesis or Chorionic Villus Sampling (CVS) can lead to risk of pregnancy loss and less invasive methods of testing the maternal blood are used here.

A pregnant patient with a family history of Down's syndrome or Turner's syndrome is tested. A maternal blood sample containing fetal genetic material is collected. The nucleic acids from different chromosomes are then separated into different partitions along with barcoded tag molecules as described herein. The samples are then sequenced and the number of each chromosome copies is compared to a sequence on a normal diploid chromosome. The patient is informed of any copy number aberrations for different chromosomes and the associated risks/disease.

Example 7: Detecting Chromosomal Translocations via Phasing for Differential Diagnosis of Burkitt's Lymphoma Burkitt's Lymphoma is characterized by a t(8;14) translocation in the chromosomes. A patient generally diagnosed with lymphoma is tested for Burkitt's Lymphoma. A tumor-biopsy specimen is collected from the lymph node. The nucleic acids from different chromosomes are the separated into different partitions along with barcoded tag molecules as described herein. The samples are then sequenced and compared to a control DNA sample to detect chromosomal translocation. If the patient is diagnosed as having Burkitt's Lymphoma, a more intensive chemotherapy regimen, including the CHOP or R-CHOP regimen, can be required than with other types of lymphoma. CHOP consists of: Cyclophosphamide, an alkylating agent which damages DNA by binding to it and causing the formation of cross-links; Hydroxydaunorubicin (also called doxorubicin or Adriamycin), an intercalating agent which damages DNA by inserting itself between DNA bases; Oncovin (vincristine), which prevents cells from duplicating by binding to the protein tubulin; Prednisone or prednisolone, which are corticosteroids. This regimen can also be combined with the monoclonal antibody rituximab since Burkitt's the lymphoma is of B cell origin; this combination is called R-CHOP.

Example 8: Phasing a Fetal Genome Sequence Derived from Cell-Free DNA by Comparison to Parental Genomes A sample comprising maternal DNA from a pregnant patient and a sample comprising paternal DNA from the father of the fetus are collected. The nucleic acids from each sample are separated into different partitions along with molecular barcoded tags as described herein. The samples are then sequenced and the sequences are used to generate inferred contigs for each of the partitioned maternal and paternal fragments. The inferred contigs are used to construct haplotype blocks for portions of each of the maternal and paternal chromosomes.

A maternal blood sample containing fetal genetic material is collected. The cell-free DNA is sequenced to generate a sequences of both the maternal circulating DNA and the fetal circulating DNA. The reads are compared to the paternal and maternal phase blocks generated above. Some phase blocks have undergone recombination during meiosis. The fetal material is identified that matches the paternal phase blocks and not the maternal phase blocks. In some cases, the fetal material matches the entirety of a paternal phase block and it is determined that the fetus has that paternal phase block in the paternally inherited chromosome. In other cases, the fetal material matches part of a phase block and then matches a second phase block, where the two phase blocks are on homologous chromosomal regions in the paternal genome. It is determined that a meiotic recombination event occurred at this region, the most likely point of recombination is determined, and a novel fetal phase block that is a combination of two paternal phase blocks is produced.

The sequences of the circulating DNA are compared to the maternal phase blocks. Sites of heterozygosity in the maternal phase blocks are used to determine the most likely phase of the maternally derived fetal chromosomes. The circulating DNA sequences are used to determine the copy number at the heterozygous sites of the maternal genome. Elevated copy numbers of specific maternal phase blocks indicates that the maternally derived chromosome of the fetus contains the sequence of the elevated phase block. In some cases, similarly to that described in the paternal case, at first one phase block of a homologous region will appear elevated, and then a portion of another phase block of the same region will appear elevated, indicating that meiotic recombination has occurred. In these cases, a the most likely region of recombination is determined and a new fetal phase block is constructed from the two maternal phase blocks.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method of determining a presence of a structural variation of a nucleic acid, comprising:
    (a) providing: (i) a plurality of first fragment molecules of the nucleic acid, wherein a given first fragment molecule of the plurality of first fragment molecules comprises the structural variation; and (ii) a plurality of oligonucleotides, wherein each oligonucleotide of the plurality of oligonucleotides comprises a barcode sequence and a random primer sequence, wherein the barcode sequence and the random primer sequence are on a same molecule;
    (b) hybridizing random primer sequences of a subset of oligonucleotides of the plurality of oligonucleotides to multiple different locations of the given first fragment molecule, wherein each oligonucleotide of the subset of oligonucleotides comprises a common barcode sequence;
    (c) generating a plurality of second fragment molecules comprising barcode sequences with the plurality of first fragment molecules and the plurality of oligonucleotides, wherein second fragment molecules of the plurality of second fragment molecules corresponding to the given first fragment molecule comprise the common barcode sequence and are generated by nucleic acid extension reactions using the random primer sequences of the subset of oligonucleotides and using the given first fragment molecule as a template;
    (d) sequencing the plurality of second fragment molecules to provide a plurality of fragment sequences, wherein each of the plurality of fragment sequences corresponding to the given first fragment molecule shares the common barcode sequence; and
    (e) determining a presence of the structural variation by (i) mapping the plurality of fragment sequences to a reference sequence, (ii) identifying the plurality of fragment sequences that share the common barcode sequence, and (iii) identifying the structural variation based on a presence of an elevated amount of the plurality of fragment sequences sharing the common barcode sequence that map to the reference sequence at locations that are further apart than a length of the given first fragment molecule, which elevated amount is relative to a sequence lacking the structural variation.

2. The method of claim 1, wherein the elevated amount is 1% or more with respect to a total number of the first fragment molecules that are derived from a region of the nucleic acid having the structural variation.

3. The method of claim 1, wherein the locations are at least 100 bases apart.

4. The method of claim 1, further comprising identifying the structural variation by creating an assembly of the given first fragment molecule from the plurality of fragment sequences, wherein the plurality of fragment sequences are selected as inputs for the assembly based upon a presence of the common barcode sequence.

5. The method of claim 4, further comprising creating the assembly by generating a consensus sequence from the plurality of fragment sequences.

6. The method of claim 1, wherein the structural variation comprises a translocation.

7. A method of identifying variants in a sequence of a nucleic acid, comprising:
    (a) providing: (i) a plurality of individual fragment molecules of the nucleic acid, and (ii) a plurality of oligonucleotides, wherein each oligonucleotide of the plurality of oligonucleotides comprises a random primer sequence;
    (b) hybridizing random primer sequences of the plurality of oligonucleotides to multiple different locations of each individual fragment molecule of the plurality of individual fragment molecules;
    (c) obtaining nucleic acid sequences of the plurality of individual fragment molecules of the nucleic acid by performing nucleic acid extension reactions using the random primer sequences of the plurality of oligonucleotides and the plurality of individual fragment molecules as templates, the nucleic acid sequences of the plurality of individual fragment molecules each having a length of at least 1 kilobase (kb);
    (d) linking sequences of the nucleic acid sequences of the plurality of individual fragment molecules in one or more inferred contigs; and
    (e) identifying one or more variants from the one or more inferred contigs.

8. The method of claim 7, wherein (c) comprises:
    generating a plurality of barcoded fragments of each individual fragment molecule of the plurality of individual fragment molecules, the barcoded fragments of a given individual fragment molecule having a common barcode;
    sequencing the plurality of barcoded fragments of the plurality of individual fragment molecules, the sequencing providing a sequencing error rate of less than 1%; and
    determining a sequence of the plurality of individual fragment molecules from sequences of the plurality of barcoded fragments and their associated barcodes.

9. The method of claim 8, wherein the linking comprises identifying one or more overlapping sequences between two or more individual fragment molecules of the plurality of individual fragment molecules to link the two or more individual fragment molecules into the one or more inferred contigs.

10. The method of claim 9, wherein the linking comprises identifying one or more common variants between two or more individual fragment molecules of the plurality of individual fragment molecules to link the two or more individual fragment molecules into the one or more inferred contigs.

* * * * *